US010617675B2

(12) United States Patent
Frennesson et al.

(10) Patent No.: US 10,617,675 B2
(45) Date of Patent: Apr. 14, 2020

(54) HEPATITIS C VIRUS INHIBITORS

(71) Applicant: BRISTOL-MYERS SQUIBB COMPANY, Princeton, NJ (US)

(72) Inventors: David B. Frennesson, Naugatuck, CT (US); Piyasena Hewawasam, Middletown, CT (US); Omar D. Lopez, Walkersville, MD (US); Van N. Nguyen, Auburn, MI (US); Mark G. Saulnier, Higganum, CT (US); Yong Tu, Cheshire, CT (US); Alan Xiangdong Wang, Yardley, PA (US); Gan Wang, Cheshire, CT (US); Ningning Xu, Wallingford, CT (US); Roshan Yadavrao Nimje, Bangalore (IN); Hasibur Rahaman, Bangalore (IN); Samayamunthula Venkata Satya Arun Kumar Gupta, Bangalore (IN); Nicholas A. Meanwell, Yardley, PA (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/749,557

(22) PCT Filed: Jul. 27, 2016

(86) PCT No.: PCT/US2016/044158
§ 371 (c)(1),
(2) Date: Feb. 1, 2018

(87) PCT Pub. No.: WO2017/023631
PCT Pub. Date: Feb. 9, 2017

(65) Prior Publication Data
US 2018/0221342 A1 Aug. 9, 2018

(30) Foreign Application Priority Data

Aug. 6, 2015 (IN) .......................... 2415/DEL/2015

(51) Int. Cl.
| | |
|---|---|
| *A61K 31/4178* | (2006.01) |
| *A61K 38/21* | (2006.01) |
| *A61K 45/06* | (2006.01) |
| *A61K 31/417* | (2006.01) |
| *A61K 31/4184* | (2006.01) |
| *A61K 31/7056* | (2006.01) |
| *A61P 31/14* | (2006.01) |
| *A61K 31/4439* | (2006.01) |
| *A61K 31/497* | (2006.01) |

(52) U.S. Cl.
CPC ........ *A61K 31/4178* (2013.01); *A61K 31/417* (2013.01); *A61K 31/4184* (2013.01); *A61K 31/7056* (2013.01); *A61K 38/21* (2013.01); *A61K 45/06* (2013.01); *A61P 31/14* (2018.01); *A61K 31/4439* (2013.01); *A61K 31/497* (2013.01); *A61K 2300/00* (2013.01)

(58) Field of Classification Search
CPC .................................................. A61K 31/4178
See application file for complete search history.

(56) References Cited

U.S. PATENT DOCUMENTS

| | | | |
|---|---|---|---|
| 5,654,451 | A | 8/1997 | Kari |
| 7,745,636 | B2 | 6/2010 | Bachand et al. |
| 7,894,996 | B2 | 2/2011 | Rice et al. |
| 8,288,562 | B2 | 10/2012 | Bachand et al. |
| 8,303,944 | B2 | 11/2012 | Bachand et al. |
| 8,492,553 | B2 | 7/2013 | Bachand et al. |
| 8,574,563 | B2 | 11/2013 | Bachand et al. |
| 8,618,153 | B2 | 12/2013 | Bender et al. |
| 8,642,025 | B2 | 2/2014 | Bachand et al. |
| 8,735,398 | B2 | 5/2014 | Lopez et al. |
| 8,846,023 | B2 | 9/2014 | Bachand et al. |
| 8,900,566 | B2 | 12/2014 | Belma et al. |
| 9,006,455 | B2 | 4/2015 | Pack et al. |
| 9,018,390 | B2 | 4/2015 | Bachand et al. |
| 9,227,961 | B2 | 1/2016 | Bachand et al. |
| 9,303,007 | B2 | 4/2016 | Lopez |
| 9,340,520 | B2 | 5/2016 | Lopez et al. |
| 9,561,212 | B2 | 2/2017 | Romine et al. |
| 2010/0158862 | A1 | 6/2010 | Kim et al. |
| 2011/0092415 | A1 | 4/2011 | Degoey et al. |
| 2011/0206637 | A1 | 8/2011 | Or et al. |
| 2011/0218175 | A1 | 9/2011 | Or et al. |
| 2011/0237636 | A1 | 9/2011 | Belema et al. |

(Continued)

FOREIGN PATENT DOCUMENTS

| | | |
|---|---|---|
| WO | WO1994/015909 | 7/1994 |
| WO | WO-1994015909 | 7/1994 |

(Continued)

OTHER PUBLICATIONS

Lemm, et al., "Identification of Hepatitis C Virus NS5A Inhibitors," J. Virology, 84, pp. 482-491 (2010).

(Continued)

*Primary Examiner* — Svetlana M Ivanova
(74) *Attorney, Agent, or Firm* — Sterne, Kessler, Goldstein & Fox, P.L.L.C.

(57) ABSTRACT

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

9 Claims, No Drawings

(56) References Cited

U.S. PATENT DOCUMENTS

| | | |
|---|---|---|
| 2011/0268697 A1 | 11/2011 | Kim et al. |
| 2013/0071352 A1 | 3/2013 | Dousson et al. |
| 2013/0072523 A1 | 3/2013 | Liu et al. |
| 2013/0072690 A1 | 3/2013 | Chen et al. |
| 2013/0115193 A1 | 5/2013 | Lavoie et al. |
| 2013/0259832 A1 | 10/2013 | Lemm et al. |
| 2014/0018389 A1 | 1/2014 | Lavoie et al. |
| 2014/0205564 A1 | 7/2014 | Romine et al. |
| 2015/0023913 A1 | 1/2015 | Hewawasam et al. |
| 2015/0297568 A1 | 10/2015 | Hewawasam et al. |
| 2015/0322048 A1 | 11/2015 | Lavoie et al. |
| 2015/0335655 A1 | 11/2015 | Gao et al. |
| 2016/0067223 A1 | 3/2016 | Belma et al. |
| 2016/0199355 A1 | 7/2016 | Hewawasam et al. |
| 2016/0311778 A1 | 10/2016 | Bachand et al. |

FOREIGN PATENT DOCUMENTS

| | | | |
|---|---|---|---|
| WO | WO2004/005264 A2 | 1/2004 |
| WO | WO-2004005264 A2 | 1/2004 |
| WO | WO2006/022442 A1 | 3/2006 |
| WO | WO-2006022442 A1 | 3/2006 |
| WO | WO-2006093867 A1 | 9/2006 |
| WO | WO2006093867 A1 | 9/2006 |
| WO | WO2006/133326 A1 | 12/2006 |
| WO | WO-2006133326 A1 | 12/2006 |
| WO | WO2007/031791 A1 | 3/2007 |
| WO | WO-2007031791 A1 | 3/2007 |
| WO | WO2007/058384 A1 | 5/2007 |
| WO | WO-2007058384 A1 | 5/2007 |
| WO | WO2007/076034 A2 | 7/2007 |
| WO | WO2007/077186 A1 | 7/2007 |
| WO | WO 2007/081517 A2 | 7/2007 |
| WO | WO-2007076034 A2 | 7/2007 |
| WO | WO-2007077186 A1 | 7/2007 |
| WO | WO-2007081517 A2 | 7/2007 |
| WO | WO2007/138242 A1 | 12/2007 |
| WO | WO-2007138242 A1 | 12/2007 |
| WO | WO2008/021927 A2 | 2/2008 |
| WO | WO2008/021936 A2 | 2/2008 |
| WO | WO-2008021927 A2 | 2/2008 |
| WO | WO2008021928 A2 | 2/2008 |
| WO | WO-2008021928 A2 | 2/2008 |
| WO | WO 2008021936 A2 | 2/2008 |
| WO | WO 2008/070447 A2 | 6/2008 |
| WO | WO-2008070447 A2 | 6/2008 |
| WO | WO2008/133753 A2 | 11/2008 |
| WO | WO2008/144380 A1 | 11/2008 |
| WO | WO-2008133753 A2 | 11/2008 |
| WO | WO-2008144380 A1 | 11/2008 |
| WO | WO2009/020825 A1 | 2/2009 |
| WO | WO2009/020828 A1 | 2/2009 |
| WO | WO-2009020825 A1 | 2/2009 |
| WO | WO-2009020828 A1 | 2/2009 |
| WO | WO2009/102568 A1 | 8/2009 |
| WO | WO2009/102633 A1 | 8/2009 |
| WO | WO2009/102694 A2 | 8/2009 |
| WO | WO-2009102568 A1 | 8/2009 |
| WO | WO-2009102633 A1 | 8/2009 |
| WO | WO-2009102694 A2 | 8/2009 |
| WO | WO 2010/017401 A1 | 2/2010 |
| WO | WO-2010017401 A1 | 2/2010 |
| WO | WO 2010/039793 A1 | 4/2010 |
| WO | WO-2010039793 A1 | 4/2010 |
| WO | WO2010/062821 A1 | 6/2010 |
| WO | WO 2010/065668 A1 | 6/2010 |
| WO | WO2010/065674 A1 | 6/2010 |
| WO | WO2010/065681 A1 | 6/2010 |
| WO | WO-2010062821 A1 | 6/2010 |
| WO | WO-2010065668 A1 | 6/2010 |
| WO | WO-2010065674 A1 | 6/2010 |
| WO | WO-2010065681 A1 | 6/2010 |
| WO | WO2010/075376 A2 | 7/2010 |
| WO | WO-2010075376 A2 | 7/2010 |
| WO | WO2010/091413 A1 | 8/2010 |
| WO | WO2010/094977 A1 | 8/2010 |
| WO | WO2010/096302 A1 | 8/2010 |
| WO | WO2010/096462 A1 | 8/2010 |
| WO | WO2010/096777 A1 | 8/2010 |
| WO | WO-2010091413 A1 | 8/2010 |
| WO | WO-2010094977 A1 | 8/2010 |
| WO | WO-2010096302 A1 | 8/2010 |
| WO | WO-2010096462 A1 | 8/2010 |
| WO | WO-2010096777 A1 | 8/2010 |
| WO | WO2010/099527 A1 | 9/2010 |
| WO | WO2010/111483 A1 | 9/2010 |
| WO | WO2010/111534 A1 | 9/2010 |
| WO | WO2010/111673 A1 | 9/2010 |
| WO | WO-2010099527 A1 | 9/2010 |
| WO | WO-2010111483 A1 | 9/2010 |
| WO | WO-2010111534 A1 | 9/2010 |
| WO | WO-2010111673 A1 | 9/2010 |
| WO | WO2010/117635 A1 | 10/2010 |
| WO | WO2010/117704 A1 | 10/2010 |
| WO | WO2010/117977 A1 | 10/2010 |
| WO | WO2010/120621 A1 | 10/2010 |
| WO | WO2010/120935 A1 | 10/2010 |
| WO | WO2010/122162 A1 | 10/2010 |
| WO | WO-2010117635 A1 | 10/2010 |
| WO | WO-2010117704 A1 | 10/2010 |
| WO | WO-2010120621 A1 | 10/2010 |
| WO | WO-2010120935 A1 | 10/2010 |
| WO | WO-2010122162 A1 | 10/2010 |
| WO | WO2010/132538 A1 | 11/2010 |
| WO | WO2010/132601 A1 | 11/2010 |
| WO | WO-2010132538 A1 | 11/2010 |
| WO | WO-2010132601 A1 | 11/2010 |
| WO | WO2010/138368 A1 | 12/2010 |
| WO | WO2010/138488 A1 | 12/2010 |
| WO | WO2010/138790 A1 | 12/2010 |
| WO | WO2010/138791 A1 | 12/2010 |
| WO | WO2010/144646 A2 | 12/2010 |
| WO | WO2010/148006 A1 | 12/2010 |
| WO | WO-2010138488 A1 | 12/2010 |
| WO | WO-2010138790 A1 | 12/2010 |
| WO | WO-2010138791 A1 | 12/2010 |
| WO | WO-2010144646 A2 | 12/2010 |
| WO | WO-2010148006 A1 | 12/2010 |
| WO | WO2011/004276 A1 | 1/2011 |
| WO | WO2011/009084 A2 | 1/2011 |
| WO | WO-2011004276 A1 | 1/2011 |
| WO | WO-2011009084 A2 | 1/2011 |
| WO | WO2011/015657 A1 | 2/2011 |
| WO | WO2011/015658 A1 | 2/2011 |
| WO | WO-2011015657 A1 | 2/2011 |
| WO | WO-2011015658 A1 | 2/2011 |
| WO | WO2011/026920 A1 | 3/2011 |
| WO | WO2011/028596 A1 | 3/2011 |
| WO | WO2011/031904 A1 | 3/2011 |
| WO | WO2011/031934 A1 | 3/2011 |
| WO | WO-2011028596 A1 | 3/2011 |
| WO | WO-2011031904 A1 | 3/2011 |
| WO | WO-2011031934 A1 | 3/2011 |
| WO | WO2011/046811 A1 | 4/2011 |
| WO | WO2011/050146 A1 | 4/2011 |
| WO | WO-2011046811 A1 | 4/2011 |
| WO | WO-2011050146 A1 | 4/2011 |
| WO | WO2011/054834 A1 | 5/2011 |
| WO | WO2011/059850 A1 | 5/2011 |
| WO | WO2011/059887 A1 | 5/2011 |
| WO | WO2011/060000 A1 | 5/2011 |
| WO | WO-2011054834 A1 | 5/2011 |
| WO | WO-2011059850 A1 | 5/2011 |
| WO | WO-2011059887 A1 | 5/2011 |
| WO | WO-2011060000 A1 | 5/2011 |
| WO | WO2011/066241 A1 | 6/2011 |
| WO | WO2011/068941 A2 | 6/2011 |
| WO | WO2011/075439 A1 | 6/2011 |
| WO | WO2011/075607 A1 | 6/2011 |
| WO | WO2011/075615 A1 | 6/2011 |
| WO | WO2011/079327 A1 | 6/2011 |
| WO | WO-2011066241 A1 | 6/2011 |
| WO | WO-2011068941 A2 | 6/2011 |
| WO | WO-2011075439 A1 | 6/2011 |

(56) References Cited

FOREIGN PATENT DOCUMENTS

| | | |
|---|---|---|
| WO | WO-2011075607 A1 | 6/2011 |
| WO | WO-2011075615 A1 | 6/2011 |
| WO | WO-2011079327 A1 | 6/2011 |
| WO | WO2011/081918 A1 | 7/2011 |
| WO | WO2011/082077 A1 | 7/2011 |
| WO | WO2011/087740 A1 | 7/2011 |
| WO | WO2011/091417 A1 | 7/2011 |
| WO | WO2011/091446 A1 | 7/2011 |
| WO | WO-2011081918 A1 | 7/2011 |
| WO | WO-2011082077 A1 | 7/2011 |
| WO | WO-2011087740 A1 | 7/2011 |
| WO | WO-2011091417 A1 | 7/2011 |
| WO | WO-2011091446 A1 | 7/2011 |
| WO | WO2011/091532 A1 | 8/2011 |
| WO | WO-2011-091532 A1 | 8/2011 |
| WO | WO2011/109037 A1 | 9/2011 |
| WO | WO2011/112429 A1 | 9/2011 |
| WO | WO2011/119853 A1 | 9/2011 |
| WO | WO2011/119860 A1 | 9/2011 |
| WO | WO2011/119870 A1 | 9/2011 |
| WO | WO-2011109037 A1 | 9/2011 |
| WO | WO-2011112429 A1 | 9/2011 |
| WO | WO-2011119853 A1 | 9/2011 |
| WO | WO-2011119860 A1 | 9/2011 |
| WO | WO-2011119870 A1 | 9/2011 |
| WO | WO2011/127350 A1 | 10/2011 |
| WO | WO-2011026920 A1 | 10/2011 |
| WO | WO-2011127350 A1 | 10/2011 |
| WO | WO2011/146401 A1 | 11/2011 |
| WO | WO-2011146401 A1 | 11/2011 |
| WO | WO2011/149856 A1 | 12/2011 |
| WO | WO2011/150243 A1 | 12/2011 |
| WO | WO2011/153396 A1 | 12/2011 |
| WO | WO2011/154871 A1 | 12/2011 |
| WO | WO2011/156543 A2 | 12/2011 |
| WO | WO-2011149856 A1 | 12/2011 |
| WO | WO-2011150243 A1 | 12/2011 |
| WO | WO-2011153396 A1 | 12/2011 |
| WO | WO-2011154871 A1 | 12/2011 |
| WO | WO-2011156543 A2 | 12/2011 |
| WO | WO-2011156578 A1 | 12/2011 |
| WO | WO2011156578 A1 | 12/2011 |
| WO | WO2012/003642 A1 | 1/2012 |
| WO | WO2012/009394 A2 | 1/2012 |
| WO | WO-2012003642 A1 | 1/2012 |
| WO | WO-2012009394 A2 | 1/2012 |
| WO | WO2012/013643 A1 | 2/2012 |
| WO | WO2012/018325 A1 | 2/2012 |
| WO | WO2012/018534 A2 | 2/2012 |
| WO | WO2012/018829 A1 | 2/2012 |
| WO | WO2012/020036 A1 | 2/2012 |
| WO | WO2012/021591 A1 | 2/2012 |
| WO | WO2012/021704 A1 | 2/2012 |
| WO | WO-2012013643 A1 | 2/2012 |
| WO | WO-2012018534 A2 | 2/2012 |
| WO | WO-2012018829 A1 | 2/2012 |
| WO | WO-2012020036 A1 | 2/2012 |
| WO | WO-2012021591 A1 | 2/2012 |
| WO | WO-2012021704 A1 | 2/2012 |
| WO | WO2012/027712 A2 | 3/2012 |
| WO | WO2012/040389 A2 | 3/2012 |
| WO | WO-2012027712 A2 | 3/2012 |
| WO | WO-2012040389 A2 | 3/2012 |
| WO | WO2012/040923 A1 | 4/2012 |
| WO | WO2012/040924 A1 | 4/2012 |
| WO | WO2012/041014 A1 | 4/2012 |
| WO | WO2012/041227 A1 | 4/2012 |
| WO | WO2012/048421 A1 | 4/2012 |
| WO | WO2012/050848 A1 | 4/2012 |
| WO | WO2012/050850 A1 | 4/2012 |
| WO | WO2012/050918 A2 | 4/2012 |
| WO | WO2012/051361 A1 | 4/2012 |
| WO | WO-2012040923 A1 | 4/2012 |
| WO | WO-2012040924 A1 | 4/2012 |
| WO | WO-2012041014 A1 | 4/2012 |
| WO | WO-2012041227 A1 | 4/2012 |
| WO | WO-2012048421 A1 | 4/2012 |
| WO | WO-2012050848 A1 | 4/2012 |
| WO | WO-2012050850 A1 | 4/2012 |
| WO | WO-2012050918 A2 | 4/2012 |
| WO | WO-2012051361 A1 | 4/2012 |
| WO | WO2012/061552 A1 | 5/2012 |
| WO | WO2012/068234 A2 | 5/2012 |
| WO | WO-2012061552 A1 | 5/2012 |
| WO | WO-2012068234 A2 | 5/2012 |
| WO | WO2012/074437 A2 | 6/2012 |
| WO | WO2012/083043 A1 | 6/2012 |
| WO | WO2012/083048 A2 | 6/2012 |
| WO | WO2012/083053 A2 | 6/2012 |
| WO | WO2012/083058 A2 | 6/2012 |
| WO | WO2012/083059 A1 | 6/2012 |
| WO | WO2012/083061 A2 | 6/2012 |
| WO | WO2012/083170 A1 | 6/2012 |
| WO | WO2012/087596 A1 | 6/2012 |
| WO | WO-2012074437 A2 | 6/2012 |
| WO | WO-2012083043 A1 | 6/2012 |
| WO | WO-2012083048 A2 | 6/2012 |
| WO | WO-2012083053 A2 | 6/2012 |
| WO | WO-2012083058 A2 | 6/2012 |
| WO | WO-2012083059 A1 | 6/2012 |
| WO | WO-2012083061 A2 | 6/2012 |
| WO | WO2012083164 A1 | 6/2012 |
| WO | WO-2012083164 A1 | 6/2012 |
| WO | WO-2012083170 A1 | 6/2012 |
| WO | WO-2012087596 A1 | 6/2012 |
| WO | WO2012087976 A2 | 6/2012 |
| WO | WO-2012087976 A2 | 6/2012 |
| WO | WO2013/098313 A1 | 7/2012 |
| WO | WO2013/098320 A1 | 7/2012 |
| WO | WO-2013098313 A1 | 7/2012 |
| WO | WO-2013098320 A1 | 7/2012 |
| WO | WO2012/116257 A1 | 8/2012 |
| WO | WO2012109080 A1 | 8/2012 |
| WO | WO-2012109080 A1 | 8/2012 |
| WO | WO-2012116257 A1 | 8/2012 |
| WO | WO2012/123298 A1 | 9/2012 |
| WO | WO2012/125926 A2 | 9/2012 |
| WO | WO-2012122716 A1 | 9/2012 |
| WO | WO2012122716 A1 | 9/2012 |
| WO | WO-2012123298 A1 | 9/2012 |
| WO | WO-2012125926 A2 | 9/2012 |
| WO | WO2012/135581 A1 | 10/2012 |
| WO | WO-2012135581 A1 | 10/2012 |
| WO | WO2012/154777 A1 | 11/2012 |
| WO | WO-2012154777 A1 | 11/2012 |
| WO | WO-2012162578 A2 | 11/2012 |
| WO | WO2012162578 A2 | 11/2012 |
| WO | WO-2012162580 A2 | 11/2012 |
| WO | WO2012162580 A2 | 11/2012 |
| WO | WO2012/166716 A2 | 12/2012 |
| WO | WO2012/175581 A1 | 12/2012 |
| WO | WO-2012166716 A2 | 12/2012 |
| WO | WO-2012175581 A1 | 12/2012 |
| WO | WO2013/007106 A1 | 1/2013 |
| WO | WO-2013007106 A1 | 1/2013 |
| WO | WO2013/021337 A1 | 2/2013 |
| WO | WO2013/021344 A1 | 2/2013 |
| WO | WO2013/022810 A1 | 2/2013 |
| WO | WO2013/028953 A1 | 2/2013 |
| WO | WO-2013021337 A1 | 2/2013 |
| WO | WO-2013021344 A1 | 2/2013 |
| WO | WO-2013022810 A1 | 2/2013 |
| WO | WO-2013028953 A1 | 2/2013 |
| WO | WO2013/030750 A1 | 3/2013 |
| WO | WO2013/039876 A1 | 3/2013 |
| WO | WO2013/039878 A1 | 3/2013 |
| WO | WO-2013030750 A1 | 3/2013 |
| WO | WO-2013039876 A1 | 3/2013 |
| WO | WO-2013039878 A1 | 3/2013 |
| WO | WO2013/052362 A1 | 4/2013 |
| WO | WO2013/052369 A1 | 4/2013 |
| WO | WO2013/053657 A1 | 4/2013 |
| WO | WO2013/059278 A2 | 4/2013 |
| WO | WO2013/059630 A1 | 4/2013 |

(56) References Cited

FOREIGN PATENT DOCUMENTS

| | | |
|---|---|---|
| WO | WO2013/059638 A1 | 4/2013 |
| WO | WO-2013052362 A1 | 4/2013 |
| WO | WO-2013052369 A1 | 4/2013 |
| WO | WO-2013053657 A1 | 4/2013 |
| WO | WO-2013059278 A2 | 4/2013 |
| WO | WO-2013059630 A1 | 4/2013 |
| WO | WO-2013059638 A1 | 4/2013 |
| WO | WO2013/066753 A1 | 5/2013 |
| WO | WO2013/075029 A1 | 5/2013 |
| WO | WO-2013066753 A1 | 5/2013 |
| WO | WO-2013075029 A1 | 5/2013 |
| WO | WO2013/087743 A1 | 6/2013 |
| WO | WO2013/095275 A1 | 6/2013 |
| WO | WO-2013087743 A1 | 6/2013 |
| WO | WO-2013095275 A1 | 6/2013 |
| WO | WO2013/101550 A1 | 7/2013 |
| WO | WO2013/106520 A1 | 7/2013 |
| WO | WO-2013101550 A1 | 7/2013 |
| WO | WO-2013101552 A1 | 7/2013 |
| WO | WO2013101552 A1 | 7/2013 |
| WO | WO-2013106520 A1 | 7/2013 |
| WO | WO2013/118097 A1 | 8/2013 |
| WO | WO2013/118102 A1 | 8/2013 |
| WO | WO2013/123092 A1 | 8/2013 |
| WO | WO-2013118097 A1 | 8/2013 |
| WO | WO-2013118102 A1 | 8/2013 |
| WO | WO-2013123092 A1 | 8/2013 |
| WO | WO2013/173492 A1 | 11/2013 |
| WO | WO-2013173492 A1 | 11/2013 |
| WO | WO2014/036244 A1 | 3/2014 |
| WO | WO-2014036244 A1 | 3/2014 |
| WO | WO2014/065791 A1 | 5/2014 |
| WO | WO2014/074604 A2 | 5/2014 |
| WO | WO-2014065791 A1 | 5/2014 |
| WO | WO-2014074604 A2 | 5/2014 |
| WO | WO2014/100500 A1 | 6/2014 |
| WO | WO-2014100500 A1 | 6/2014 |
| WO | WO2015/009744 A1 | 1/2015 |
| WO | WO-2015009744 A1 | 1/2015 |
| WO | WO2015/017382 A1 | 2/2015 |
| WO | WO2015/026454 A1 | 2/2015 |
| WO | WO-2015017382 A1 | 2/2015 |
| WO | WO-2015026454 A1 | 2/2015 |
| WO | WO2015/042375 A1 | 3/2015 |
| WO | WO-2015042375 A1 | 3/2015 |
| WO | WO2015/088817 A1 | 6/2015 |
| WO | WO-2015088817 A1 | 6/2015 |
| WO | WO2015/110048 A1 | 7/2015 |
| WO | WO-2015110048 A1 | 7/2015 |
| WO | WO2015/134560 A1 | 9/2015 |
| WO | WO2015/134561 A1 | 9/2015 |
| WO | WO-2015134560 A1 | 9/2015 |
| WO | WO-2015134561 A1 | 9/2015 |
| WO | WO2015/160907 A2 | 10/2015 |
| WO | WO-2015160907 A2 | 10/2015 |

OTHER PUBLICATIONS

Gao, et al., Chemical Genetics Strategy Identifies an HCV NS5A Inhibitor with a Potent Clinical Effect, Nature, 465, pp. 96-100 (2010).
Fridell, et al., "Resistance Analysis of the Hepatitis C Virus NS5A Inhibitor BMS-790052 in an In Vitro Replicon System," Antimicrob. Agents Chemother., 54, pp. 3641-3650 (2010).
Romine, et al. "Inhibitors of HCV NS5A: From Iminothiazolidinones to Symmetrical Stilbenes," ACS Med. Chem. Lett., 2, pp. 224-229 (2011).
O'Boyle, et al., "Development of a Cell-based High-Throughput Specificity Screen Using a HCV/BVDV Dual Replicon Assay," Antimicrob. Agents Chemother., 49, pp. 1346-1353 (2005).
Lemm, et al, "Discovery of Potent NS5A Inhibitors with Dimeric Structures," Antimicrob. Agents and Chemother., 55, pp. 3795-3802 (2011).
Fridell, et al., "Distinct Functions of NS5A in HCV RNA Replication Uncovered by Studies with the NS5A Inhibitor BMS-790052," J Virol., 85, pp. 7312-7320 (2011).
Fridell, et al., "Genotypic and Phenotypic Analysis of Variants Resistant to HCV NS5A Replication Complex Inhibitor BMS-790052: In Vitro and In Vivo Correlations," Hepatology, 54, pp. 1924-1935 (2011).
Nettles, et al., "Multiple ascending dose study to evaluate BMS-790052 a novel NS5A inhibitor in subjects infected with hepatitis C virus genotype 1.," Hepatology, 54, pp. 1956-1966 (2011).
Qiu, et al., "The effects of NS5A inhibitors on NS5A phosphorylation polyprotein processing and localization," J. Gen. Virology, 92, pp. 2502-2511 (2011).
Sun, "Impact of a baseline polymorphism on the emergence of resistance to the HCV NS5A replication complex inhibitor BMS-790052," Hepatology, 55, pp. 1956-1965 (2011).
Wang, et al., "In Vitro Activity of BMS-790052 on Hepatitis C Virus Genotype 4 NS5A, Antimicrob. Agents and Chemother.," 56, pp. 1588-1590 (2012).
Wang, et al., "Hepatitis C virus RNA elimination and development of resistance in replicon cells treated with BMS-790052," Antimicrob. Agents and Chemother., 56, pp. 1350-1358 (2012).
Pelosi, et al. "Effect of NS5A Inhibitor Combinations on HCV Replication In Vitro.,," Antimicrob. Agents and Chemother., 56, pp. 5230-5639 (2012).
Wang, et al., "In vitro Activity of Daclatasvir on Hepatitis C Virus Genotype 3 NS5A," Antimicrob. Agents and Chemother., 57, pp. 611-613 (2013).
Fridell, R., et al., "Resistance Analysis of the Hepatitis C Virus NS5A Inhibitor BMS-790052 in an In Vitro Replicon System," Antimicrobial Agents and Chemotherapy, 54: 3641-3650, American Society for Microbiology, United States, (2010).
O'Boyle, D., et al., "Development of a Cell-based High-Throughput Specificity Screen Using a HCV/BVDV Dual Replicon Assay," Antimicrobial Agents and Chemotherapy, 49:1346-1353, American Society for Microbiology, United States (2005).
Fridell, R., et al., "Distinct Functions of NS5A in HCV RNA Replication Uncovered by Studies with the NS5A Inhibitor BMS-790052," Journal of Virology, 85: 7312-7320, American Society of Microbiology, United States (2011).
Fridell, R., et al., "Genotypic and Phenotypic Analysis of Variants Resistant to HCV NS5A Replication Complex Inhibitor BMS-790052: In Vitro and In Vivo Correlations," Hepatology, 54:1924-1935, The American Association for the Study of Liver Diseases, United States (2011).
Qiu, D., et al., "The effects of NS5A inhibitors on NS5A phosphorylation polyprotein processing and localization," Journal of General Virology, 92: 2502-2511, Microbiology Society, United Kingdom (2011).
Sun, J., et al., "Impact of a baseline polymorphism on the emergence of resistance to the HCV NS5A replication complex inhibitor BMS-790052," Hepatology, 55:1956-1965, The American Association for the Study of Liver Disease, United States (2011).
Wang, C., et al., "In Vitro Activity of BMS-790052 on Hepatitis C Virus Genotype 4 NS5A, Antimicrobial Agents and Chemotherapy," 56:588-1590, American Society for Microbiology, United States (2012).
Wang, C., et al., "Hepatitis C virus RNA elimination and development of resistance in replicon cells treated with BMS-790052," Antimicrobial Agents and Chemotherapy, 56:1350-1358, American Society for Microbiology, United States (2012).
Pelosi, L., et al. "Effect of NS5A Inhibitor Combinations on HCV Replication In Vitro.,," Antimicrobial Agents and Chemotherapy, 56: 5230-5639, American Society for Microbiology, United States (2012).
Wang, C., et al., "In Vitro Activity of Daclatasvir on Hepatitis C Virus Genotype 3 NS5A," Antimicrobial Agents and Chemotherapy, 57: 611-613, American Society for Microbiology (2013).

HEPATITIS C VIRUS INHIBITORS

This application claims priority to Indian Provisional Patent Application Serial No. 2415/DEL/2015, filed Aug. 6, 2015, which is incorporated by reference in its entirety.

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Over the past decade the standard of care for the treatment of chronic HCV has evolved from a combination of pegylated-interferon and ribavirin to treatment consisting exclusively of small molecules. Recently approved drug combinations that can be administered without interferon provide a major improvement in the percentage of patients who experience SVR as well as the treatment duration required to achieve SVR. However, there is a clear and urgent need to develop additional therapies to combat resistance and to improve efficacy across all HCV genotypes.

HCV is a positive-stranded RNA virus of approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein is a cofactor for the NS3 protease. The formation of a NS3-NS4A complex is necessary for proper protease activity. The NS3 protein also exhibits nucleoside triphosphatase and RNA helicase activities. NS5A is a multi-functional protein required for viral RNA replication and virion assembly. NS5B (also referred to herein as HCV polymerase) is a RNA-dependent RNA polymerase that is responsible for viral RNA synthesis.

Considerable heterogeneity is found within the nucleotide and encoded amino acid sequence throughout the HCV genome due to the high error rate of the encoded RNA-dependent RNA polymerase which lacks a proof-reading capability. The clinical significance of the genetic heterogeneity of HCV is the propensity for mutations to arise during monotherapy treatment, thus combination therapies with HCV inhibitors that have pan-genotype coverage and act via independent mechanisms are desired.

Compounds which selectively inhibit HCV viral replication and are useful for treating HCV-infected patients are desired. In particular, compounds which effectively inhibit the function of the NS5A protein are desired. The function and the essential role of NS5A protein for HCV replication are described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); M. Gao, et al, *Nature* (2010); C. Rice, et al., WO2006093867.

A method has been described to identify compounds that demonstrate synergistic inhibition of HCV replicon activity when combined with the HCV NS5A inhibitor such as BMS-790052 (PCT/US2011/043785, filed Jul. 13, 2011). In brief, each compound, when tested individually versus some NS5A resistant variants, is essentially inactive or much less active and only has synergistic inhibitory activity when tested in combination with an NS5A-targeting compound. The synergistic compounds were identified using titrations of test compounds in the presence of fixed concentrations of HCV NS5A inhibitors such as BMS-790052. The compounds of the present disclosure provide improved activity against the HCV virus.

In a first aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound selected from:

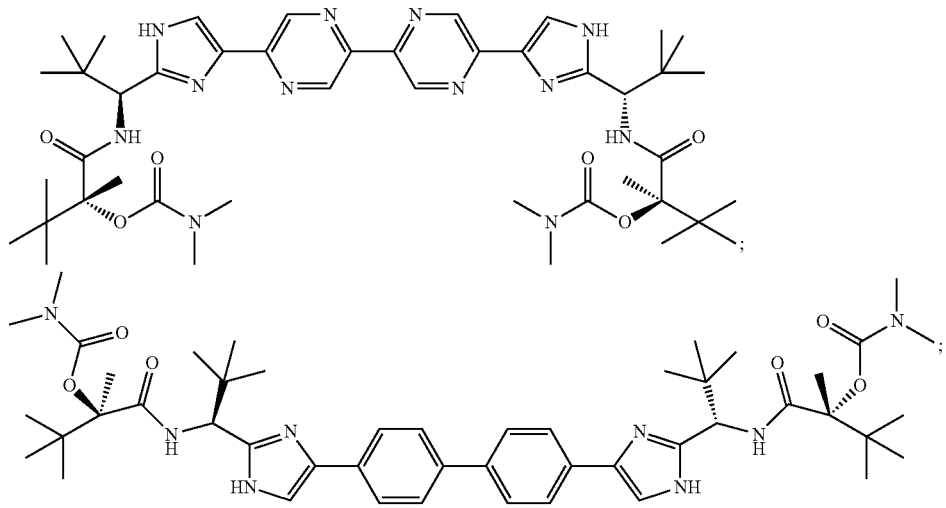

-continued
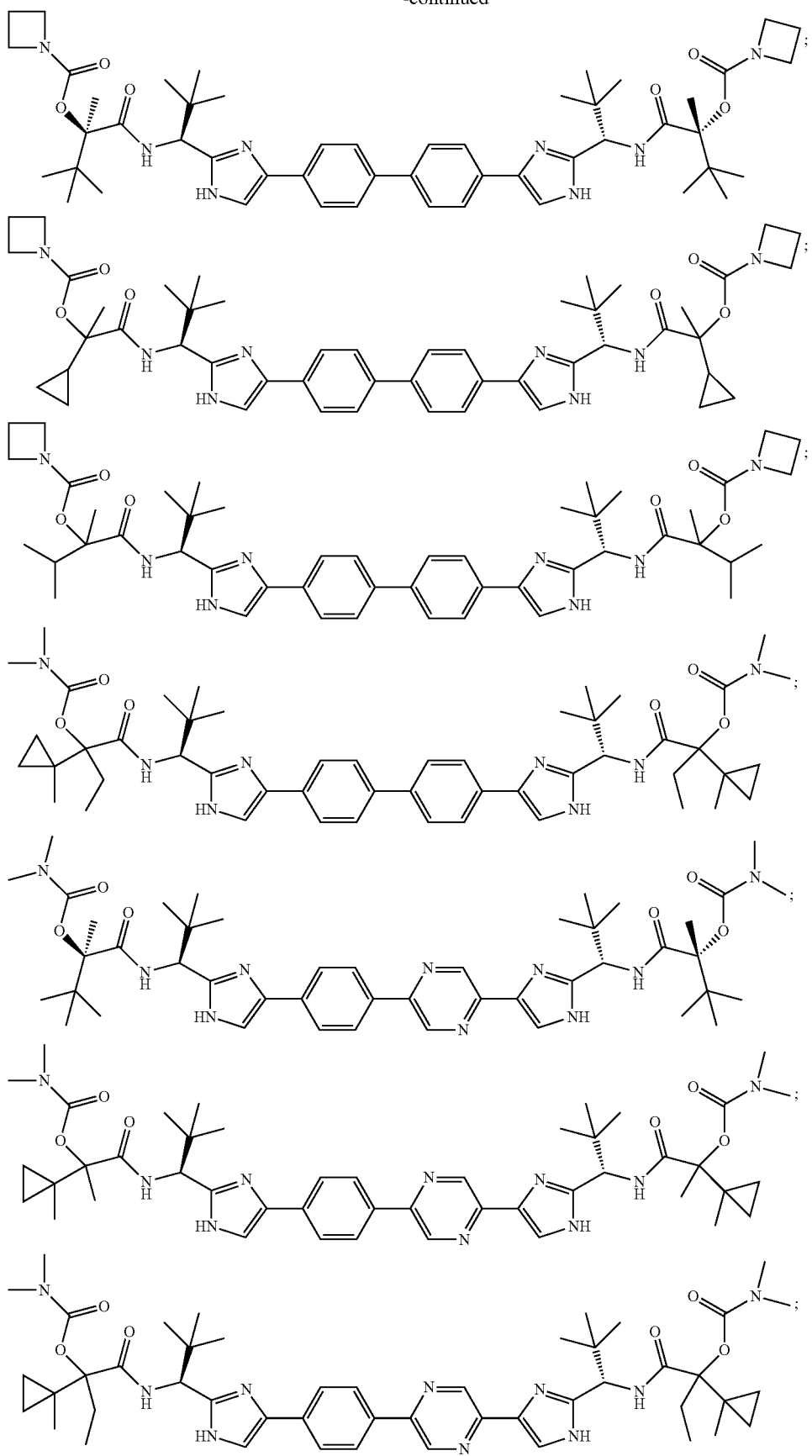

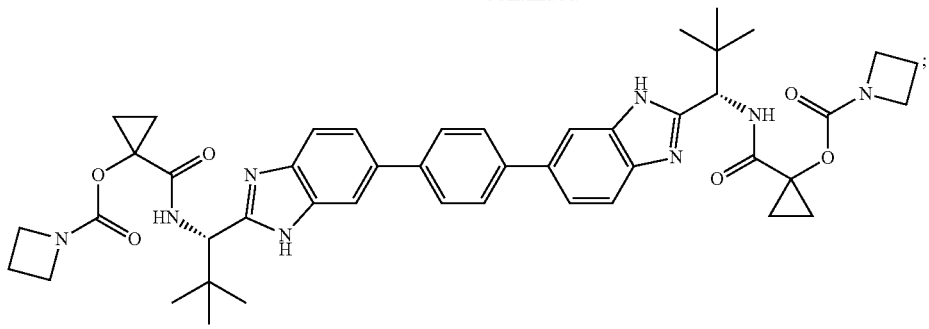
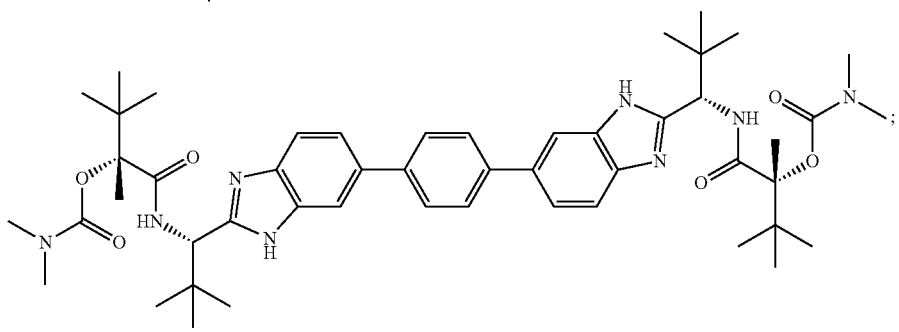
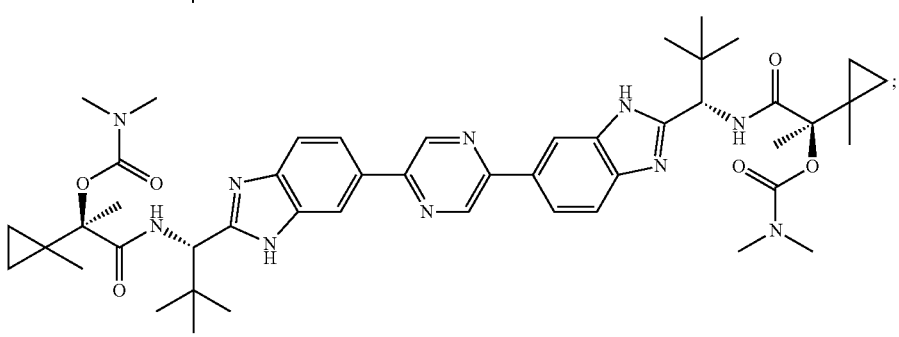
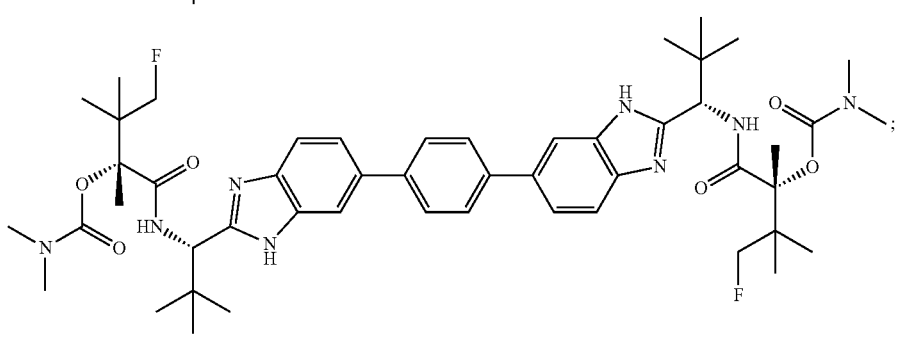
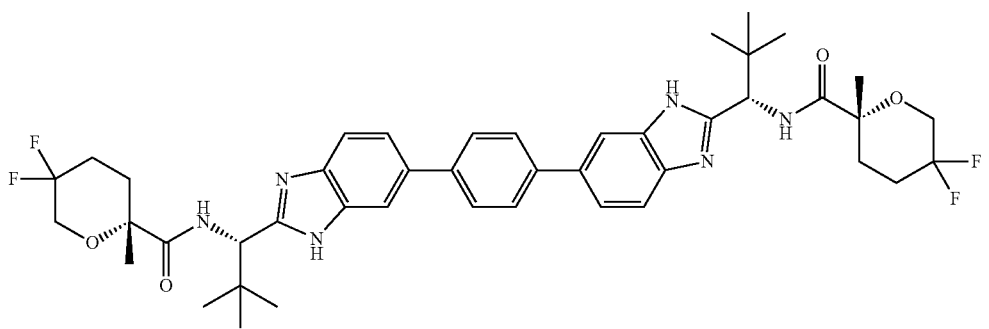

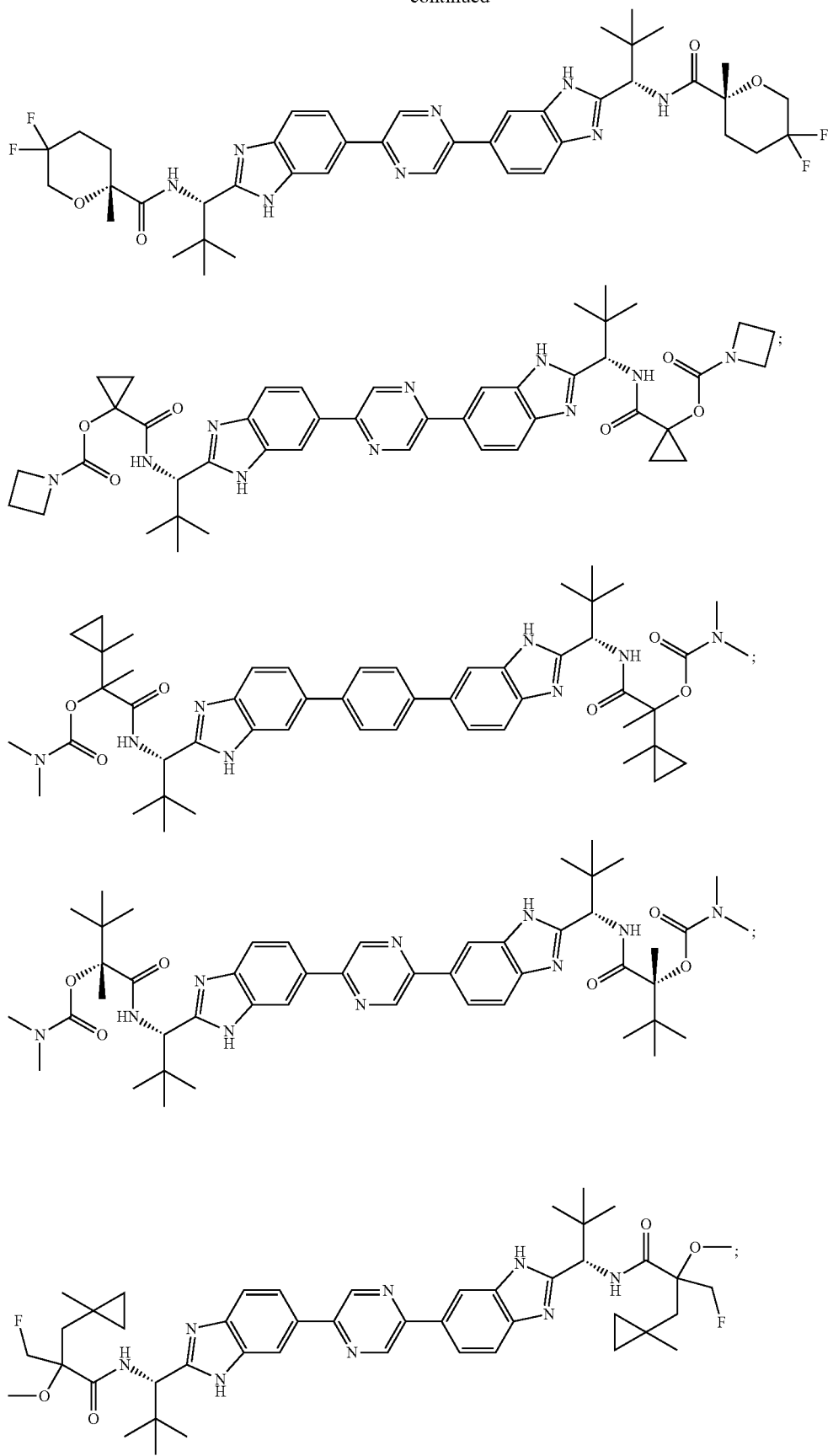

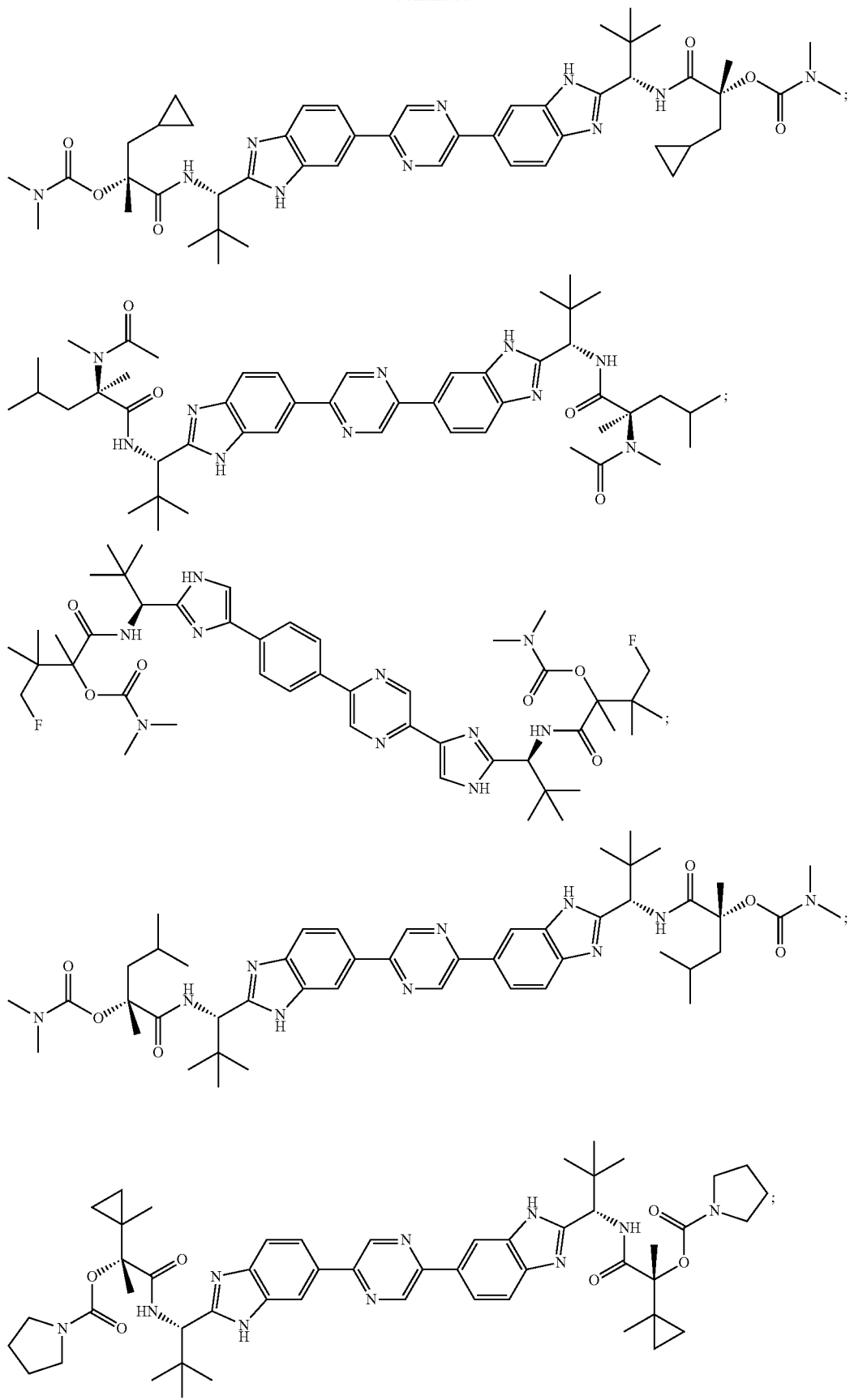

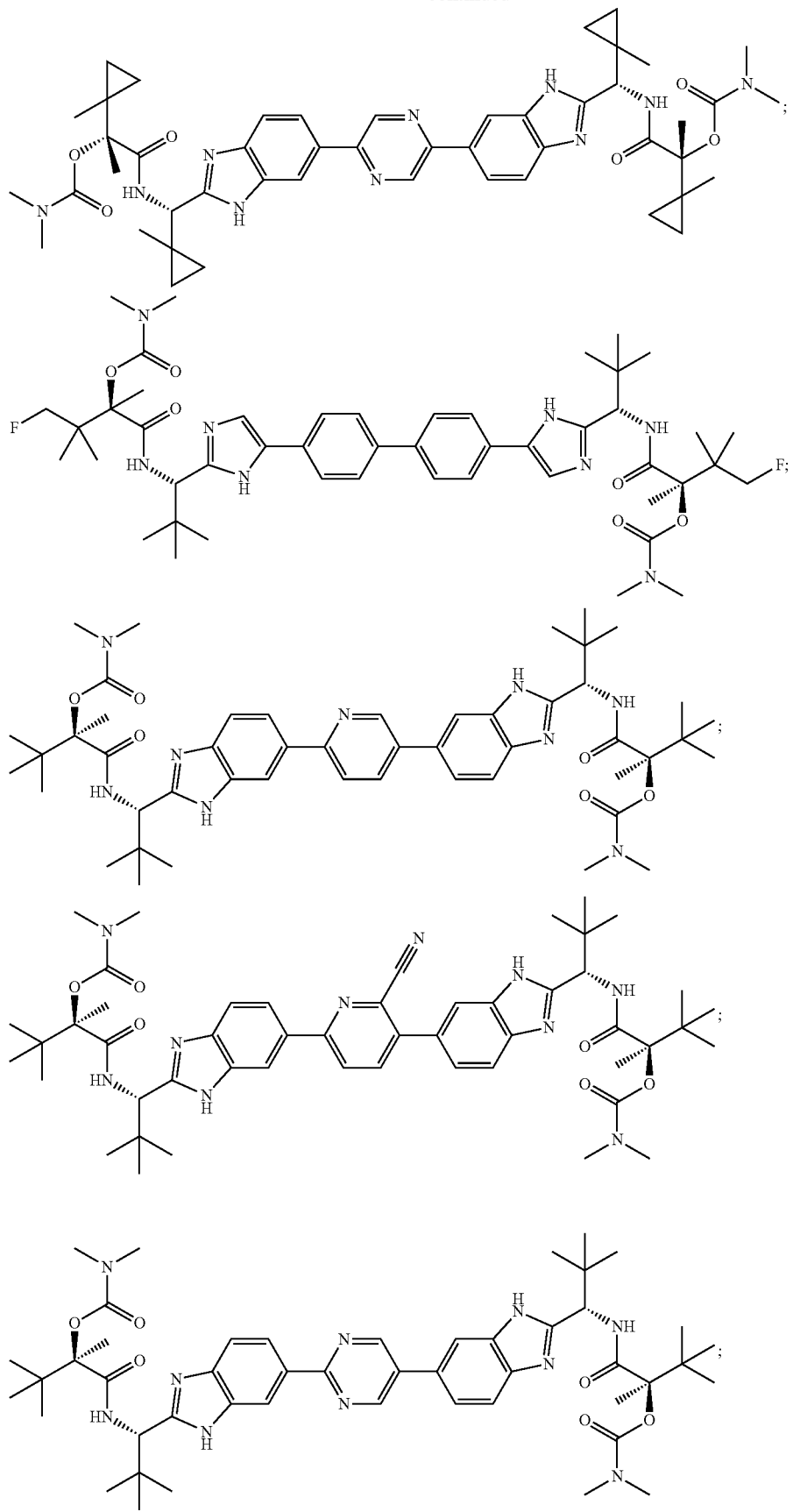

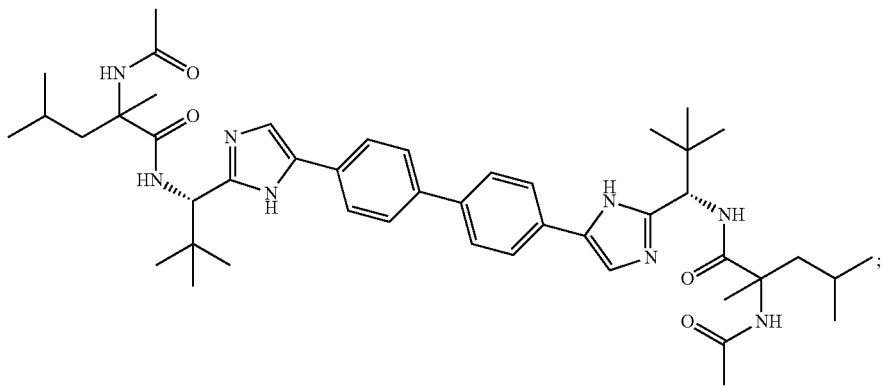
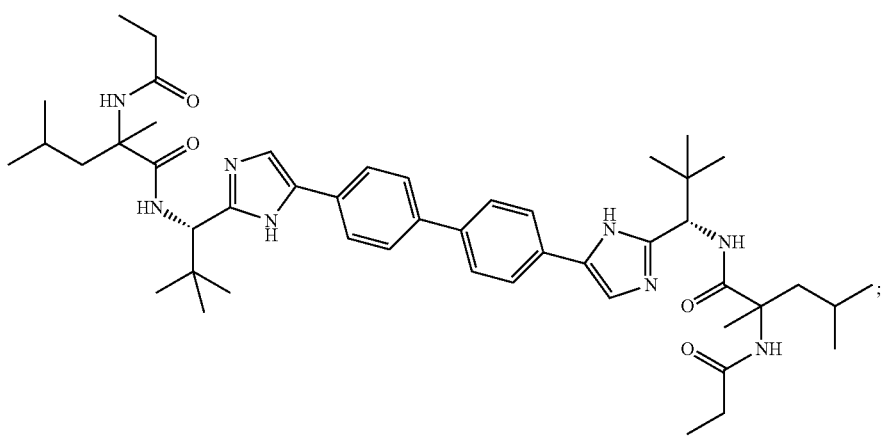
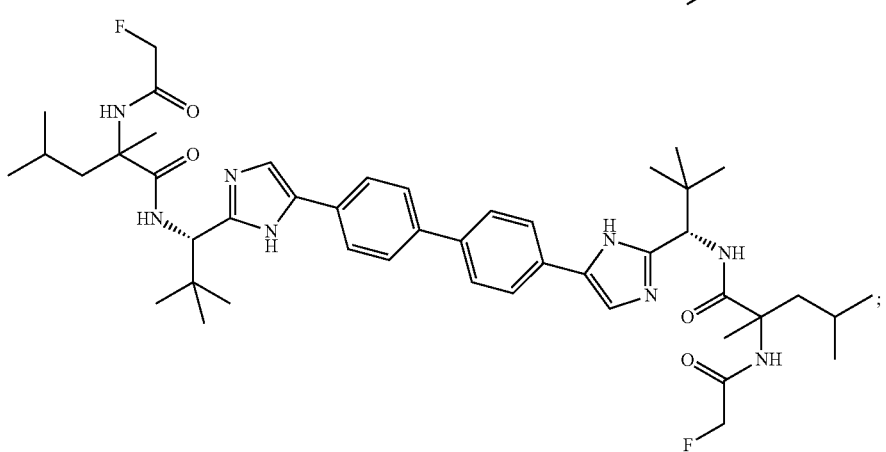
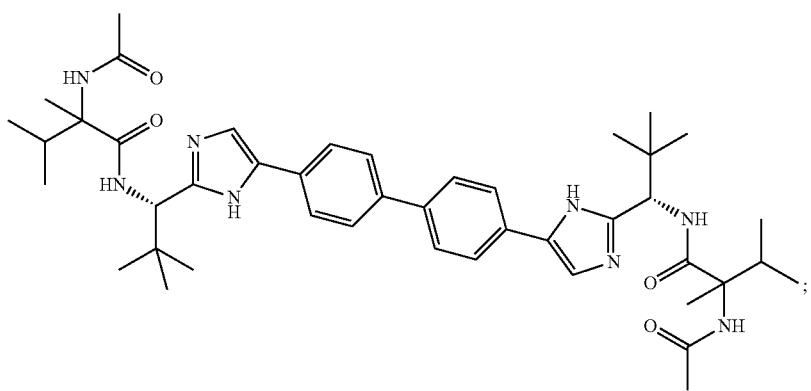

-continued
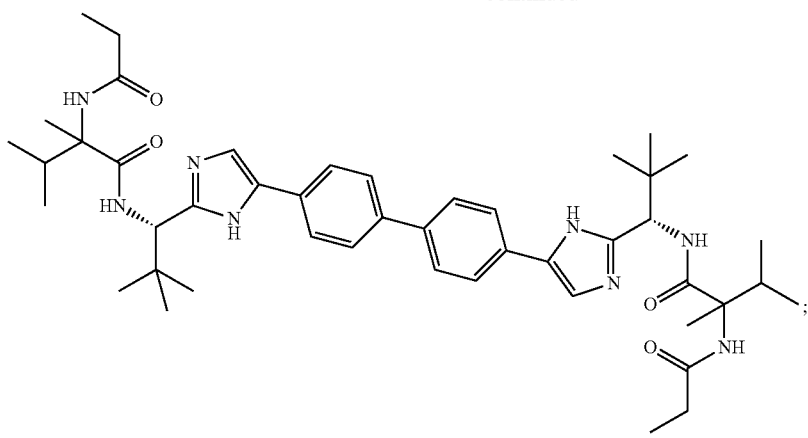
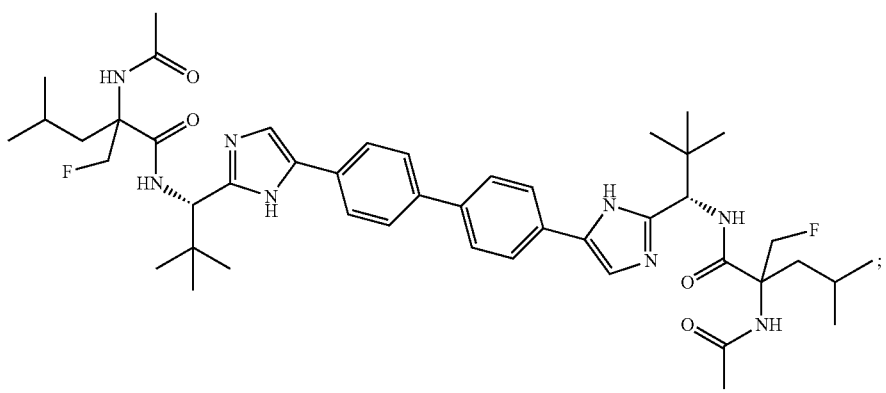
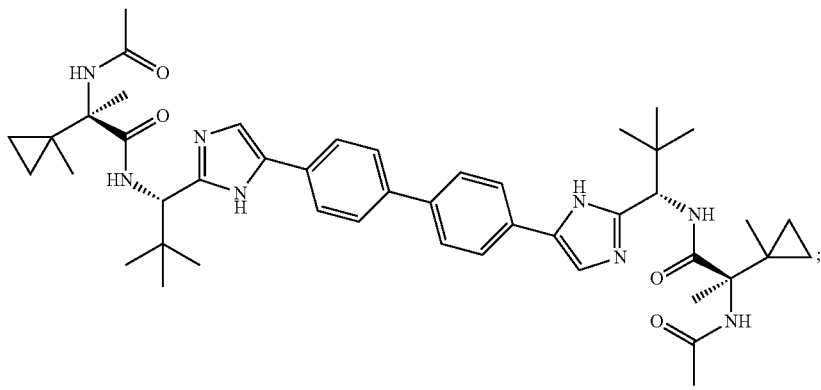
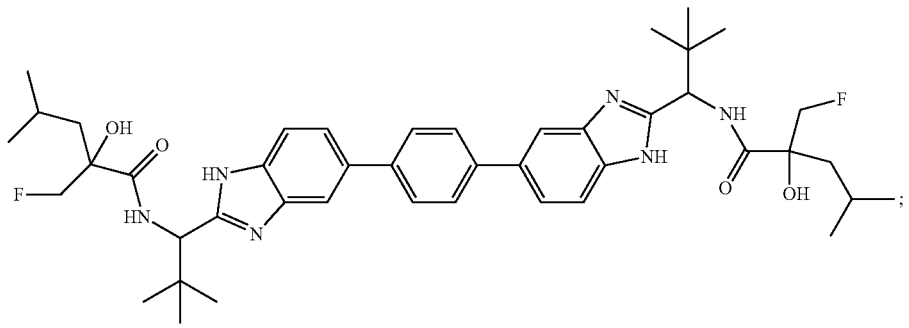

-continued
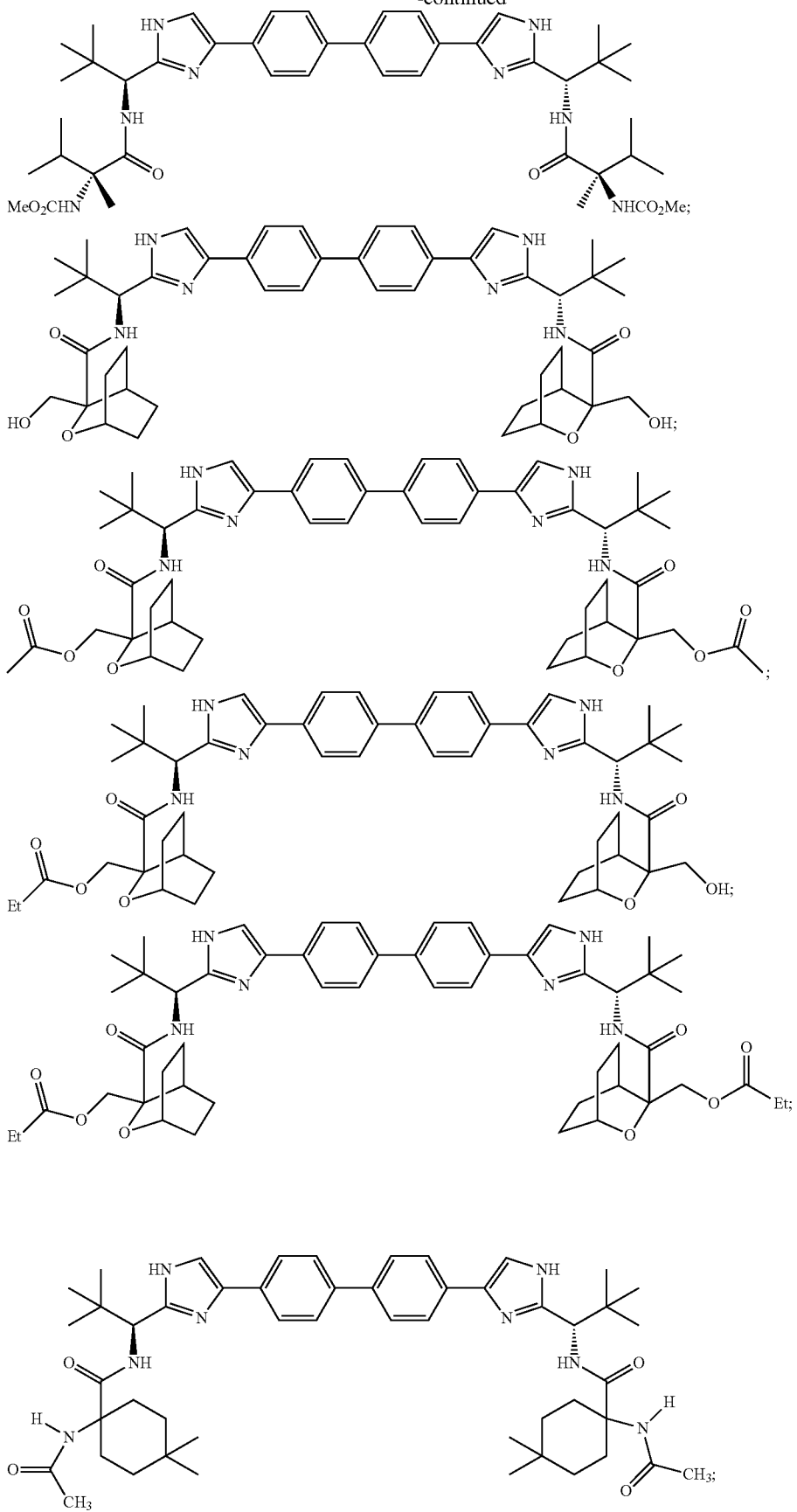

-continued
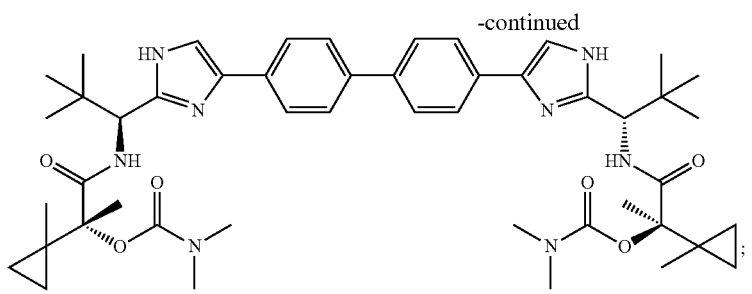
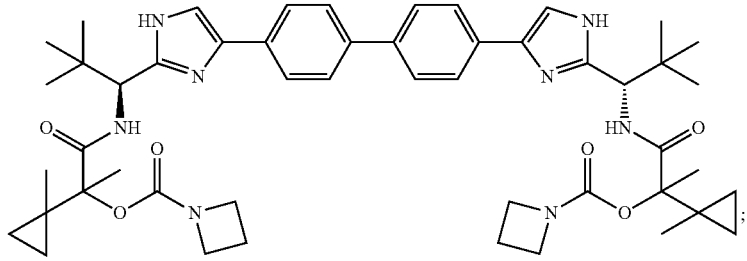
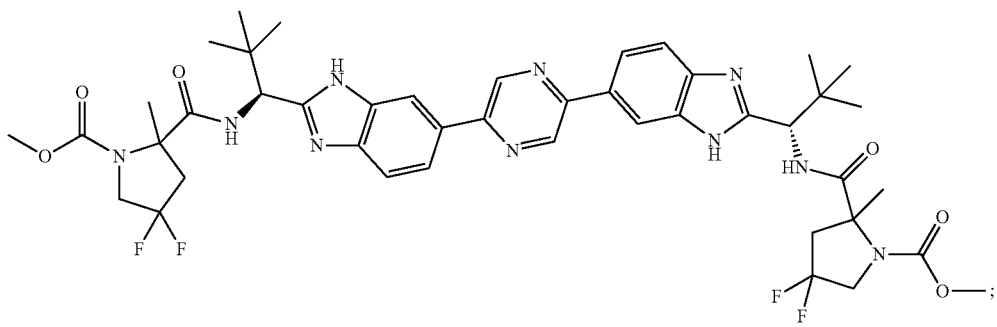
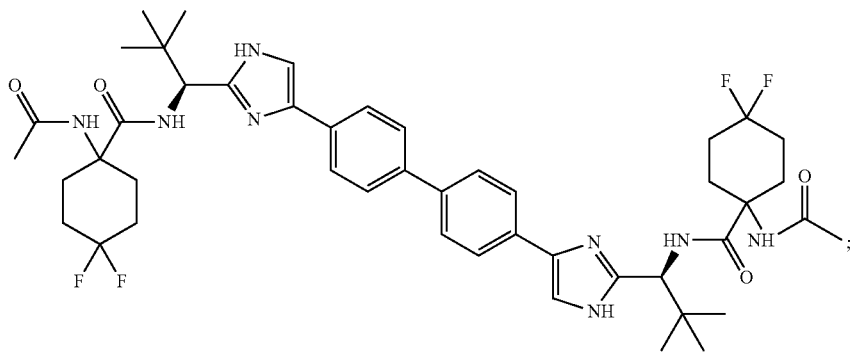
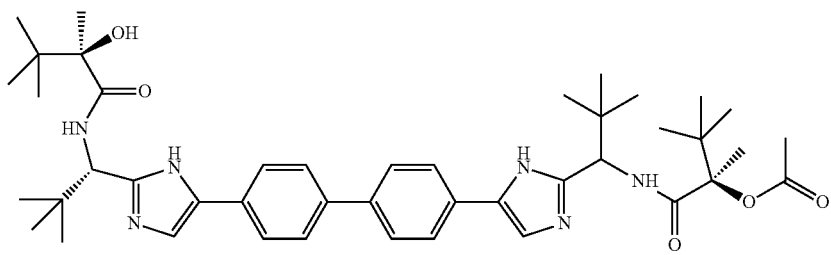

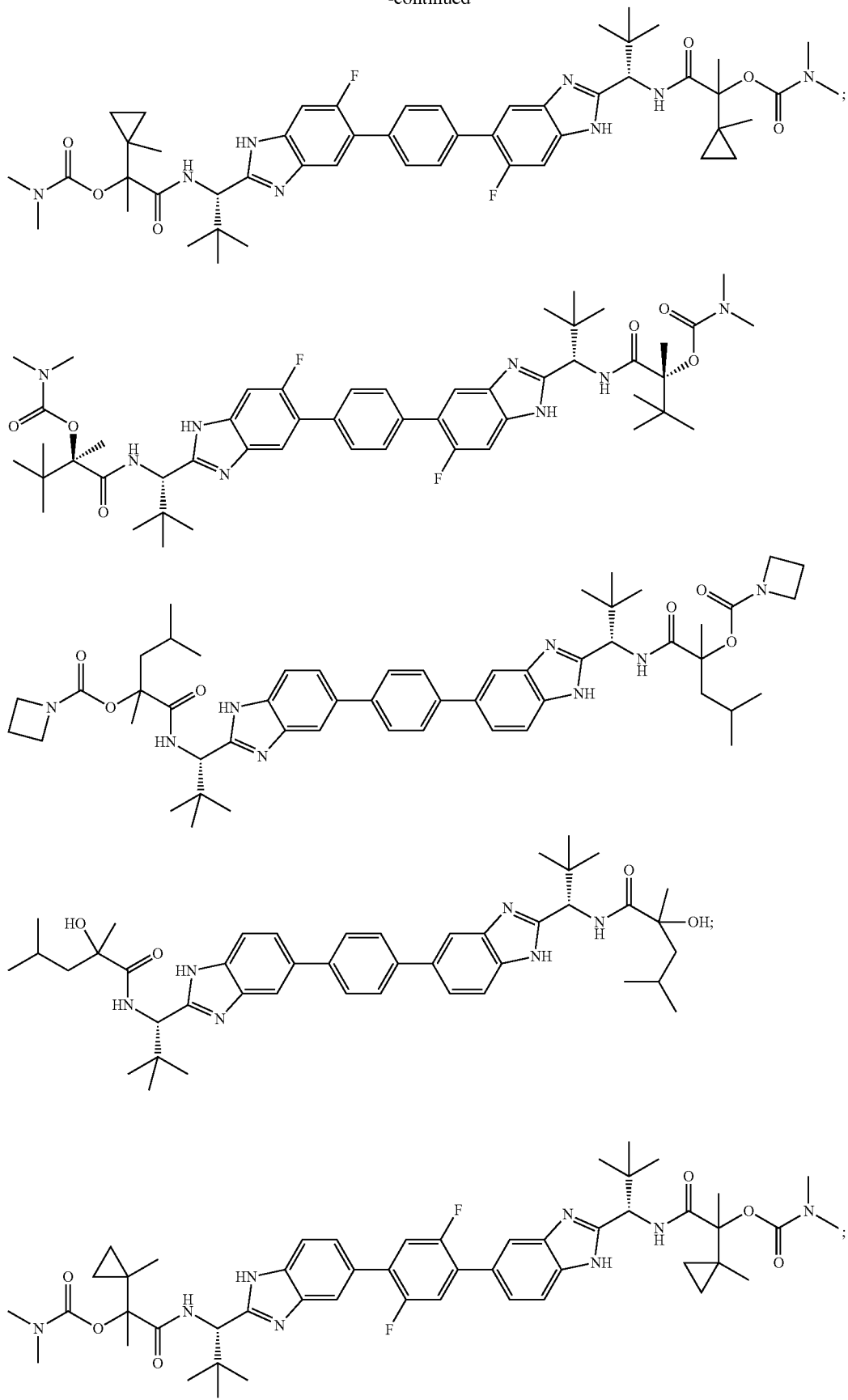

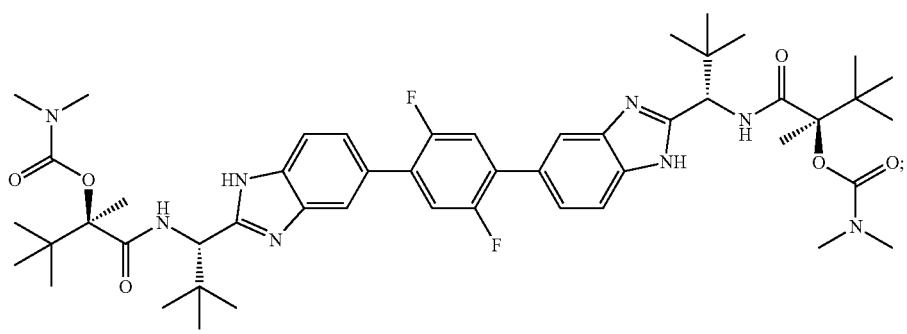
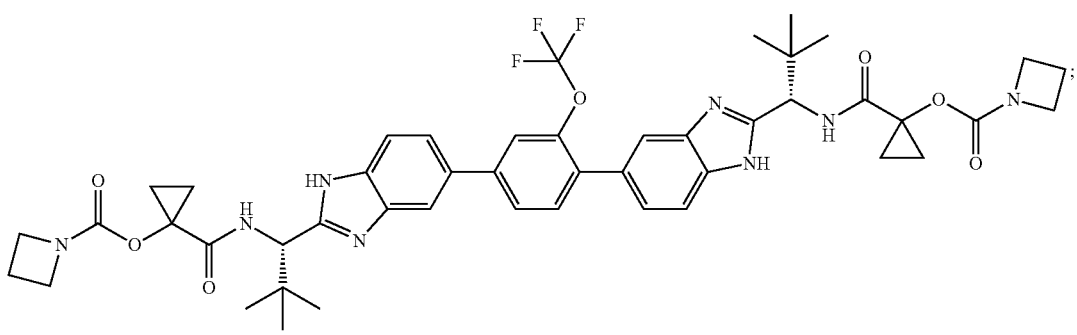
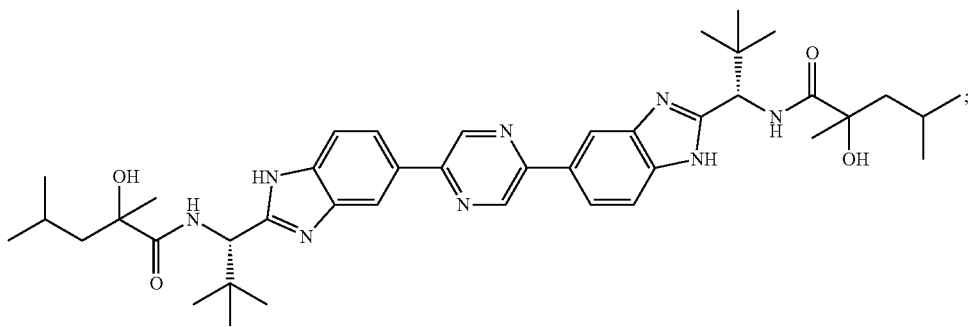
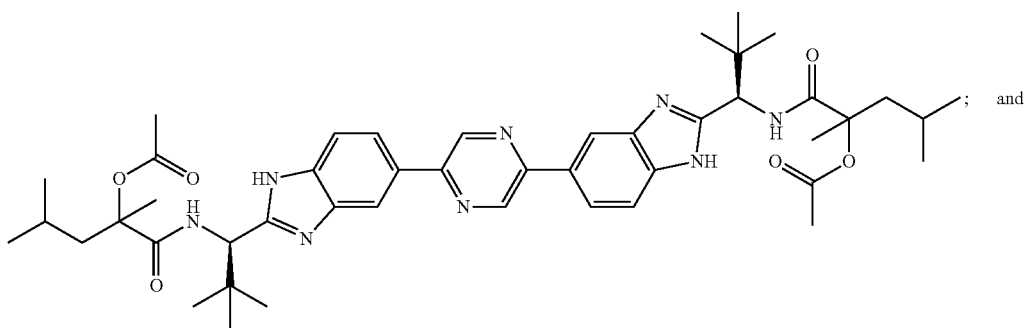

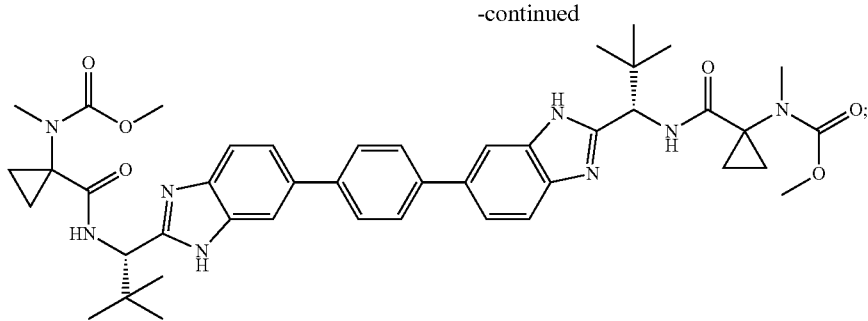

or a pharmaceutically acceptable salt thereof.

In a first embodiment of the first aspect the NS5A-targeting compound is BMS-790052 or a pharmaceutically acceptable salt thereof.

In a second embodiment of the first aspect the present disclosure provides a composition comprising an NS5A-targeting compound and an NS5A synergist selected from the list of compounds shown above, or a pharmaceutically acceptable salt thereof, and one or more pharmaceutically acceptable carriers. In a third embodiment said composition comprises one or two additional compounds having anti-HCV activity. In a fourth embodiment at least one of the additional compounds is an interferon or a ribavirin. In a fifth embodiment the interferon is selected from interferon alpha 2B, pegylated interferon alpha, pegylated interferon lambda, consensus interferon, interferon alpha 2A, and lymphoblastoid interferon tau. In a sixth embodiment said composition comprises one or two additional compounds having anti-HCV activity wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

In a second aspect the present disclosure provides a method of treating an HCV infection in a patient, comprising administering to the patient a therapeutically effective amount of a combination of an NS5A-targeting compound and an NS5A synergist selected from the list of compounds above, or a pharmaceutically acceptable salt thereof. In a first embodiment of the second aspect the method further comprises administering one or two additional compounds having anti-HCV activity prior to, after or simultaneously with the combination, or a pharmaceutically acceptable salt thereof. In a second embodiment at least one of the additional compounds is an interferon or a ribavirin. In a third embodiment the interferon is selected from interferon alpha 2B, pegylated interferon alpha, pegylated interferon lambda, consensus interferon, interferon alpha 2A, and lymphoblastoid interferon tau. In a fourth embodiment at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

As used herein, the term "NS5A synergist" refers to a molecule that alone shows a weaker activity against HCV wild type than the NS5A-targeting compound, but when combined with an NS5A-targeting compound shows a greater than three-fold increase in $EC_{50}$ potency than the potency of the NS5A-targeting compound alone.

As used herein, the term "synergistic anti-HCV activity" refers to a greater than three-fold increase in $EC_{50}$ potency than the potency of the NS5A-targeting compound alone.

As used herein, the term "NS5A-targeting compound", refers to a molecule that inhibits HCV replication for which at least one resistance substitution maps to the NS5A protein and most commonly within, but not limited to, the first 100 residues of NS5A.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace the compounds making up the combination of the present disclosure and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

When it is possible that, for use in therapy, therapeutically effective amounts of each compound of the combination, as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of the compounds comprising the combination or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of the combination and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing the compounds of the combination, or pharmaceutically acceptable salts thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidyl-cholines.

The compounds of the combination and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table A below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE A

| Brand Name | Physiological Class | Type of Inhibitor or Target | Source Company |
|---|---|---|---|
| NIM811 | | Cyclophilin Inhibitor | Novartis |
| Zadaxin | | Immune-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, |

TABLE A-continued

| Brand Name | Physiological Class | Type of Inhibitor or Target | Source Company |
|---|---|---|---|
| | | | MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Sofosbuvir | Antiviral | RdRp inhibitor | Gilead Sciences Inc., Foster City, CA |
| Harvoni ® | Antiviral | RdRp inhibitor + NS5A inhibitor | Gilead Sciences Inc., Foster City, CA |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, |

TABLE A-continued

| Brand Name | Physiological Class | Type of Inhibitor or Target | Source Company |
|---|---|---|---|
| Intron A | Interferon | IFN-α2b | Basel, Switzerland Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |

TABLE A-continued

| Brand Name | Physiological Class | Type of Inhibitor or Target | Source Company |
|---|---|---|---|
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Bristol-Myers Squibb |
| asunaprevir | Antiviral | serine protease inhibitor | Bristol-Myers Squibb |
| IDX-719 | Antiviral | NS5A inhibitor | Idenix |
| GS-5885 | Antiviral | NS5A inhibitor | Gilead |
| GS-5816 | Antiviral | NS5A inhibitor | Gilead |
| ABT-267 | Antiviral | NS5A inhibitor | Abbvie |
| GSK-2336805 | Antiviral | NS5A inhibitor | GlaxoSmithKline |
| PPI-461 | Antiviral | NS5A inhibitor | Presidio |
| EDP-239 | Antiviral | NS5A inhibitor | Enanta |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: FCC for flash column chromatography; TFA for trifluoroacetic acid; min for minutes; MeOH for methanol; NH$_4$OAc for ammonium acetate; ACN or AcCN or MeCN for acetonitrile; THF for tetrahydrofuran; h or hr for hours; EtOAc for ethyl acetate; RT or rt for room temperature or retention time (context will dictate); DCM for dichloromethane; KHMDS for potassium hexamethyldisilazide; DIEA or DiPEA or DIPEA for diisopropylethylamine; Me for methyl; DMAP for 4-(dimethylamino)pyridine; EtOH for ethanol; IPA for isopropyl alcohol; TEA or Et$_3$N for triethylamine; TBAF for tetrabutylammonium fluoride; t-BuOH for tert-butanol; BOC or Boc for tert-butoxycarbonyl; Et for ethyl; LDA for lithium diisopropylamide; TBME for MTBE for methyl tert-butyl ether; DAST for diethylaminosulfur trifluoride; NMO for N-methylmorpholine N-oxide; EDC for 1-ethyl-3-(3-dimethylaminopropyl)carbodiimide hydrochloride; dppf for 1,1'-bis(diphenylphosphino)ferrocene; HATU for O-(7-azabenzotriazole-1-yl)-1,1,3,3-tetramethyluronium hexafluorophosphate; HOAT or HOAt for 1-hydroxy-7-azabenzotriazole; EDCI or EDC for 1-ethyl-3-(3-dimethylaminopropyl)carbodiimide; DMF for N,N-dimethylformamide; TBTU for O-(benzotriazol-1-yl)-N,N,N',N'-tetramethyluronium tetrafluoroborate; Ac or AC for acetyl; and NMM for N-methylmorpholine.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what was believed to be the most useful and readily understood description of its procedures and conceptual aspects.

Starting materials can be obtained from commercial sources or prepared by well-established literature methods known to those of ordinary skill in the art.

Lc-Ms Conditions:
Condition 1:
Column=Phenomenex-Luna, 2.0×50 mm, 3 μm
Start % B=0; Final % B=100
Gradient time=4 min
Flow Rate=0.8 mL/min
Wavelength=220 nm
Solvent A=0.1% TFA in 10% methanol/90% water
Solvent B=0.1% TFA in 90% methanol/10% water
Oven temp.=40° C.
Condition 1a:
Column=Phenomenex-Luna, 2.0×50 mm, 3 μm
Start % B=30; Final % B=100
Gradient time=4 min
Flow Rate=0.8 mL/min
Wavelength=220 nm
Solvent A=0.1% TFA in 10% methanol/90% water
Solvent B=0.1% TFA in 90% methanol/10% water
Oven temp.=40° C.
Condition 1b:
Column=Phenomenex 2.0×30 mm, 3 μm
Start % B=0; Final % B=100
Gradient Time=3 min
Flow Rate=0.8 mL/min; Wavelength=220 nm
Solvent A=0.1% TFA in 10% MeOH:90% $H_2O$
Solvent B=0.1% TFA in 90% MeOH:10% $H_2O$
Oven temp.=40° C.
Condition 1c:
Column=Phenomenex, 2.0×50 mm, 3 μm
Start % B=0; Final % B=100
Gradient time=4 min; Stop time=5 min
Flow Rate=0.8 mL/min; Wavelength=220 nm
Solvent A=0.1% TFA in 10% $CH_3CN$/90% water
Solvent B=0.1% TFA in 90% $CH_3CN$/10% water
Oven temp.=40° C.
Condition 1d:
Column=Phenomenex Luna C18, 2.0×30 mm, 3 μm
Start % B=0; Final % B=100
Gradient time=3 min; Stop time=3 min
Flow Rate=1 mL/min; Wavelength=220 nm
Solvent A=0.1% TFA in 10% $CH_3CN$/90% water
Solvent B=0.1% TFA in 90% $CH_3CN$/10% water
Oven temp.=40° C.
Condition 2:
Column=Waters BEH C18, 2.0×50 mm, 1.7 μm particles
Gradient=0.5 min hold at 0% B, 0-100% B over 4 min, then 0.5 min hold at 100% B
Flow Rate=1 mL/min
Solvent A=5:95 $CH_3CN$:$H_2O$ with 10 mM $NH_4OAc$
Solvent B=95:5 $CH_3CN$:$H_2O$ with 10 mM $NH_4OAc$
Temperature=50° C.
Condition 3:
Column=Waters BEH C18, 2.0×50 mm, 1.7 μm particles
Gradient=0.5 min hold at 0% B, 0-100% B over 3 min, then a 0.5-min hold at 100% B;
Flow rate=0.5 mL/min
Wavelength=220 nm
Solvent A=5:95 MeOH:$H_2O$ with 10 mM $NH_4OAc$
Solvent B=95:5 MeOH:$H_2O$ with 10 mM $NH_4OAc$
Temperature=50° C.
Condition 4:
Column=Phenomenex, Waters Aquity BEH C18 2.1×50 mm, 1.7 μm
Start % B=2; Final % B=98
Gradient time=1.5 min; Stop time=2 min
Flow Rate=0.8 mL/min; Wavelength=220 nm
Solvent A=0.1% TFA in 10% methanol/90% water
Solvent B=0.1% TFA in 90% methanol/10% water
Oven temp.=40° C.
Condition 5:
Column=Waters BEH C18, 2.0×50 mm, 1.7 μm
Start % B=0; Final % B=100
Gradient time=3 min; Stop time=3.5 min
Flow Rate=1 mL/min; Wavelengths=220 nm
Solvent A=10 mM $NH_4OAc$ in 5% $CH_3CN$/95% water
Solvent B=10 mM $NH_4OAc$ in 95% $CH_3CN$/5% water
Condition 6:
Column=Waters BEH C18, 2.1×50 mm, 1.7 μm
Start % B=0; Final % B=100
Gradient time=3 min; Stop time=3.5 min
Flow Rate=1 mL/min; Wavelength=220 nm
Solvent A=10 mM $NH_4OAc$ in 5% $CH_3CN$/95% water
Solvent B=10 mM $NH_4OAc$ in 95% $CH_3CN$/5% water
Oven temp.=50° C.
Condition 7:
Column=Ascentis Express C18, 2.1×50 mm, 2.7 um
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient
time=1.4 min; Stop time=4 min
Stop time=4 min
Flow Rate=1 mL/min; Wavelength=220 nm
Condition 8:
Column=Ascentis Express C8, 2.1×50 mm, 2.7 um
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient
time=1.5 min; Stop time=4 min
Isocratic time=1.7 min
Flow Rate=1 mL/min; Wavelength=220 nm
Condition 9:
Column=Ascentis Express C8, 2.1×50 mm, 2.7 um
Solvent A=$CH_3CN$ (10%)+10 mM $NH_4COOH$ in $H_2O$ (90%)
Solvent B=$CH_3CN$ (90%)+10 mM $NH_4COOH$ in $H_2O$ (10%)
Start % B=0; Final % B=100
Gradient
time=1.6 min; Stop time=4 min
Isocratic time=1.6 min
Flow Rate=1 mL/min; Wavelength=220 nm
Condition 10:
Column=Ascentis Express C8, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient
time=1.5 min; Stop time=4 min
Isocratic time=1.7 min
Flow Rate=1 mL/min; Wavelength=220 nm

Acid 1

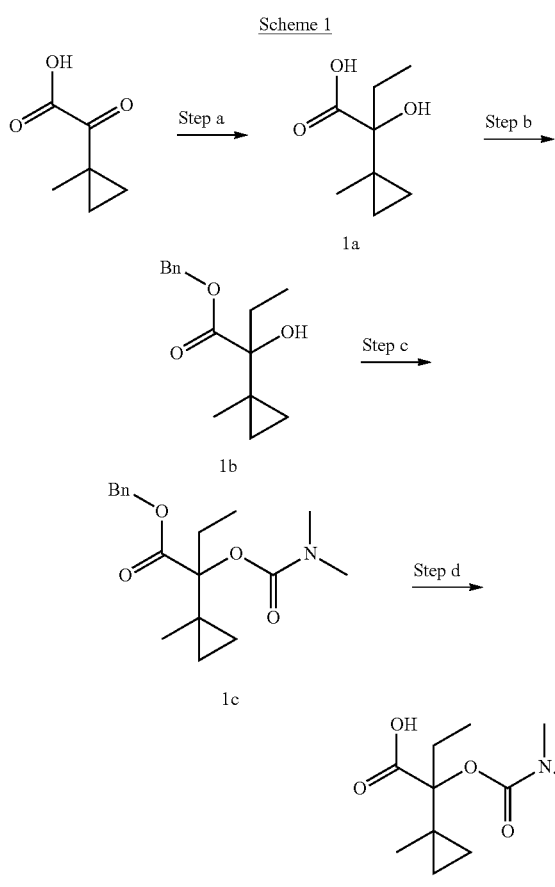

Step a:

To a solution of 2-(1-methylcyclopropyl)-2-oxoacetic acid (1.0 g, 7.80 mmol) in THF (40 mL) was added ethylmagnesium chloride (2.0 M in THF; 8.59 mL, 17.17 mmol) drop wise at 0° C. The resulting solution was then slowly warmed to RT and stirred for 16 h. The reaction mixture was then cooled to 0° C. and quenched with 1N HCl. The aqueous phase was extracted with EtOAc. The combined organic layers were washed with brine, dried (Na$_2$SO$_4$), and concentrated to yield acid 1a (1.2 g).

Step b:

To a solution of acid 1a (1.2 g, 7.59 mmol) in DCM (15 mL) was added DIPEA (1.590 mL, 9.10 mmol), benzyl bromide (0.902 mL, 7.59 mmol) and DMAP (0.051 g, 0.417 mmol). The reaction mixture was stirred at RT for 18 h. The reaction mixture was diluted with EtOAc and washed with satd. NaHCO$_3$, water, brine, dried (Na$_2$SO$_4$), and purified by silica gel chromatography (80 g, 0-40% EtOAc/hex) to yield ester 1b (0.19 g). LC/MS (Condition 1): R$_t$=3.81 min, [M+Na]$^+$ 271.10.

Step c:

A solution of KHMDS in THF (1.0 M; 0.92 mL, 0.92 mmol) was added to a cold (−78° C.) solution of ester 1b (0.19 g, 0.765 mmol) in THF (5 mL) and the mixture was stirred at −78° C. for 30 min. Then dimethylcarbamic chloride (0.084 mL, 0.918 mmol) was added and the reaction mixture was stirred at −78° C. for 5 min, then warmed to RT and stirred at RT for 2 h. The reaction mixture was diluted with EtOAc, washed with 1 N HCl, satd. NaHCO$_3$, water, brine and dried (Na$_2$SO$_4$), and concentrated in vacuo. The resultant crude product was purified by flash chromatography (80 g silica gel; 0-40% EtOAc/hex) to afford ester 1c (0.18 g). $^1$H NMR (400 MHz, CDCl$_3$) δ 7.42-7.27 (m, 5H), 5.29-5.07 (m, 2H), 2.88-2.82 (m, 6H), 2.51 (dq, J=15.2, 7.5 Hz, 1H), 2.25 (dq, J=15.2, 7.5 Hz, 1H), 1.05-0.95 (m, 5H), 0.91 (t, J=7.5 Hz, 3H), 0.42-0.29 (m, 1H), 0.21-0.02 (m, 1H). LC/MS (Condition 1): R$_t$=3.99 min, [M+14]$^+$ 320.15.

Step d:

To a solution of ester 1c (0.18 g, 0.564 mmol) in EtOAc (10 mL) was added 10% Pd/C (0.060 g) and the mixture was stirred at RT for 1 h. Then it was filtered through a plug of Celite, washed with EtOAc and concentrated to yield acid 1 (0.116 g) as a white solid. LC/MS (Condition 1): R$_t$=3.30 min, [M+H]$^+$ 230.15.

Acid 2

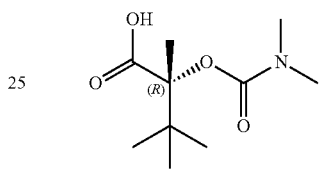

Acid 2 was prepared from (R)-2-hydroxy-2,3,3-trimethylbutanoic acid according to the procedure described for the preparation of acid 1.

Acid 3

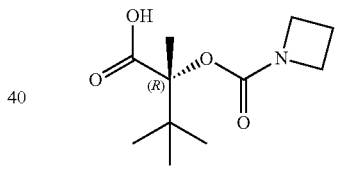

Acid 3 was prepared from (R)-2-hydroxy-2,3,3-trimethylbutanoic acid and azetidine according to the procedure described for the preparation of acid 1. NMR (400 MHz, MeOH-d$_4$) δ 4.66-4.48 (m, 1H), 4.16-4.07 (m, 1H), 4.06-3.91 (m, 2H), 2.32-2.15 (m, 2H), 1.35-1.29 (m, 3H), 1.03-0.97 (m, 9H). LC/MS (Condition 1): R$_t$=3.37 min, [M+H]$^+$ 230.15.

Acid 4

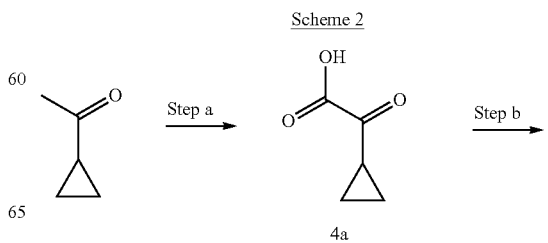

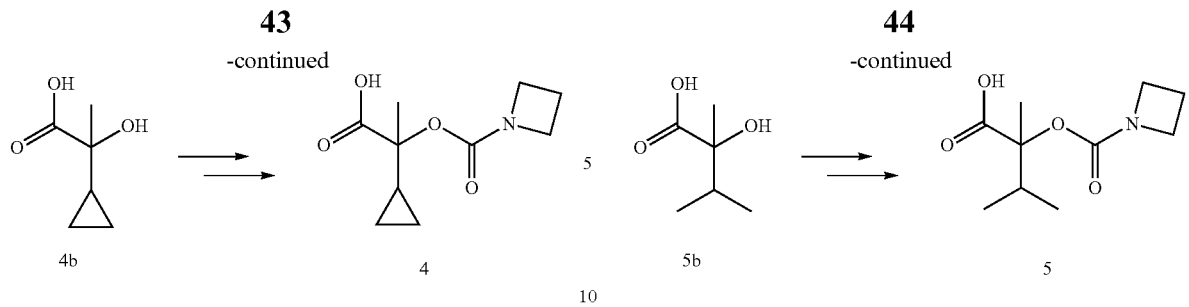

Step a:

To a mixture of 1-cyclopropylethanone (5.0 g, 59.4 mmol), NaOH (4.99 g, 125 mmol) in water (120 mL) at −4° C. was added potassium permanganate (18.79 g, 119 mmol) portion wise with vigorous stirring. The inner temperature was maintained between −3 to 1° C. during the addition process. The reaction mixture was warmed to RT and stirred for 16 h. To the reaction mixture was added EtOH (20 mL) and the mixture was stirred for 15 min. It was then filtered to remove the solid and washed with water. The filtration was acidified with 12 N HCl at 0° C., extracted with EtOAc (2×). The combined extract was washed with brine, dried (Na$_2$SO$_4$) and concentrated to afford acid 4a (6.0 g). $^1$H NMR (400 MHz, CDCl$_3$) δ 7.69-7.40 (m, 1H), 2.95 (tt, J=7.6, 4.8 Hz, 1H), 1.42-1.22 (m, 4H).

Step b:

To a solution of acid 4a (3.0 g, 26.3 mmol) in THF (40 mL) was added MeMgCl (3 M in THF; 19.3 mL, 57.8 mmol) drop-wise at 0° C. The resulting solution was then stirred at RT for 24 h. The reaction mixture was then cooled to 0° C. and quenched with 1 N HCl (100 mL). The aqueous phase was extracted with EtOAc (2×150 mL). The combined organic layer was washed with brine, dried (Na$_2$SO$_4$), and concentrated to yield alcohol 4b (3.0 g). $^1$H NMR (400 MHz, CDCl$_3$) δ 1.50 (s, 3H), 1.30-1.19 (m, 1H), 0.60-0.32 (m, 4H).

Final Steps:

Acid 4 was prepared from alcohol 4b and azetidine according to the procedure described for the preparation of acid 1. $^1$H NMR (400 MHz, MeOH-d$_4$) δ 4.17-3.87 (m, 4H), 2.26 (m, 2H), 1.53 (s, 3H), 1.38-1.23 (m, 1H), 0.66-0.58 (m, 1H), 0.57-0.39 (m, 3H). LC/MS (Condition 1): R$_t$=2.86 min, [M+H]$^+$ 214.05.

Acid 5

Step a:

To a solution of 3-methylbutan-2-one (2.491 mL, 23.22 mmol) in DCM (25 mL) under nitrogen at RT was added trimethylsilyl cyanide (6.23 mL, 46.4 mmol) followed by the addition of zinc iodide (7.41 g, 23.22 mmol). The reaction was stirred at RT for 18 h. It was then diluted with EtOAc and 1 N NaOH, and the solid was filtered. The filtrate was washed with satd. NaCl, dried over anhydrous Na$_2$SO$_4$, and concentrated to yield silyl ether 5a (4 g), which was advanced to the next step without purification. $^1$H NMR (400 MHz, CDCl$_3$) δ 1.86 (dt, J=13.5, 6.7 Hz, 1H), 1.57-1.48 (m, 3H), 1.08-0.97 (m, 6H), 0.30-0.15 (m, 9H).

Step b:

A solution of crude 5a (4 g) in concentrated HCl (37%, aq) was heated at 80° C. for 23 h and then cooled to RT. The reaction was diluted with water, extracted with diethyl ether (3×100 mL). The combined organic layer was washed with brine, dried (Na$_2$SO$_4$), and concentrated to afford hydroxyacid 5b (0.85 g). $^1$H NMR (400 MHz, CDCl$_3$) δ 2.11-1.95 (m, 1H), 1.46 (s, 3H), 1.06-0.98 (m, 3H), 0.98-0.91 (m, 3H).

Final Steps:

Acid 5 was prepared from hydroxyacid 5b according to the procedure described for the preparation acid 1. $^1$H NMR (400 MHz, MeOH-d$_4$) δ ppm 4.15-4.05 (m, 1H), 4.05-3.88 (m, 3H), 2.34-2.21 (m, 2H), 2.11-1.99 (m, 1H), 1.56-1.48 (m, 3H), 1.04-0.97 (m, 3H), 0.97-0.90 (m, 3H). LC/MS (Condition 1): R$_t$=3.13 min, [M+H]$^+$ 216.1.

Acid 6

Scheme 3

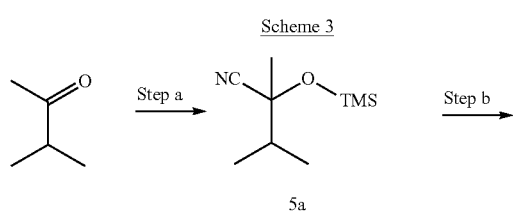

Scheme 4

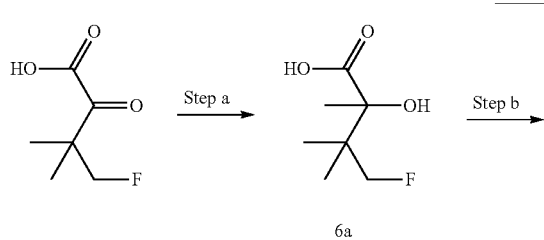

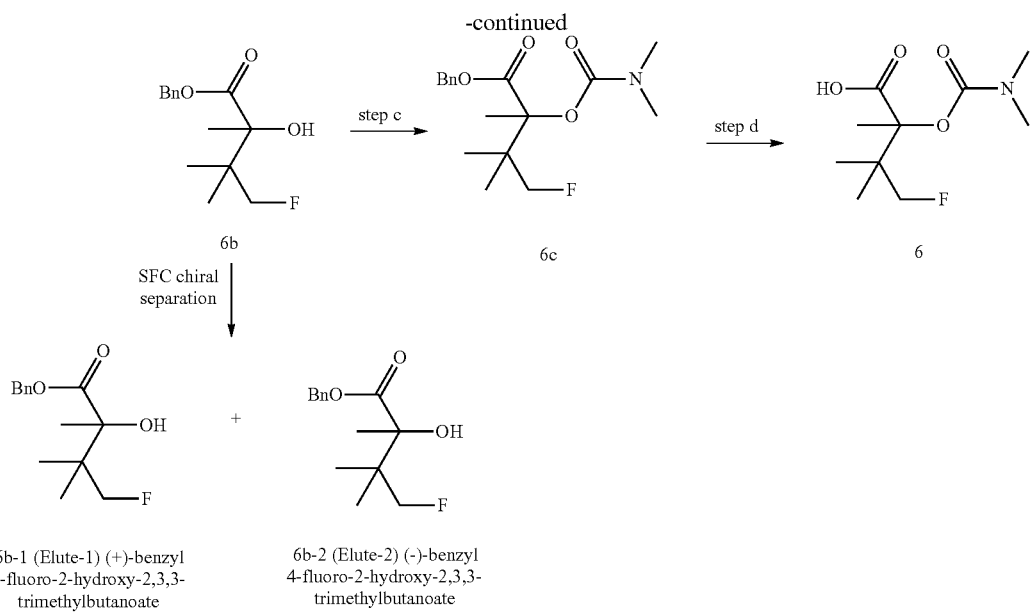

6b

SFC chiral separation

6c

6

6b-1 (Elute-1) (+)-benzyl 4-fluoro-2-hydroxy-2,3,3-trimethylbutanoate 6b-2 (Elute-2) (-)-benzyl 4-fluoro-2-hydroxy-2,3,3-trimethylbutanoate Step a:

MeMgBr (27.0 mL, 81.0 mmol) was added drop-wise to a solution of 4-fluoro-3,3-dimethyl-2-oxobutanoic acid (4.0 g, 27 mmol) in THF (40 mL) at 0° C. The resulting solution was stirred at RT for 24 h and quenched with satd. NH$_4$Cl (10 ml) at 0° C., followed by acidification with 2 N HCl. The organic layer was separated and the aqueous layer was re-extracted with EtOAc (4×). The combined organic extracts was washed with brine, dried (MgSO$_4$), and concentrated in vacuo to afford hydroxyacid 6a.

Step b:

To crude hydroxyacid 6a in acetonitrile (40 mL), DIEA (5.66 mL, 32.4 mmol) and (bromomethyl)benzene (3.85 mL, 32.4 mmol) were added. The mixture was stirred at RT for 18 h, diluted with EtOAc, washed with water, dried (MgSO$_4$). The volatile component was removed in vacuo and the resultant crude material was purified by silica gel flash chromatography (0-50% EtOAc/hexanes) to afford ester 6b (2.4 g). $^1$H NMR (400 MHz, CDCl$_3$) δ 7.45-7.35 (m, 5H), 5.28-5.24 (m, 1H), 5.23-5.19 (m, 1H), 4.46-4.17 (m, 2H), 1.43 (s, 3H), 1.04 (d, J=1.8 Hz, 3H), 1.02 (d, J=2.3 Hz, 3H).

Step c:

A solution of KHMDS (1 M, 0.57 mL, 0.57 mmol) in THF was added to a cold (−78° C.) solution of racemic ester 6b (0.145 g, 0.570 mmol) in THF (5 mL) and the mixture was stirred at −78° C. for 30 min. Neat dimethylcarbamic chloride (0.078 mL, 0.855 mmol) was added and the mixture was allowed to warm to RT overnight. Reaction mixture was diluted with ether (25 ml) and quenched with satd. NH$_4$Cl. Organic layer was separated and washed with water, brine and dried (MgSO$_4$). Crude isolate was purified by silica gel FCC (5% EtOAc in DCM) to afford carbamate 6c (0.14 g) as clear oil. $^1$H NMR (400 MHz, CDCl$_3$) δ 7.41-7.31 (m, 5H), 5.22-5.17 (m, 1H), 5.17-5.11 (m, 1H), 4.46-4.36 (m, 1H), 4.34-4.24 (m, 1H), 2.93 (s, 3H), 2.89 (s, 3H), 1.73 (d, J=1.0 Hz, 3H), 1.08 (d, J=2.0 Hz, 3H), 1.04 (d, J=2.0 Hz, 3H).

Step d:

A solution of carbamate 6c (0.07 g, 0.215 mmol) in EtOAc (5 mL) was degassed and purged with N$_2$ and 10% Pd/C (15 mg) was added and degassed and refilled with H$_2$. The reaction mixture was hydrogenated under balloon pressure for 45 min, filtered and concentrated to dryness to afford acid 6 (0.051 g). $^1$H NMR (400 MHz, CDCl$_3$) δ 4.53-4.43 (m, 1H), 4.40-4.31 (m, 1H), 2.97 (s, 3H), 2.96-2.91 (m, 3H), 1.71 (d, J=1.0 Hz, 3H), 1.13 (d, J=2.0 Hz, 3H), 1.11 (d, J=2.3 Hz, 3H).

Resolution of Ester 6b:

Racemate 6b was resolved on Lux Cellulose-2, 21×250 mm, 5 μm (mobile Phase: 5% Hept:IPA (9:1)/95% CO$_2$) to afford the optically pure enantiomers. Based on optical rotation study, elute-1 was assigned (+)-benzyl 4-fluoro-2-hydroxy-2,3,3-trimethylbutanoate and the elute-2 was assigned (−)-benzyl 4-fluoro-2-hydroxy-2,3,3-trimethylbutanoate. Using the protocols noted for the racemate, each isomer was advanced to the individual enantiomers of acid 6.

Acid 7

Scheme 5

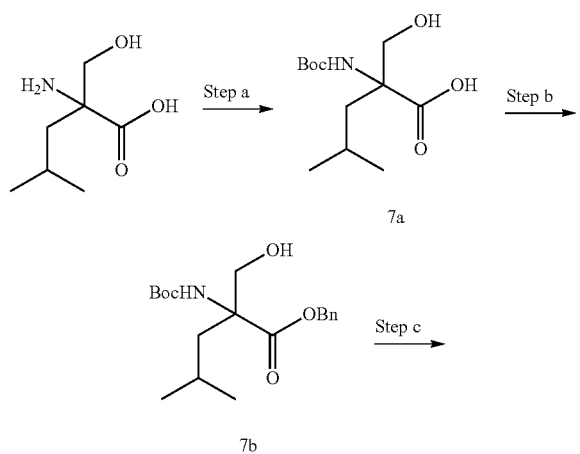

7a

7b

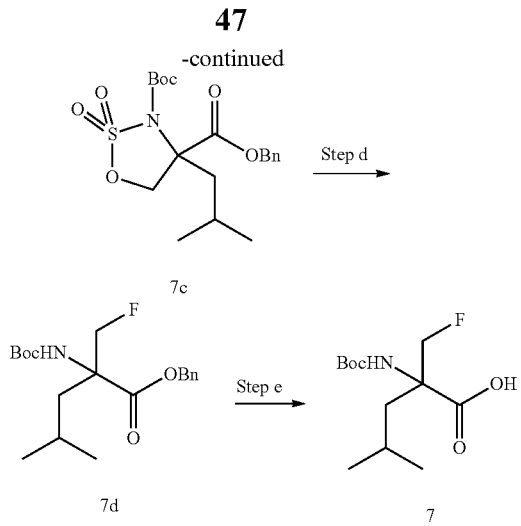

Step a:

To a mixture of 2-amino-2-(hydroxymethyl)-4-methyl-pentanoic acid (1.6 g, 9.93 mmol) in MeOH (18 mL) was added 1 N sodium hydroxide (20 mL, 20 mmol), stirred until a uniform solution was formed, cooled with ice-water bath, and then treated with (Boc)$_2$O (4.4 g, 19.85 mmol). The mixture was stirred at RT for overnight, diluted with EtOAc and washed with ice-cold 1 N HCl (2×), brine, and dried (MgSO$_4$). Removal of the solvent afforded carbamate 7a (2.5 g). $^1$H NMR (400 MHz, CDCl$_3$) δ 1.81-1.62 (m, 3H), 1.48 (s, 9H), 0.97 (s, 3H), 0.92 (d, J=6.5 Hz, 3H).

Step b:

To a solution of carbamate 7a (0.7 g, 2.68 mmol) in DCM (10 mL) were added DIPEA (0.6 mL, 3.44 mmol) and benzylbromide (0.4 mL, 3.36 mmol) at 0° C. The reaction mixture was stirred at RT for 4 days. The reaction mixture was diluted with EtOAc, washed with satd. aq. NH$_4$Cl and brine, concentrated in vacuo, and purified by silica gel chromatography (0-50% EtOAc/Hexanes) to afford ester 7b (0.76 g). $^1$H NMR (400 MHz, CDCl$_3$) δ 7.43-7.33 (m, 5H), 5.67 (br. s., 1H), 4.21-4.10 (m, 1H), 3.88-3.69 (m, 1H), 2.95 (br. s., 1H), 2.14 (d, J=10.0 Hz, 1H), 1.74-1.58 (m, 2H), 1.46 (s, 9H), 0.92 (d, J=6.4 Hz, 3H), 0.78 (d, J=6.4 Hz, 3H).

Step c:

To a solution of ester 7b (0.25 g, 0.711 mmol) and TEA (0.4 mL, 2.87 mmol) in DCM (5 mL) was added a solution of thionyl chloride (0.08 mL, 1.096 mmol) in DCM (5 mL) at −78° C. The reaction mixture was stirred at −78° C. for 3 h, the cooling bath was removed, stirring continued at RT for 0.5 h. The solvent was removed under vacuum. To the resultant crude product were added acetonitrile (20 mL) and water (5 mL). The mixture was cooled in ice-water bath, ruthenium(III) chloride/H$_2$O (0.007 ml, 0.031 µmol) and sodium periodate (0.61 g, 2.85 mmol) were added. The mixture was stirred in ice-water bath for 0.5 h and at RT for 0.5 h. It was then diluted with EtOAc, washed with water, aq. NaHCO$_3$, brine, and dried (MgSO$_4$) and concentrated in vacuo. The resultant crude material was purified by silica gel chromatography (EtOAc/hexanes) to afford ester 7c (0.22 g). $^1$H NMR (400 MHz, MeOH-d$_4$) δ 7.47-7.32 (m, 5H), 5.51 (s, 1H), 5.26 (s, 2H), 4.67 (s, 1H), 2.33-2.17 (m, 1H), 2.02-1.78 (m, 2H), 1.52-1.34 (m, 9H), 1.04 (d, J=6.6 Hz, 3H), 1.00 (d, J=6.6 Hz, 3H).

Step d:

To a solution of ester 7c (0.22 g, 0.532 mmol) in THF (4 ml) was added TBAF/(t-BuOH)$_4$ (0.49 g, 0.878 mmol) at 0° C. The mixture was warmed to RT and stirred for 20 h.

Another portion of TBAF/(t-BuOH)$_4$ (0.49 g, 0.878 mmol) was added and stirring continued for 3 days. EtOAc was added and the mixture was stirred for 10 min. It was then washed with water and brine, dried (MgSO$_4$) and concentrated in vacuo. The resultant crude material was purified on a silica gel column (0-30% EtOAc/hexanes) to afford fluoride 7d (0.16 g). $^1$H NMR (500 MHz, CDCl$_3$) δ 7.43-7.34 (m, 5H), 5.66 (br. s., 1H), 5.24 (s, 2H), 5.08-4.91 (m, 1H), 4.68-4.48 (m, 1H), 2.19-2.06 (m, 1H), 1.69-1.58 (m, 2H), 1.46 (s, 9H), 0.91 (d, J=6.7 Hz, 3H), 0.81-0.73 (m, 3H).

Step e:

A mixture of fluoride 7d (0.16 g, 0.453 mmol) in THF (4 mL), MeOH (2 mL) and sodium hydroxide (2 mL of 1 N, 2 mmol) was stirred at RT for 20 h. The reaction mixture was concentrated and extracted with ether/hexane (1/1). The aqueous solution was diluted with EtOAc and washed with cold 1 N HCl and brine, dried (MgSO$_4$). Removal of the solvent afforded acid 7 as viscous oil (76 mg). $^1$H NMR (500 MHz, CDCl$_3$) δ 5.07-4.87 (m, 1H), 4.65-4.49 (m, 1H), 2.13-2.04 (m, 1H), 1.75-1.66 (m, 1H), 1.64-1.54 (m, J=7.2 Hz, 1H), 1.46 (br. s., 9H), 0.95 (d, J=6.7 Hz, 3H), 0.89 (d, J=6.6 Hz, 3H).

Acid 8

Scheme 6

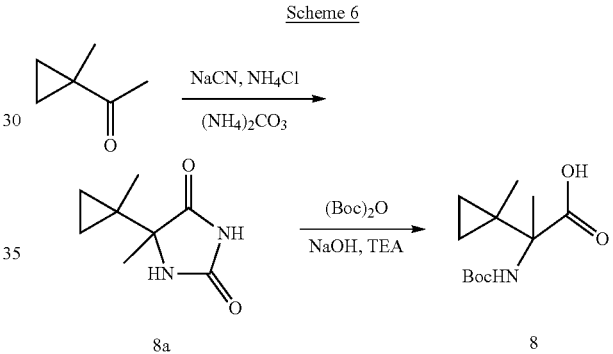

Step a:

To a solution of ammonium chloride (5.45 g, 102 mmol) and ammonium carbonate (9.79 g, 102 mmol) in water (60 mL) was added a solution of 1-(1-methylcyclopropyl)ethanone (2.0 g, 20.4 mmol) in MeOH (40 mL) at RT. The mixture was stirred for 0.5 h before the addition of sodium cyanide (3 g, 61.2 mmol). The reaction mixture was heated in a 65° C. bath for 20 h, cooled down and diluted with water. The mixture was extracted with EtOAc (2×). The combined organic solution was washed with water, brine, dried (MgSO$_4$), and concentrated to afford crude hydantoin 8a (2.1 g). $^1$H NMR (400 MHz, CDCl$_3$) δ 1.41 (s, 3H), 1.18 (s, 3H), 0.75 (dt, J=9.9, 5.0 Hz, 1H), 0.61 (dt, J=10.0, 5.0 Hz, 1H), 0.45-0.37 (m, 1H), 0.36-0.27 (m, 1H).

Step b:

To a mixture of hydantoin 8a (2.1 g, 12.49 mmol) in water (40 mL) was added sodium hydroxide (4.99 g, 125 mmol) and the mixture was heated with a 100° C. bath for 4 days. It was then cooled down to ambient temperature and its pH was adjusted to 9-10 with concentrated HCl. Water was partially removed from the mixture under vacuum and the residue was treated with MeOH, and the solid was filtered off. TEA (1.74 mL, 12.49 mmol), Boc$_2$O (3.0 g, 13.8 mmol) were added to the filtrate and the mixture was stirred for one day at RT. It was partially concentrated and the residue was washed with ether (3×). The aqueous layer was acidified with cold 1 N HCl to pH ~2 and extracted with EtOAc (2×).

The combined EtOAc solution was washed with cold 1 N HCl, brine, dried (MgSO₄), and concentrated in vacuo to afford acid 8 (1.9 g). ¹H NMR (400 MHz, CDCl₃) δ 1.51 (s, 3H), 1.45 (s, 9H), 1.12 (s, 3H), 0.85-0.79 (m, 2H), 0.39-0.34 (m, 2H).

Acid 9b.1 or 9b.2

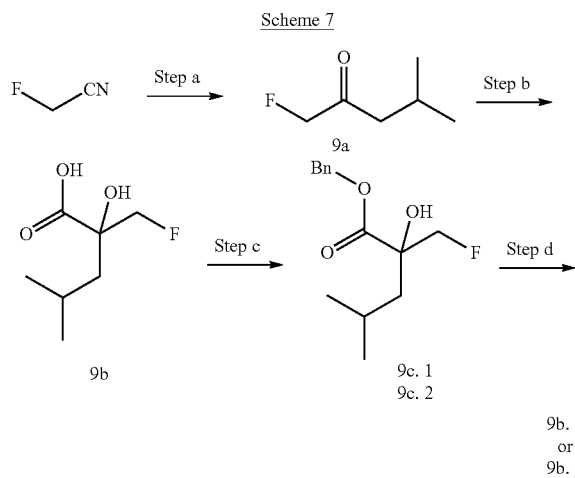

Scheme 7

9b.1 or 9b.2

Step a:

To a solution of 2-fluoroacetonitrile (5 g, 85 mmol) in diethyl ether (400 mL) under nitrogen at 0° C. was added isobutylmagnesium chloride (2M in diethyl ether; 46.6 mL, 93 mmol) dropwise over 15 min. The reaction was maintained stirring at 0° C. under nitrogen for 4 h. The reaction was quenched with water (200 mL), which was thoroughly flushed with nitrogen, and 1M HCl (aq, 100 mL). The layers were separated and the aqueous layer was extracted further with diethyl ether (2×100 mL). The combined organic layers was washed with brine (100 mL), dried (MgSO₄) and concentrated in vacuo to afford a light orange oil (6.4 g). ¹H NMR indicated that the product is a mixture of ketone 9a and isopropanol in a 1.0:0.1 mole ratio. The product was used without further purification. ¹H NMR (400 MHz, CDCl₃) δ 4.77 (d, J=47.9 Hz, 2H), 2.41 (dd, J=6.9, 2.9 Hz, 2H), 2.29-2.11 (m, 1H), 0.96 (d, J=6.5 Hz, 6H). ¹⁹F NMR (376 MHz, CDCl₃) δ -226.87 (t, J=49.5 Hz, 1F).

Step b:

To a solution of crude 9a (4 g, ~33.9 mmol) in CH₂Cl₂ (170 mL) was added trimethylsilyl cyanide (10 mL, 74.6 mmol) followed by zinc iodide (10.81 g, 33.9 mmol). The reaction was stirred under nitrogen at -25° C. for 20.5 h. The reaction was filtered and concentrated in vacuo to remove volatile components. The residue was then taken up in HCl (37%, aq, 250 mL) and heated at 80° C. for 23 h, cooled to RT, and extracted with diethyl ether (3×150 mL). The combined organic layers was washed with brine (100 mL), dried (MgSO₄), and concentrated in vacuo to afford acid 9b as viscous dark brown oil which solidified upon standing (4.78 g). The product was used without further purification. ¹H NMR (400 MHz, CDCl₃) δ 7.62 (br s, 1H), 4.55 (dd, J=91.2, 9.2 Hz, 1H), 4.43 (dd, J=91.2, 9.2 Hz, 1H), 2.02-1.80 (m, 1H), 1.74-1.63 (m, 1H), 1.63-1.51 (m, 1H), 0.99 (d, J=6.5 Hz, 3H), 0.92 (d, J=6.5 Hz, 3H). ¹⁹F NMR (376 MHz, CDCl₃) δ -226.39 (s, 1F).

Step c:

To a solution of acid 9b (3.0 g, 18.3 mmol) in CH₂Cl₂ (183 ml) was added (bromomethyl)benzene (3.75 g, 21.93 mmol), DIEA (3.83 ml, 21.93 mmol), and DMAP (0.112 g, 0.914 mmol). The reaction was stirred at RT under nitrogen for 27.5 h. The reaction was diluted with CH₂Cl₂ (100 mL) and washed with a solution of satd. NaHCO₃, 1 N HCl, water and brine, dried (MgSO₄), and concentrated in vacuo. The residue was purified by an ISCO silca gel cartridge (120 g; 25% EtOAc/hexanes) to afford ester 9c (2.4 g). The racemic sample was separated by chiral SFC (Column: Lux Cellulose-2; Mobile Phase: 10% Heptane:IPA(3:1)/90% CO₂) to afford the two enantiomers as clear light yellow oil [9c.1 (first elute): 494 mg; 9c.2 (second elute): 566.8 mg]. First elute would afford the more active final product. ¹H NMR (400 MHz, CDCl₃) δ 7.47-7.31 (m, 5H), 5.26 (dd, J=18.5, 12.1 Hz, 2H), 4.50 (dd, J=9.1, 86.9 Hz, 1H), 4.38 (dd, J=9.1, 86.9 Hz, 1H), 3.46 (d, J=1.0 Hz, 1H), 1.89-1.72 (m, 1H), 1.68-1.57 (m, 1H), 1.57-1.45 (m, 1H), 0.95 (d, J=6.5 Hz, 3H), 0.81 (d, J=6.8 Hz, 3H). ¹⁹F NMR (376 MHz, CDCl₃) δ -226.20 (s, 1F).

Step d:

A mixture of benzyl ester 9c.1 (0.13 g, 0.511 mmol) and 10% Pd/C (0.054 g) in MeOH (5 mL) was exposed to balloon hydrogen at RT for 0.5 h. The reaction mixture was passed through a Whatman Puradisc 13 mm syringe filter (0.45 μm pore size) and the filtrate concentrated in vacuo to afford acid 9b.1 as white solid (83.6 mg), which was used without further purification. Acid 9b.2 was prepared similarly. NMR (400 MHz, DMSO-d₆) δ4.43 (dd, J=9.1, 80.8 Hz, 1H), 4.32 (dd, J=9.1, 80.8 Hz, 1H), 3.34 (br s, 1H), 1.88-1.68 (m, 1H), 1.57-1.45 (m, 1H), 1.45-1.32 (m, 1H), 1.01 (s, 18H), 0.91 (d, J=6.5 Hz, 3H), 0.86 (d, J=6.5 Hz, 3H). ¹⁹F NMR (376 MHz, DMSO-d₆) δ -225.01 (s, 1F).

Acid 10

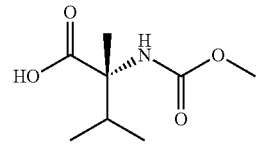

To a solution of (R)-2-amino-2,3-dimethylbutanoic acid (0.25 g, 1.906 mmol) in 1N NaOH (1.9 ml, 1.9 mmol) was added Na₂CO₃ (0.101 g, 0.953 mmol). The flask was lowered into an ice-water bath for 3 min and methyl chloroformate (0.16 ml, 2.0 mmol) was added slowly, stirred for 3 min, the ice-water bath was removed and the reaction mixture was stirred at RT for 1 h. The mixture was acidified with 1N HCl to ~pH 1, extracted with DCM (10 mL×3), dried (Na₂SO₄), and the volatile component was removed in vacuo to afford acid 10 as white foam (0.23 g). ¹H NMR (400 MHz, CDCl₃) δ 3.70 (s, 3H), 2.31-2.12 (m, 1H), 1.55 (s, 3H), 1.03-0.98 (m, 6H). LC/MS: [M+Na]⁺ 211.99.

Acid 11

Scheme 8

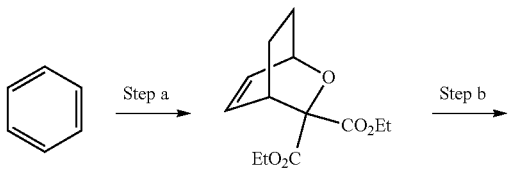

11a

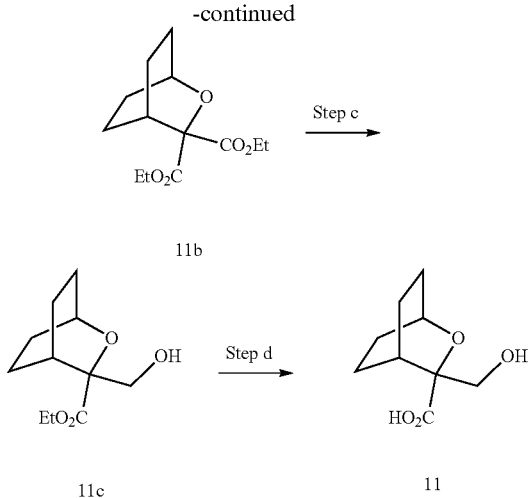

11b

11c

11

Step a:
A neat mixture of cyclohexa-1,3-diene (3.53 g, 44.1 mmol) and diethyl 2-oxomalonate (7.68 g, 44.1 mmol) was placed in a pressure tube, sealed and heated around 120° C. for 24 h. The reaction mixture was purified by silica gel flash chromatography (0-60% EtOAc/Hexanes) to afford 11a as colorless oil (8.04 g). $^1$H NMR (400 MHz CDCl$_3$) δ 6.55 (m, 1H), 6.48 (m, 1H), 4.70 (m, 1H), 4.33-4.09, m, 4H), 3.40 (m, 1H), 2.19 (m, 1H), 1.65 (m, 1H), 1.38-1.23 (m, 8H).

Step b:
10% Pd/C (0.308 g) was placed in a flask and MeOH (30 mL) followed by 11a (3.68 g, 14.47 mmol) were added. The mixture was degassed and stirred at RT under a balloon of hydrogen for 18 h. The reaction mixture was filtered through Celite and the solvent was removed in vacuo to afford diester 11 b as light yellow-green oil (3.04 g) which was used in the next step without purification. $^1$H NMR (400 MHz, CDCl$_3$) δ 4.27 (m, 4H), 4.14 (m, 1H), 2.51 (m, 1H), 2.06 (m, 2H), 1.87 (m, 2H), 1.68-1.51 (m, 4H), 1.30 (t, J=16 Hz, 6H).

Step c:
To a solution of diester 11b (0.256 g, 0.999 mmol) in THF (3 mL) at −78° C. was added lithium tri-tert-butoxyaluminumhydride (5.0 mL of 1.0 M in THF, 5.0 mmol) slowly over 5 min. The mixture was stirred at −78° C. for 30 min and then the cooling bath was removed and the reaction mixture was stirred at RT for 64 h, at which time it became a suspension. 10% KHSO$_4$ (8 mL) was added and the mixture was extracted with EtOAc (2×15 mL), dried (Na$_2$SO$_4$), and evaporated in vacuo. The resultant crude material was purified by silica gel flash chromatography (0-80% EtOAc/Hexanes) to afford alcohol 11c as colorless oil (0.18 g). $^1$H NMR (400 MHz, CDCl$_3$) δ 4.26 (m, 2H), 4.02 (m, 1H), 3.79 (m, 2H), 2.45-2.41 (app. dd, J=12 Hz, 4 Hz, 1H), 2.42 (m, 1H), 2.12 (m, 1H), 2.04 (m, 2H), 1.56 (m, 5H), 1.30 (t, J=16 Hz, 3H).

Step d:
To a solution of alcohol 11c (0.18 g, 0.84 mmol) in THF (4 mL) was added a solution of LiOH (0.03 g, 1.26 mmol) in water (2.0 mL), and the mixture was stirred at RT for 40 h. The organic component was removed in vacuo and the residue was washed with EtOAc (10 mL). The aqueous layer was separated, acidified with 1 N HCl to ~pH 1, and extracted with EtOAc (3×10 mL). The organic layer was dried (Na$_2$SO$_4$) and evaporated in vacuo to afford acid 11 as colorless oil (80 mg). The product, which contained the starting ester as a minor component, was used in the next step as such. LC/MS: [M+Na]$^+$ 209.04.

Acid 12

Scheme 9

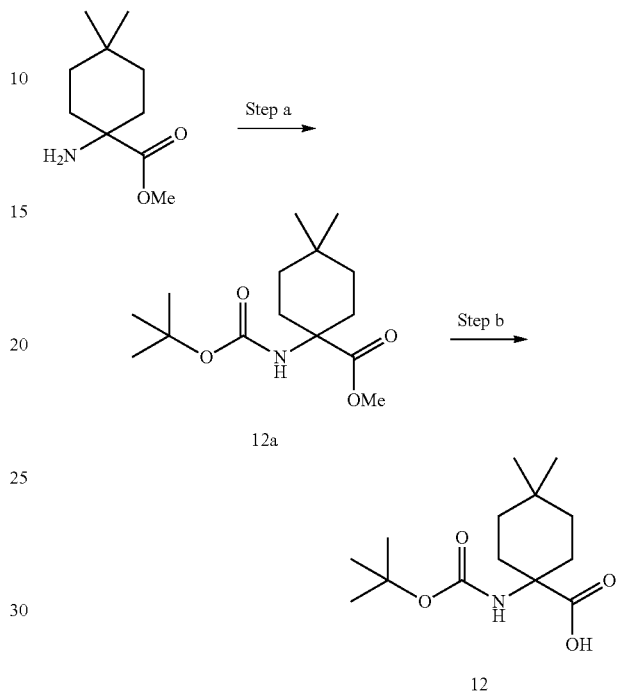

12a

12

Step a:
BOC$_2$O (1.44 mL, 6.21 mmol) was added to a solution of methyl 1-amino-4,4-dimethylcyclohexanecarboxylate (1.0 g, 5.40 mmol) in DCM (20 mL) and the reaction mixture was stirred at RT for 24 h. The reaction mixture was diluted with DCM (20 mL) and washed with 1 N HCl (2×30 mL), water and brine, dried (MgSO$_4$), filtered and concentrated under vacuum. An off-white solid corresponding to 12a was recovered in 70% yield and was used without further purification. $^1$H NMR (500 MHz, CDCl$_3$) δ 4.68 (br. s., 1H), 3.72 (s, 3H), 2.03-1.93 (m, 2H), 1.91-1.82 (m, 2H), 1.44 (s, 9H), 1.41-1.26 (m, 4H), 0.94 (s, 3H), 0.94 (s, 3H)

Step b:
1 N NaOH (4 mL, 4 mmol) was added to a solution to 12a (0.5 g, 1.752 mmol) in THF (15 mL) and the resulting mixture was stirred at RT for 16 h and volatiles were removed under reduced pressure. The aqueous layer was washed with Et$_2$O (20 mL) and then acidified to pH=2 with 1 N HCl. A white precipitate formed. The aqueous layer was then extracted with Et$_2$O (2×), and the combined organic layers were dried (MgSO$_4$) and concentrated. A white foam corresponding to acid 12 was recovered in 42% yield and was used without further purification. $^1$H NMR (400 MHz, DMSO-d$_6$) δ 6.78 (br. s., 1H), 1.87 (br. s., 2H), 1.77-1.63 (m, 2H), 1.36 (s, 9H), 1.32-1.18 (m, 4H), 0.87 (s, 3H). $^{13}$C NMR (101 MHz, DMSO-d$_6$) δ 176.4, 154.7, 77.4, 57.8, 34.2 (2C), 33.7, 30.6, 29.0 (2C), 28.3 (br. s., 3C), 27.8.

Acid 13

Scheme 10

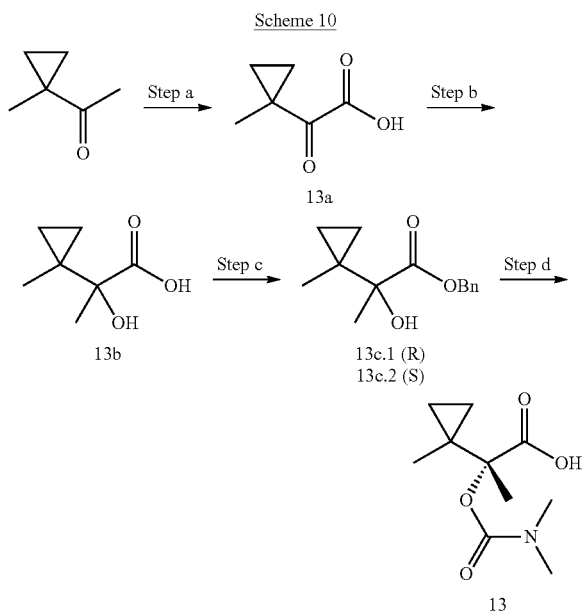

13a

13b 13c.1 (R)
13c.2 (S)

13

Step a:

1-(1-Methylcyclopropyl)ethanone (10 g, 102 mmol), a solution of NaOH (8.15 g, 204 mmol) in $H_2O$ (100 mL) and $H_2O$ (400 mL) were charged to a 500 mL Erlenmeyer flask and cooled in acetone-ice bath. After the inner temperature reached −4° C., $KMnO_4$ (29.0 g, 183 mmol) was added portionwise with vigorous stirring. The inner temperature was controlled at −3 to 1° C. during the addition process, which was finished in 60 min. The reaction mixture was stirred in the bath for 6 h and let warm to RT in the process (the inner temperature reached 16° C.). EtOH (10 mL) was added and stirred for another 15 min. The reaction mixture was filtered to remove the solid and washed with cold water (100 mL). The filtration was acidified with cold 6 N HCl in an ice cold bath to pH<2. The mixture was then extracted with EtOAc (4×100 mL and 3×50 mL). The combined extracts were washed with HCl (1N 50 mL), brine (3×25 mL), dried ($MgSO_4$) and concentrated to give clear oil that solidified upon standing under vacuum. Solid corresponded to ketoacid 13a (9.9 g). $^1H$ NMR (400 MHz, $CDCl_3$) δ 10.21 (br. s., 1H), 1.84-1.78 (m, 2H), 1.36 (s, 3H), 1.09-1.04 (m, 2H). $^{13}C$ NMR (101 MHz, $CD_3Cl$) δ 197.0, 162.1, 26.8, 20.5 (2C), 19.2.

Step b:

A 3 M solution in THF of MeMgCl (56.7 mL, 170 mmol) was added dropwise to a solution of ketoacid 13a (9.9 g, 77 mmol) in THF (150 mL) at 0° C. The resulting solution was then stirred at RT for 24 h. The reaction mixture was then cooled to 0° C. and carefully quenched with 6 N HCl (~25 mL). The organic solvent was removed under reduced pressure and the aqueous layer was extracted with $Et_2O$ (4×150 mL). The combined organic layers were washed with brine, dried ($MgSO_4$), and concentrated under vacuum to give a white solid. The residue was then recrystallized from hot heptanes to give acid 13b (8.5 g) as off-white crystals. NMR (500 MHz, DMSO-$d_6$) δ 12.32 (br. s., 1H), 4.69 (br. s., 1H), 1.20 (s, 3H), 1.00 (s, 3H), 0.76 (dd, J=9.2, 4.3 Hz, 1H), 0.61 (dd, J=9.1, 5.0 Hz, 1H), 0.15-0.04 (m, 2H).

Step c:

Neat benzyl bromide (8.42 mL, 70.8 mmol) was added to a solution of ketoacid 13 b (8.5 g, 59.0 mmol) and DIPEA (13.39 mL, 77 mmol) in $CH_3CN$ (150 mL) and $CHCl_3$ (150 mL) and the mixture was stirred at RT overnight. The reaction mixture was then evaporated to dryness and taken up in ether, washed with 1 N HCl, water and brine, dried ($MgSO_4$) and concentrated under reduced pressure. A clear oil was recovered. This residue was purified via Biotage (0% to 10% EtOAc/Hex; 25 g column). Recovered fraction was concentrated under vacuum to give ester 13c (10.6 g) as a clear liquid. $^1H$ NMR (500 MHz, $CDCl_3$) δ 7.42-7.33 (m, 5H), 5.24 (s, 2H), 3.11 (s, 1H), 1.35 (s, 3H), 1.05 (s, 3H), 0.79-0.70 (m, 2H), 0.29-0.20 (m, 2H). $^{13}C$ NMR (126 MHz, $CDCl_3$) δ 176.5, 135.3, 128.6 (2C), 128.4, 128.1 (2C), 75.7, 67.4, 22.1, 21.7, 20.8, 10.5, 9.3. LC/MS Anal. Calcd. for $[M+H]^+$ $C_{14}H_{19}O_3$: 235.13; found 235.20.

The racemic mixture was separated into its corresponding enantiomers using chiral preparatory SFC purification (Lux Cellulose-2 preparative column, 21.2×250 mm, 5 μm; 10% Heptane:IPA (3:1) in $CO_2$, 40 mL/min, for 11 min.) to yield (R)-benzyl 2-hydroxy-2-(1-methyl cyclopropyl)propanoate (alcohol 13c.1) (4.85 g) as the $1^{st}$ eluting peak and (S)-benzyl 2-hydroxy-2-(1-methyl cyclopropyl)propanoate (alcohol 13c.2) (4.78 g). Each enantiomer was isolated as clear oil.

Step d:

Neat bis(trichloromethyl) carbonate (2.152 g, 7.25 mmol) was added to a −20° C. solution of alcohol 13c.1 (4.53 g, 19.33 mmol) and DMAP (7.68 g, 62.8 mmol) in DCM (200 mL) and the mixture was gradually warmed to RT (30 min) and stirred for 30 min. The resultant white suspension was cooled to −20° C. and treated with dimethylamine (2M in THF; 29.0 mL, 58.0 mmol) and the mixture was stirred at RT for 16 h. The reaction mixture was concentrated under vacuum and the residue was partitioned between $Et_2O$ and 1 N HCl. The organic layer was further washed with 1 N HCl, water and brine, dried ($MgSO_4$) and concentrated to afford a clear oil (5.8 g) which was used without further purification. $^1H$ NMR (500 MHz, $CDCl_3$) δ 7.42-7.28 (m, 5H), 5.23-5.19 (m, 1H), 5.19-5.15 (m, 1H), 2.85 (s, 6H), 1.69 (s, 3H), 1.09-1.02 (m, 1H), 1.01 (s, 3H), 0.80 (dd, J=4.1, 3.3 Hz, 1H), 0.33-0.19 (m, 2H). $^3C$ NMR (126 MHz, $CDCl_3$) δ 171.7, 154.8, 136.1, 128.3 (2C), 128.0 (2C), 127.9, 81.0, 66.6, 36.3, 35.8, 22.2, 20.5, 19.9, 10.6, 9.9.

10% Pd/C (1.011 g) was added to a solution of the above product (5.8 g, 18.99 mmol) in ethyl acetate (250 mL) and the suspension was flushed with $N_2$ (3×). The mixture was then placed under 1 atm of $H_2$ (balloon) and stirred at RT for 2 h. Catalyst was removed by filtration though a plug of Celite® and volatiles were removed under reduced pressure. A white solid corresponding to acid 13 (3.86 g) was recovered and used without further purification. $^1H$ NMR (500 MHz, DMSO-$d_6$) δ 12.45 (br. s., 1H), 2.79 (br. s., 3H), 2.76 (br. s., 3H), 1.50 (s, 3H), 1.02 (s, 3H), 0.95-0.90 (m, 1H), 0.76-0.70 (m, 1H), 0.32-0.23 (m, 2H). $^{13}C$ NMR (126 MHz, DMSO-$d_6$) δ 172.4, 154.0, 79.9, 35.7, 35.3, 21.8, 20.3, 19.6, 10.2, 9.5. NOTE: The absolute stereochemistry of acid 13 was determined by single crystal X-Ray analysis of an amide analog prepared from the enantiomer of acid 13 [i.e., (R)-benzyl 2-((dimethylcarbamoyl)oxy)-2-(1-methylcyclopropyl)propanoate] and (S)-1-(napthalen-2-yl)ethanamide.

Acid 14

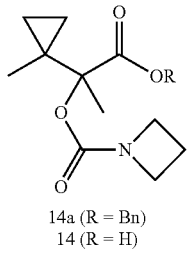

14a (R = Bn)
14 (R = H)

10% Pd/C (0.053 g) was added to a solution of racemate ester 14a (prepared from appropriate precursors according to procedure noted in Scheme 10; 100.0 mg, 0.498 mmol) in EtOAc (15 mL) and the resulting mixture was flushed with N₂ (3×). The black suspension was then placed under 1 atm of H₂ (balloon) and stirred at RT for 3 h. The reaction was monitored by TLC until complete disappearance of starting material. The catalyst was removed by passing the mixture though a plug of Celite® and volatiles were removed under reduced pressure. An off-white solid corresponding to acid 14 was recovered and used without further purification. NMR (500 MHz, DMSO-$d_6$) δ 12.59 (br. s., 1H), 3.96-3.74 (m, 4H), 2.15 (quint, J=7.6 Hz, 2H), 1.48 (s, 3H), 1.00 (s, 3H), 0.92-0.84 (m, 1H), 0.71-0.64 (m, 1H), 0.26-0.19 (m, 2H). ¹³C NMR (126 MHz, DMSO-$d_6$) δ 172.4, 154.2, 79.5, 49.1, 48.5, 21.7, 20.2, 19.6, 15.1, 10.1, 9.4.

Acid 15

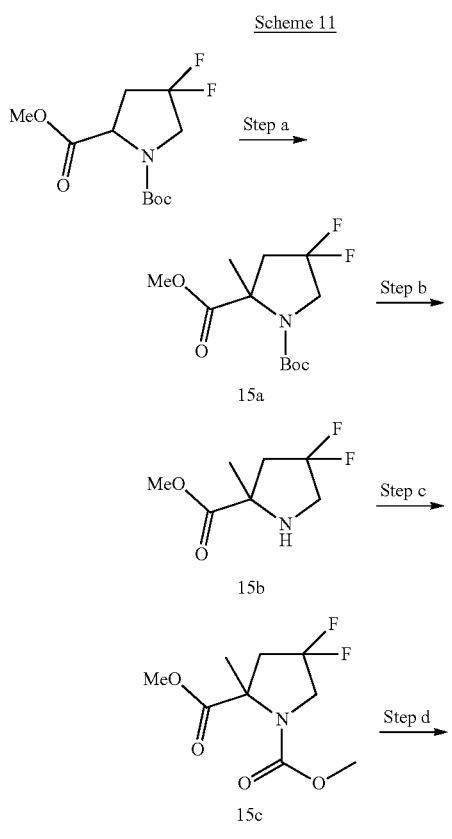

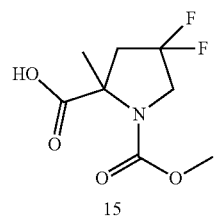

15

Step a:

To a solution of (S)-1-tert-butyl 2-methyl 4,4-difluoropyrrolidine-1,2-dicarboxylate (1.55 g, 5.68 mmol) in THF (50 mL) at −78° C. was added 2 M LDA in THF (3.12 mL, 6.24 mmol) dropwise via a syringe. After stirring the light yellow solution at −78° C. for 30 min (it turned into a light brown solution), iodomethane (0.389 mL, 6.24 mmol) was added dropwsie via a syringe. After stirring at −78° C. for 2 h, the reaction mixture was stirred at 0° C. for 2 h and quenched with saturated aqueous solution of NH₄OAc and extracted with EtOAc. The combined organic extracts were washed with brine, dried (MgSO₄), and concentrated in vacuo. The residual oil was purified by FCC (90 g silica gel cartridge, 0-30% EtOAc/hexanes) to afford ester 15a (526 mg) as a colorless oil. ¹H NMR (400 MHz, CDCl₃) δ 3.96-3.81 (m, 2H), 3.80-3.75 (m, 3H), 2.82-2.57 (m, 1H), 2.48-2.27 (m, 1H), 1.78-1.62 (m, 3H), 1.53-1.39 (m, 9H).

Step b:

To an ice-cooled solution of 15a (379 mg, 1.357 mmol) in MeOH (5 mL) was added 4 M HCl in 1,4-dioxane (1.357 mL, 5.43 mmol), and the resultant solution was stirred at RT for 2 h. Another 10 eq of HCl was added and stirring continued at RT overnight. The volatiles were removed in vacuo and the residue was triturated with ether, filtered, and dried in vacuo to afford 15b/HCl (220 mg) as an off-white solid. ¹H NMR (400 MHz, MeOH-$d_4$) δ 4.05-3.84 (m, 5H), 3.18-3.00 (m, 1H), 2.79 (q, J=14.3 Hz, 1H), 1.81 (s, 3H).

Step c:

To an ice cooled solution of 15 b/HCl (0.164 g, 0.761 mmol) in DCM (5 mL) was added DIEA (0.33 mL, 1.90 mmol) and methyl chlorocarbonate (0.071 mL, 0.913 mmol). The formed light yellow solution was stirred at RT for 2 h, diluted with DCM, washed with 1 M HCl and brine, dried (MgSO₄), and evaporated in vacuo to afford the 15c (0.182 g) as a light brown oil. ¹H NMR (400 MHz, CDCl₃) δ 4.02-3.85 (m, 2H), 3.83-3.75 (m, 3H), 3.73 (m, 3H), 2.85-2.57 (m, 1H), 2.51-2.27 (m, 1H), 1.83-1.57 (m, 3H).

Step d:

A vial containing 15c (182 mg, 0.767 mmol), THF (7 mL), and a 1 M solution of NaOH (7.67 mL, 7.67 mmol) was sealed and heated in a microwave system at 50° C. for 2 h. The volatiles were removed in vacuo and the remaining aqueous layer was extracted with ether. The separated aq. layer was acidified with 5% citric acid to pH 3, saturated with NaCl and extracted with EtOAc (10 mL, 3×). The combined organic layers were washed with brine, dried (MgSO₄), and evaporated in vacuo to afford acid 15 (135 mg) as a colorless viscous oil. ¹H NMR (400 MHz, CDCl₃) 4.03-3.83 (m, 2H), 3.82-3.73 (m, 3H), 2.98-2.75 (m, 1H), 2.57-2.35 (m, 1H), 1.83-1.65 (m, 3H).

Acid 16

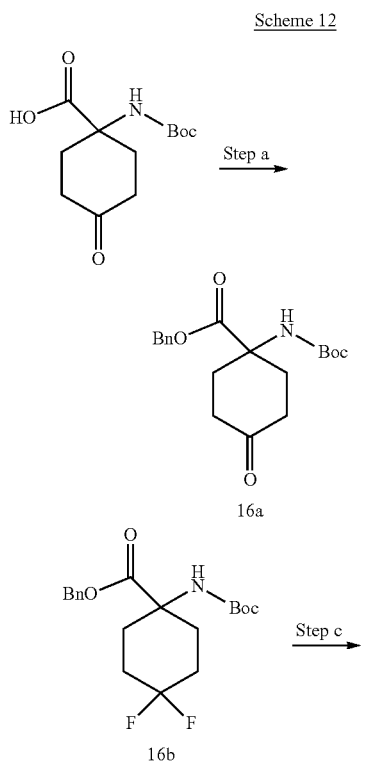

Step a:
To a mixture of 1-((tert-butoxycarbonyl)amino)-4-oxocyclohexanecarboxylic acid (1.00 g, 3.69 mmol) and CsCO$_3$ (1.564 g, 4.80 mmol) in DMF (20 mL) was added benzyl bromide (0.527 mL, 4.43 mmol) and the reaction mixture was stirred at RT overnight. Solids were filtered through a pad of Celite® and the filtrate was diluted with water (50 mL) and extracted with TBME (20 mL×2). The combined organic layers were washed with water and brine, dried (MgSO$_4$), and evaporated in vacuo. The residual oil was purified by FCC (80 g silica gel cartridge, 0-50% EtOAc-hexanes) to afford ester 16a (1.27 g) as a colorless oil, which solidified upon standing. $^1$H NMR (500 MHz, CDCl$_3$) δ 7.45-7.32 (m, 5H), 5.21 (s, 2H), 4.95 (br. s., 1H), 2.57-2.28 (m, 8H), 1.44 (s, 9H).

Step b:
To a cooled solution (ice bath) of ester 16a (1.12 g, 3.22 mmol) in DCM (20 mL) was added DAST (0.852 mL, 6.45 mmol) dropwise. The formed solution was stirred at RT overnight and then it was quenched with sat. NaHCO$_3$. The separated organic layer was washed with brine, dried (MgSO$_4$), and evaporated in vacuo. The residual oil was purified by FCC (120 g silica gel cartridge, 0%-50% EtOAc-hexanes). The obtained crude product was dissolved in acetone (4 mL), THF (8 mL), and water (4 mL), cooled (ice bath), and charged with NMO (268 mg, 2.290 mmol) and OSO4 (4% in water) (0.225 mL, 0.029 mmol). The reaction mixture was stirred at RT overnight and then it was diluted with EtOAc. The organic layer was washed with water, sat. aq. NH$_4$Cl and brine, dried (MgSO$_4$) and purified by FCC (80 g silica gel cartridge, 0%-100% EtOAc/hexanes) to afford 16b. $^1$H NMR (400 MHz, CDCl$_3$) δ 7.45-7.30 (m, 5H), 5.14 (s, 2H), 4.77 (b, 1H), 2.35-1.83 (m, 8H), 1.38 (s, 9H).

Step c:
A vessel containing ester 16b (280 mg, 0.758 mmol), Pearlman's catalyst (26.6 mg, 0.038 mmol) and TBME (8 mL) was placed under hydrogen (30 psi) for 2 h. The catalyst was removed by filtration through a pad of Celite® and the filtrate was then evaporated in vacuo to afford 16 (210 mg)) as a colorless foam, which was used without further purification. $^1$H NMR (500 MHz, MeOH-d$_4$) δ 2.27-1.90 (m, 8H), 1.52-1.41 (overlapping s, 9H).

Acid 17

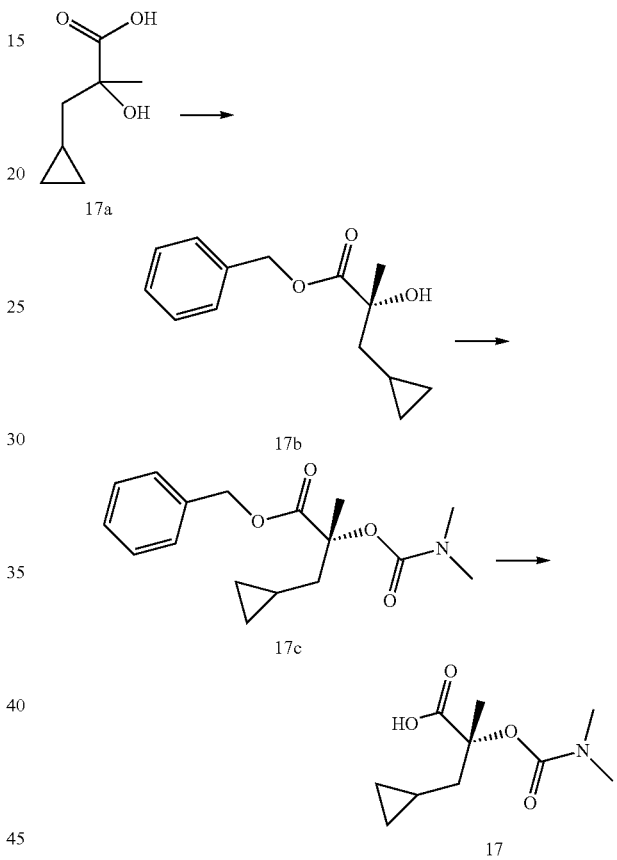

To a stirred solution of acid 17a (15 g, 104 mmol) and DIPEA (27.3 mL, 156 mmol) in DCM (11 mL) was added dropwise benzyl bromide (14.85 mL, 125 mmol) and stirred at RT for 12 h. Reaction was quenched with saturated solution of NH$_4$Cl and extracted with EtOAc (2×). Organic layer was dried (sodium sulfate) and evaporated under reduced pressure to obtained 22 g of racemic material as pale yellow liquid. Compound was submitted for SFC purification (0.3% DEA in Methanol, Chiralpak AD-H (250×4.6) mm, 5µ; R$_t$=3.27 min) to obtain desired enantiomer 17b, which was the second peak to elute (6 g). $^1$H NMR (300 MHz, CDCl$_3$) δ 7.41-7.36 (m, 5H), 5.29-5.15 (m, 2H), 3.35 (brs, 1H), 1.78-1.71 (m, 1H), 1.63-1.55 (m, 1H), 1.46 (s, 3H), 0.78-0.72 (m, 1H), 0.51-0.42 (m, 1H), 0.40-0.31 (m, 1H), 0.14-0.06 (m, 1H), 0.02-(−0.03) (m, 1H).

To a stirred solution of alcohol 17b (2 g, 8.54 mmol) and DMAP (3.34 g, 27.3 mmol) in THF (50 mL) at −20° C. was added triphosgene (2.53 g, 8.54 mmol) and the reaction mixture was slowly warmed to RT and stirred for 1 h. Then it was cooled back to −20° C., and dimethylamine (28.5 mL, 42.7 mmol) followed by DIPEA (2.98 mL, 17.07 mmol) were added. The reaction mixture was stirred overnight while allowing it to warm up to RT. It was quenched with 1.5N HCl and extracted with DCM (2×), dried (Na$_2$SO$_4$) and concentrated in vacuo. The crude material was purified by preparative HPLC (CH$_3$CN/NH$_4$OAc/H$_2$O) to afford carbamate 17c (1 g). $^1$H NMR (400 MHz, CDCl$_3$) δ 7.35-7.30 (m, 5H), 5.21-5.13 (m, 2H), 2.92 (brs, 3H), 2.89 (brs, 3H), 1.89-1.84 (m, 1H), 1.76-1.71 (m, 1H), 1.70 (s, 3H), 0.76-0.69 (m, 1H), 0.45-0.41 (m, 2H), 0.06-0.03 (m, 2H).

To a stirred solution of ester 17c (0.1 g, 0.327 mmol) in EtOAc (15 mL) was added 10% Pd/C (0.348 g), the mixture was degassed for 5 min and subjected for hydrogenation under balloon pressure for 2 h. Then the reaction mixture was filtered through Celite and the filtrate was evaporated under reduced pressure to afford acid 17 (0.07 g).

Acid 18

Scheme 14:

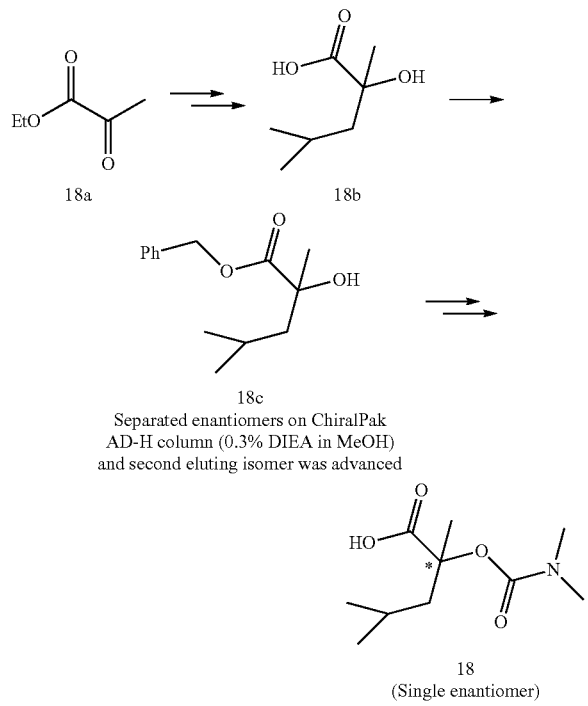

18a

18b

18c
Separated enantiomers on ChiralPak
AD-H column (0.3% DIEA in MeOH)
and second eluting isomer was advanced 18
(Single enantiomer)

Acid 18 was prepared from ethyl pyruvate by adaptation of procedures described in the synthesis of acid 1 and acid 17 with the exception that the Grignard addition was done on ester 18a and that the resultant product was submitted to standard saponfication to afford acid 18b.

Example N1

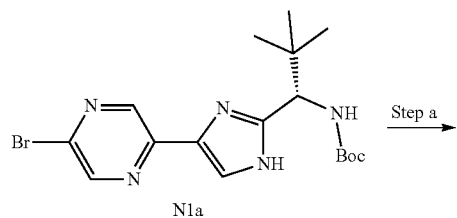

N1a

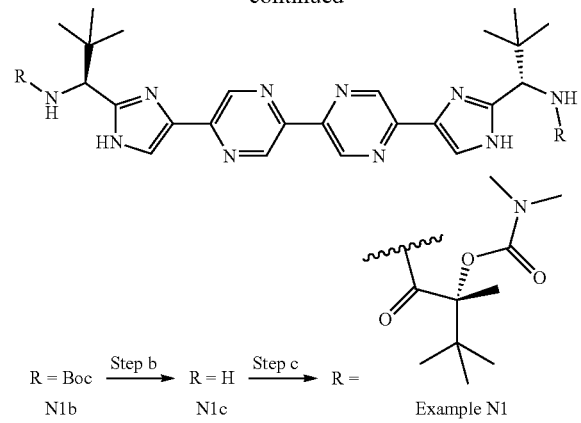

R = Boc $\xrightarrow{\text{Step b}}$ R = H $\xrightarrow{\text{Step c}}$ R =

N1b    N1c    Example N1

Bromide N1a was prepared according to the procedure described for the preparation of Example N-77 and N-104 in patent application WO 2013-106520. LC/MS (Condition 1): R$_t$=3.05 min, [M+H]$^+$ 410.15.

To a stirred solution of bromide N1a (0.356 g, 0.868 mmol) and bis(benzonitrile)palladium(II) chloride (0.017 g, 0.043 mmol) in dry DMF (2 mL) at RT under N$_2$ was added neat N1,N1,N'1,N'1,N2,N2,N'2,N'2-octamethylethene-1,1,2,2-tetraamine (0.406 mL, 1.735 mmol). The reaction mixture was heated to 70° C. for 16 h. Then the reaction was cooled to RT, diluted with EtOAc, washed with satd. NaHCO$_3$, satd. NaCl, dried over anhydrous Na$_2$SO$_4$, and concentrated. The crude product was purified by preparative HPLC (H$_2$O/MeOH/TFA) to yield the TFA salt of bis-pyrazine N1b. LC/MS (Condition 1): R$_t$=3.46 min, [M+H]$^+$ 661.50.

To a suspension of bis-pyrazine N1b (0.040 g, 0.045 mmol) in DCM (10 mL) was added hydrogen chloride/dioxane (0.11 mL of 4N, 0.44 mmol) along with 1 mL of MeOH. The reaction mixture was stirred at RT for 16 h. The reaction mixture was concentrated to dryness to afford the HCl salt of amine N1c as a yellow solid. LC/MS (Condition 1): R$_t$=3.02 min, [M+H]$^+$ 461.35.

To a solution of acid 2 (0.07 g, 0.322 mmol) and pyridine (0.029 mL, 0.354 mmol) in DCM (4 mL) was added cyanuric fluoride (0.055 mL, 0.644 mmol) at 0° C. and the resulting mixture was stirred at RT for 2.5 h. The resulting milky suspension was poured onto 10 mL of ice-cold water and diluted with DCM. The separated organic layer was washed with water and brine, dried (Na$_2$SO$_4$), and concentrated to yield (R)-1-fluoro-2,3,3-trimethyl-1-oxobutan-2-yl dimethylcarbamate.

To a solution of the above crude product (0.072 g, 0.330 mmol) and the HCl salt of amine N1c (0.04 g, 0.066 mmol) in DMF (0.5 mL) was added DIEA (0.092 mL, 0.528 mmol) and the resulting mixture was stirred at 40° C. for 24 h. Then the reaction was diluted with EtOAc, washed with satd. NaHCO$_3$, water, brine, and dried (Na$_2$SO$_4$), and concentrated in vacuo. The resultant crude material was purified by HPLC (CH$_3$CN/H$_2$O/NH$_4$OAc) to afford Example N1. LC/MS (Condition 1): R$_t$=3.85 min, [M+H]$^+$ 859.70.

Example N2

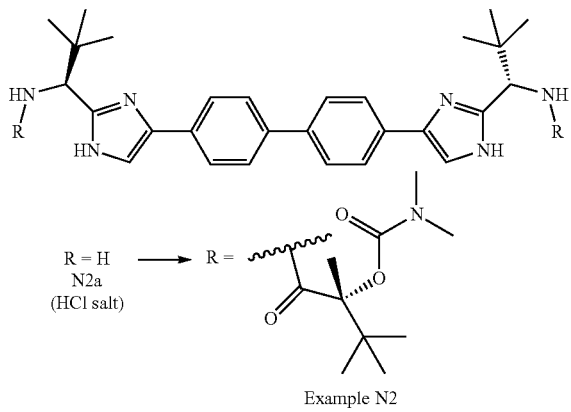

Example N2

To a solution of the HCl salt of amine N2a (for preparation, see WO2013/106520; 0.045 g, 0.074 mmol), acid 2 (0.042 g, 0.193 mmol), and 1-hydroxy-7-azabenzotriazole (0.025 g, 0.186 mmol) in DMF (0.8 mL) was added DIEA (0.078 mL, 0.446 mmol) followed by EDC (0.037 g, 0.193 mmol) 1 min later. The reaction mixture was stirred at RT for 16 h and at 50° C. for 6 h. The reaction mixture was purified by reverse phase HPLC (H$_2$O/CH$_3$OH/TFA) to afford the TFA salt of Example N2. $^1$H NMR (400 MHz, MeOH-d$_4$) δ 7.99-7.78 (m, 10H), 5.13-5.05 (m, 2H), 2.99 (s, 6H), 2.89-2.76 (m, 6H), 1.78 (s, 6H), 1.21-0.98 (m, 36H). LC/MS (Condition 1): R$_t$=3.65 min, [M+H]$^+$ 855.6.

Example N3 TO N9

Example N3 to N9 were prepared from appropriate precursors according to the procedure described for the preparation Example N2. For the preparation of the scaffold precursor to Example N7 to N9, see patent application WO2013/106520. Note that in cases where racemic acid was used as coupling partner, a mixture of three disatereomers was obtained that was separable under the purification condition noted for Example N2. Moreover the first eluting diastereomer was the more active of the set.

| Ex. | Structure | LC/MS Conditions | R$_t$ (min) | (M+H)$^+$ |
|---|---|---|---|---|
| N3 | 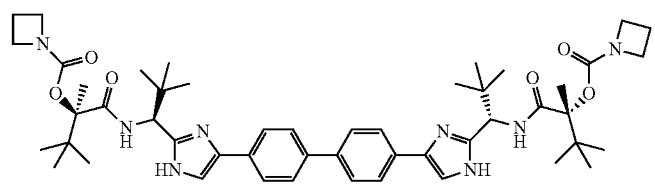 [SMILES: CC(C)(C)[C@H](NC(=O)[C@](C)(OC(=O)N1CCC1)C(C)(C)C)c1nc(-c2ccc(-c3ccc(-c4c[nH]c([C@@H](NC(=O)[C@](C)(OC(=O)N5CCC5)C(C)(C)C)C(C)(C)C)n4)cc3)cc2)c[nH]1] | 1 | 3.68 | 879.6 |
| N4 | (symmetrical, 1$^{st}$ eluting diastereomer) | 1 | 3.47 | 847.6 |
| N5 | (symmetrical, 1$^{st}$ eluting diastereomer) | 1 | 3.56 | 851.65 |
| N6 | (symmetrical, 1$^{st}$ eluting diastereomer) | 2 | 2.43 | 879.9 |

| Ex. | Structure | LC/MS Conditions | R$_t$ (min) | (M+H)$^+$ |
|---|---|---|---|---|
| N7 | 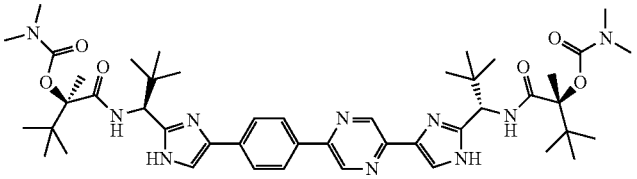 | 1 | 3.72 | 857.6 |
| N8 | 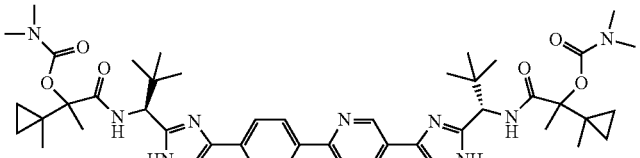 (symmetrical, 1$^{st}$ eluting diastereomer) | 1 | 3.45 | 853.58 |
| N9 | 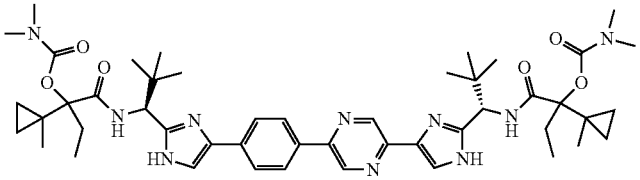 (symmetrical, 1$^{st}$ eluting diastereomer) | 2 | 2.32 | 881.9 |

Example P1 TO P15

Synthesis of intermediate P1b

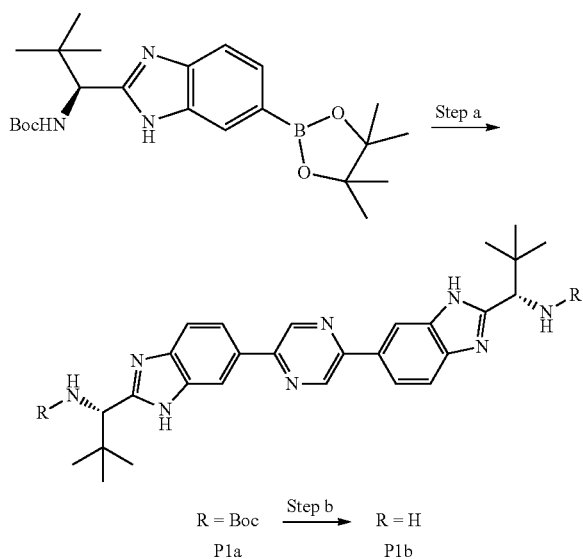

Neat PdCl$_2$(dppf) (0.142 g, 0.194 mmol) was added to a solution of (S)-tert-butyl (2,2-dimethyl-1-(6-(4,4,5,5-tetramethyl-1,3,2-dioxaborolan-2-yl)-1H-benzo[d]imidazol-2-yl)propyl)carbamate (2.0 g, 4.66 mmol) and 2,5-dibromopyrazine (0.462 g, 1.941 mmol) in dioxane (4 mL) and water (1 mL), sparged with nitrogen and then heated at 100° C. for 16 h. Reaction mixture was cooled to RT, diluted with water (15 mL) and extracted with EtOAc (25 ml×2). The combined organic phase was washed with brine, dried (Na$_2$SO$_4$) and evaporated in vacuo. Crude isolate was purified by silica gel FCC (20-40% EtOAc in DCM) to afford carbamate P1a as yellow solid (0.83 g). $^1$H NMR (500 MHz, DMSO-d$_6$) 9.57 (d, J=6.0 Hz, 2H), 9.47 (d, J=5.6 Hz, 2H), 8.51 (s, 1H), 8.37 (s, 1H), 8.17-8.06 (m, 2H), 7.76 (d, J=8.5 Hz, 1H), 7.67 (d, J=8.4 Hz, 1H), 7.14-6.96 (m, 2H), 4.76-4.64 (m, 2H), 1.39 (s, 18H), 0.97 (s, 18H). LC/MS: [M+H]$^+$ 682.

4 N HCl in dioxane (1.64 mL, 6.56 mmol) was added to a solution of carbamate P1a (0.224 g, 0.328 mmol) in DCM (3 mL) and the mixture was stirred at RT overnight. Reaction mixture was evaporated to dryness to afford the HCl salt of intermediate P1b as beige solid. $^1$H NMR (500 MHz, MeOH-d$_4$) δ 9.43-9.36 (m, 2H), 8.72-8.64 (m, 2H), 8.47-8.37 (m, 2H), 8.06-7.98 (m, 2H), 4.86-4.82 (m, 2H), 1.26 (s, 18H). LC/MS [M+H]$^+$ 483.

Synthesis of Intermediate P2d

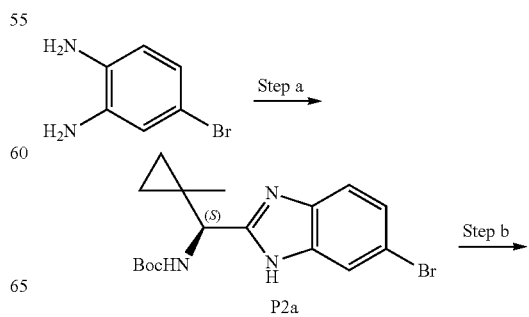

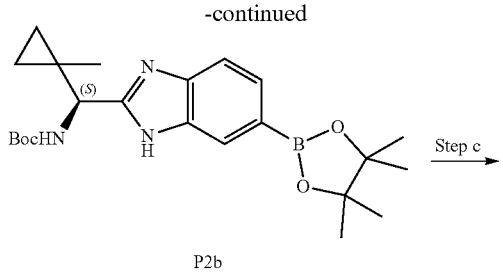

P2b

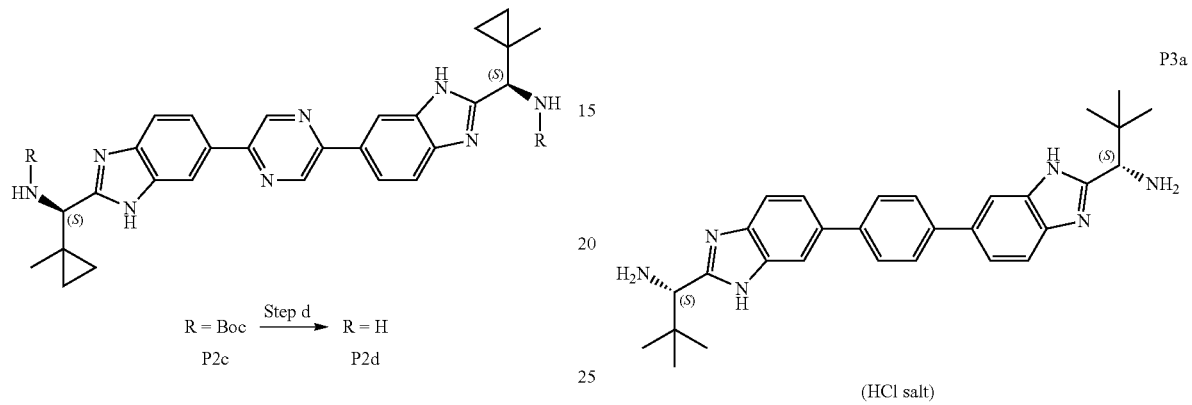

R = Boc  Step d  R = H
P2c          P2d

HATU (3.27 g, 8.59 mmol) was added to a solution of 4-bromobenzene-1,2-diamine (1.607 g, 8.59 mmol), (S)-2-((tert-butoxycarbonyl)amino)-2-(1-methylcyclopropyl)acetic acid (see WO2013/106520 for preparation; 1.97 g, 8.59 mmol) and DIPEA (1.501 mL, 8.59 mmol) in DCM (30 mL) and the reaction mixture was stirred at RT overnight. It was then diluted with DCM and washed with satd. NaHCO$_3$, water, and brine, and dried (MgSO$_4$), and concentrated. Crude isolate was purified by silica gel FCC (10-15% EtOAc in DCM) to afford coupled product as regioisomeric mixture (3.22 g) which was dissolved in glacial acetic acid (30 mL) and heated at 60° C. for 48 h. Acetic acid was evaporated under reduced pressure, while keeping the bath temperature below 40° C., and the residue was dissolved in DCM (50 mL), washed carefully with satd. NaHCO$_3$, water, brine and dried (MgSO$_4$), and concentrated. Crude isolate was triturated with DCM and hexanes to yield bromide P2a as off-white solid (1.36 g). Mother liquor was evaporated to dryness and purified by silica gel FCC (0-30% EtOAc in hexane) to provide 1.13 g of additional product.

A mixture of bromide P2a (1.36 g, 3.58 mmol), potassium acetate (0.860 g, 8.76 mmol) and 4,4,4',4',5,5,5',5'-octamethyl-2,2'-bi(1,3,2-dioxaborolane) (1.862 g, 7.33 mmol) in dioxane (15 mL) was purged with N$_2$ for 15 min and added Pd(Ph$_3$P)$_4$ (0.140 g, 0.121 mmol) and purged again with N$_2$ for 5 min. The reaction mixture was heated at 90° C. for 18 h. The solvent was evaporated and the residue was dissolved in DCM and washed with water, satd. NaHCO$_3$ and dried (MgSO$_4$), and concentrated. Crude isolate was purified by silica gel FCC (20% EtOAc in DCM) to afford boronate P2b as beige solid (1.1 g).

PdCl$_2$(dppf) (0.078 g, 0.107 mmol) was added to a solution of boronate P2b (1.1 g, 2.57 mmol) and 2,5-dibromopyrazine (0.255 g, 1.073 mmol) in dioxane (4 mL) and water (1 mL), sparged with nitrogen, sealed and heated at 100° C. for 16 h. Reaction mixture was diluted with water (15 mL) and extracted with EtOAc (25 mL×2). The combined organic phase was washed with brine, dried (Na$_2$SO$_4$), and concentrated. Crude isolate was purified by silica gel FCC (20-40% EtOAc in DCM) to afford pyrazine P2c as yellow solid (0.8 g).

4 N HCl in dioxane (6.0 mL, 24 mmol) was added to a solution of pyrazine P2c (0.80 g, 1.18 mmol) in DCM (3 mL) and the mixture was stirred at RT overnight. Reaction mixture was evaporated to dryness to afford the HCl salt of amine P2d (0.7 g) as beige solid. $^1$H NMR (500 MHz, MeOH-d$_4$) δ 9.40 (s, 2H), 8.67 (s, 2H), 8.45-8.35 (m, 2H), 8.05-7.97 (m, 2H), 7.26-7.08 (m, 2H), 4.56-4.47 (m, 2H), 3.68 (s, 6H), 1.24-1.18 (m, 2H), 1.08-1.01 (m, 2H), 0.89-0.79 (m, 4H). LC/MS: (M+H)+479.

Synthesis of Intermediate P1a

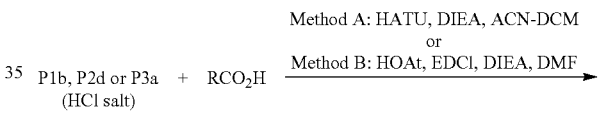

(HCl salt)

The synthesis of P32 is described in patent application WO2013/106520.

General Procedure for Amide Coupling:

P1b, P2d or P3a + RCO$_2$H $\xrightarrow{\text{Method A: HATU, DIEA, ACN-DCM} \atop \text{or} \atop \text{Method B: HOAt, EDCl, DIEA, DMF}}$
(HCl salt)

Example P1 to P15

Example P1 to P15 were prepared from appropriate core and acid precursors under one of the two noted standard coupling conditions and final products were purified via preparative HPLC: Column: XBridge C18, 19×200 mm, 5 μm particles; Mobile Phase A: 5:95 CH$_3$CN: H$_2$O with 10 mM NH$_4$OAc; Mobile Phase B: 95:5 CH$_3$CN: H$_2$O with 10 mM NH$_4$OAc; Gradient: 55-95% B over 40 min, then a 5 min hold at 100% B; Flow: 20 mL/min. Fractions containing the desired product were combined and dried in vacuo. Of noteworthy, in case where a racemic acid coupling partner used, the resultant diastereomers have been separated and the analytical and biological data provided are for the most active isomer.

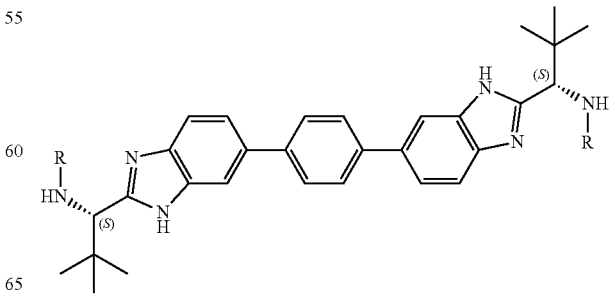

| Example | R | LC/MS Condition | R$_t$ (min) | (M + H)$^+$ |
|---|---|---|---|---|
| P1 | | 3 | 3.07 | 814.4 |
| P2[a] | | 3 | 3.41 | 878.5 |
| P3[b] (Symmetrical diastereomer, 1$^{st}$ elute) | | 3 | 3.3 | 874.5 |
| P4 (Symmetrical diastereomer, 1$^{st}$ elute) | | 3 | 3.32 | 914.5 |

[a] $^1$H NMR of P2: (500 MHz, DMSO-d$_6$) δ 7.93-7.91 (m, 1H), 7.80-7.78 (m, 4H), 7.77-7.75 (m, 1H), 7.71-7.67 (m, 1H), 7.61-7.54 (m, 1H), 7.53-7.49 (m, 1H), 6.91-6.81 (m, 1H), 5.13-5.02 (m, 2H), 3.03 (s, 6H), 2.85 (s, 6H), 1.59 (s, 6H), 0.95 (s, 18H), 0.90 (s, 18H).

[b] $^1$H NMR of P3 (500 MHz, DMSO-d$_6$) δ 7.96-7.92 (m, 1H), 7.80-7.78 (m, 4H), 7.78-7.76 (m, 1H), 7.71 (d, J = 8.1 Hz, 1H), 7.61-7.54 (m, 2H), 7.54-7.50 (m, 1H), 6.93 (t, J = 8.3 Hz, 2H), 5.03 (dd, J = 9.2, 6.6 Hz, 2H), 2.95 (s, 6H), 2.82 (s, 6H), 1.57 (s, 6H), 1.04-0.98 (m, 2H), 0.95 (s, 18H), 0.73-0.64 (m, 2H), 0.27-0.19 (m, 2H), 0.17-0.10 (m, 2H).

| Example | R | LC/MS Method | R$_t$ (min) | (M + H)$^+$ |
|---|---|---|---|---|
| P5[a] | | 3 | 3.21 | 806.4 |
| P6 | | 3 | 3.02 | 816.4 |
| P7[b] | | 3 | 3.24 | 876.5 |
| P8[c] | | 3 | 3.29 | 880.5 |
| P9[d] (Symmetrical diastereomer, 1$^{st}$ elute) | | 3 | 3.07 | 826.5 |
| P10 | | 3 | 3.21 | 876.5 |
| P11 | | 3 | 3.22 | 848.5 |
| P12 (Symmetrical diastereomer, 1$^{st}$ elute) | | 3 | 3.15 | 893.45 |
| P13 (Single symmetrical diastereomer) | | 3 | 3.34 | 880.5 |

-continued

| Example | R | LC/MS Method | $R_t$ (min) | (M+H)$^+$ |
|---|---|---|---|---|
| P14 | 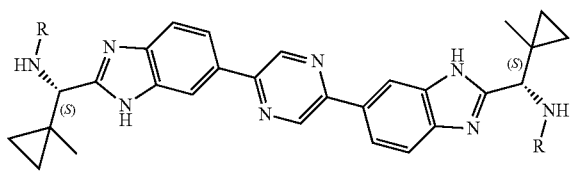 | 3 | 3.35 | 928.5 |

[a] $^1$H NMR of P5 (500 MHz, DMSO-d$_6$) δ 9.35 (s, 2H), 8.46 (br. s., 1H), 8.31 (br. s., 1H), 8.14-8.07 (m, 2H), 7.85-7.79 (m, 2H), 7.74 (br. s., 1H), 7.68 (br. s., 1H), 5.15-5.04 (m, 2H), 3.96-3.84 (m, 2H), 3.80-3.69 (m, 2H), 2.21-2.13 (m, 2H), 2.12-2.03 (m, 2H), 1.86-1.74 (m, 2H), 1.73-1.65 (m, 2H), 1.47 (s, 6H), 1.00 (s, 18H).
[b] $^1$H NMR of P7 (500 MHz, DMSO-d$_6$) δ 9.34 (br. s., 2H), 8.46 (br. s., 1H), 8.30 (br. s., 1H), 8.09 (d, J = 8.1 Hz, 1H), 8.04 (d, J = 8.1 Hz, 1H), 7.76 (d, J = 8.1 Hz, 1H), 7.65 (d, J = 8.1 Hz, 1H), 6.94 (d, J = 9.2 Hz, 2H), 5.05 (br. s., 2H), 2.94 (br. s., 6H), 2.82 (s, 6H), 1.57 (s, 7H), 1.05-0.98 (m, 3H), 0.95 (s, 19H), 0.72-0.64 (m, 2H), 0.23 (dt, J = 9.4, 4.6 Hz, 2H), 0.13 (br. s., 2H).
[c] $^1$H NMR of P8 (500 MHz, DMSO-d$_6$) δ 9.34 (br. s, 2H), 8.44 (br. s., 1H), 8.30 (br. s., 1H), 8.07 (br. s., 2H), 7.74 (br. s., 1H), 7.66 (br. s., 1H), 6.92-6.80 (m, J = 9.2 Hz, 2H), 5.15-5.04 (m, J = 9.2 Hz, 2H), 3.04 (br. s., 6H), 2.85 (br. s., 6H), 1.59 (s, 6H), 0.96 (s, 18H), 0.90 (s, 18H).
[d] $^1$H NMR of P9 (500 MHz, DMSO-d$_6$) δ 9.34 (s, 2H), 8.48 (br. s., 1H), 8.30 (br. s., 1H), 8.06 (br. s., 2H), 7.96-7.88 (m, 2H), 7.76 (br. s., 1H), 7.65 (br. s., 1H), 5.19-5.09 (m, 2H), 4.72-4.63 (m, 2H), 4.62-4.53 (m, 2H), 3.36 (br. s., 3H), 2.55 (br. s., 3H), 1.81 (d, J = 15.0 Hz, 2H), 1.16 (d, J = 15.0 Hz, 2H), 0.98 (s, 18H), 0.76 (s, 6H), 0.13-0.01 (m, 4H), 0.12- -0.23 (m, 2H), −0.63- -0.74 (m, 2H).

| Example | R | LC/MS Method | $R_t$ (min) | (M+H)$^+$ |
|---|---|---|---|---|
| P15 | (structure) | 3 | 3.16 | 872.5 |

Example Y1

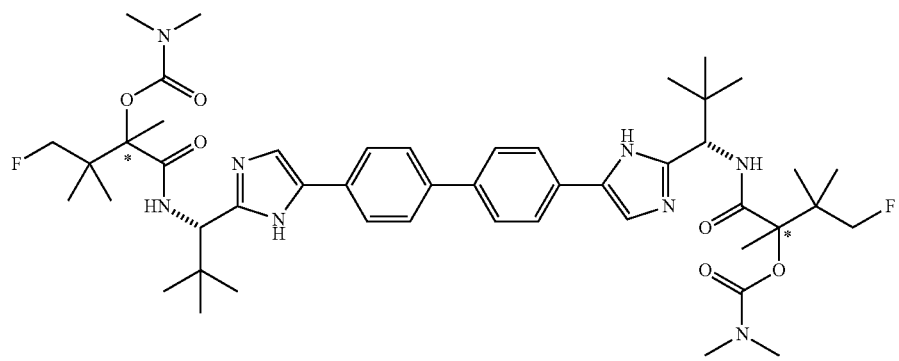 [SMILES: CN(C)C(=O)OC(C)(C(=O)N[C@H](c1ncc(-c2ccc(-c3ccc(-c4cnc([C@@H](NC(=O)C(C)(OC(=O)N(C)C)C(C)(C)CF)C(C)(C)C)[nH]4)cc3)cc2)[nH]1)C(C)(C)C)C(C)(C)CF]

To a solution of acid 6 (38.4 mg, 0.163 mmol), 1-hydroxy-7-azabenzotriazole (22.23 mg, 0.163 mmol) and EDC (31.3 mg, 0.163 mmol) in DMF (1 mL) were added neat DIEA (0.052 mL, 0.299 mmol). After stirring at RT for ~15 min, the HCl salt of amine N2a (41.0 mg, 0.068 mmol) and DIEA (0.052 mL, 0.299 mmol) were added and the mixture was stirred at 45-50° C. overnight and then purified by reverse phase prep HPLC (XBridge Phenyl C18; CH$_3$CN/H$_2$O/NH$_4$OAc) to afford three separate diastereomers. Example Y1 (5.3 mg), which is the most active of the set, eluted first. LC/MS (Condition 3): $R_t$=2.37 min, [M+H]$^+$ 891.50.

Example Y2

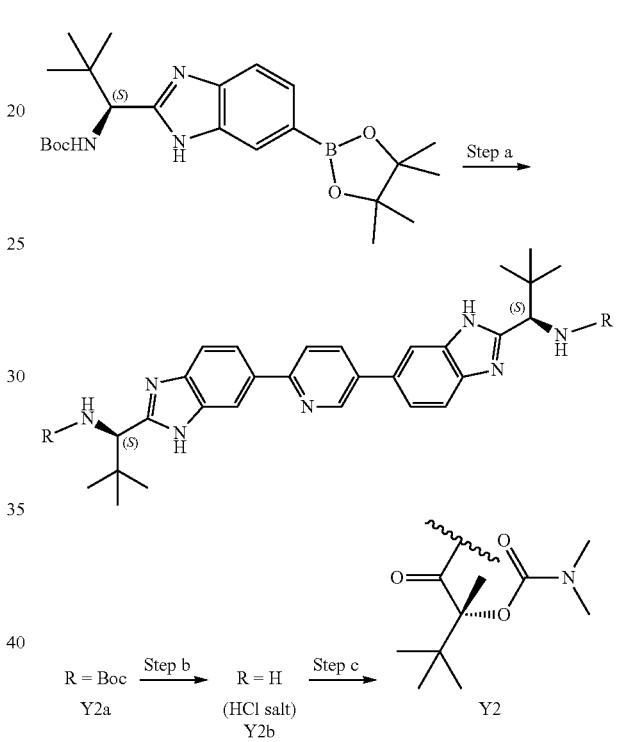

A mixture of (S)-tert-butyl (2,2-dimethyl-1-(6-(4,4,5,5-tetramethyl-1,3,2-dioxaborolan-2-yl)-1H-benzo[d]imidazol-2-yl)propyl)carbamate (0.55 g, 1.281 mmol), 2,5-dibromopyridine (0.12 g, 0.507 mmol) and sodium carbonate (0.40 g, 3.8 mmol) in dioxane (8 mL) and water (2 mL) was sparged with N$_2$ for 5 min. PdCl$_2$(dppf) (0.06 g, 0.082 mmol) was added and sparged with N$_2$ again. The reaction mixture was heated at 90° C. for 20 h and cooled down, diluted with EtOAc, washed with water and brine, dried (MgSO$_4$), and concentrated. The resultant crude material was purified by silica gel flash chromatography (20-70% EtOAc in hexanes) to afford carbamate Y2a (0.3 g) as beige solid. LC/MS (Condition 1b): R$_t$=2.67 min, [M+H]$^+$ 682.40.

HCl in dioxane (3 mL of 4 N, 12 mmol) was added to a solution of carbamate Y2a (0.25 g, 0.367 mmol) in DCM (3 mL) and the mixture was stirred at RT for 20 h. The mixture was evaporated in vacuo to afford the HCl salt of amine Y2b (0.231 g) as a beige solid. LC/MS (Condition 1b): R$_t$=2.77 min, m/z [M+H]$^+$ 482.35.
Step c:
Coupling the HCl salt of amine Y2b (0.053 g) with acid 2 according to the procedure described for Example Y1 afforded Example Y2. LC/MS (Condition 3): R$_t$=2.40 min, [M+H]$^+$ 880.54.

Example Y3 washed with water and brine, dried (MgSO$_4$) and concentrated in vacuo. The resultant crude material was purified by flash chromatography to afford coupled product Y3a (0.57 g) as beige solid. LC/MS (Condition 3): R$_t$=2.16 min, [M+H]$^+$ 707.40.

Carbamate Y3a was elaborated to Example Y3 according to the procedure described for the preparation of Example Y1 and Y2. LC/MS (Condition 3): R$_t$=2.37 min, [M+H]$^+$ 905.53.

Example Y4

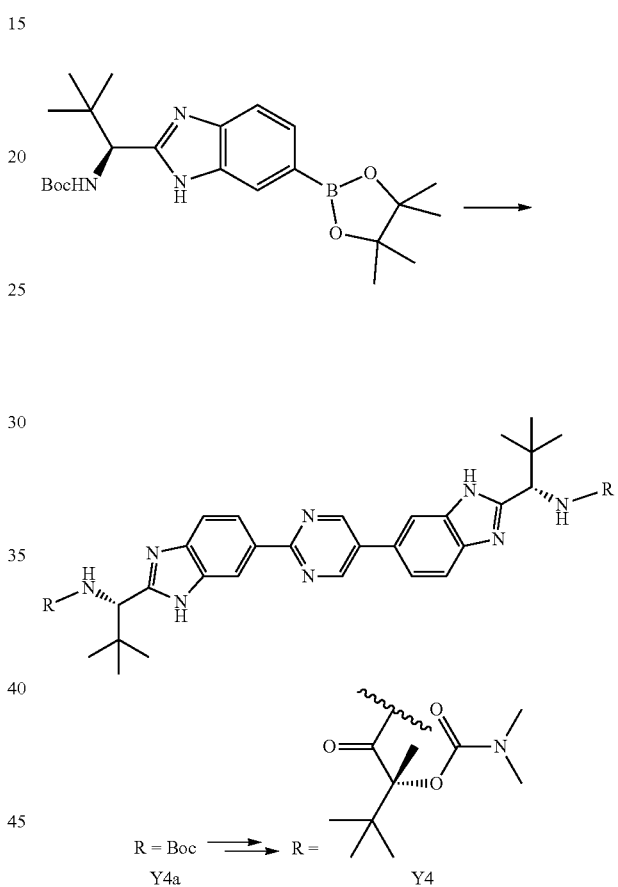

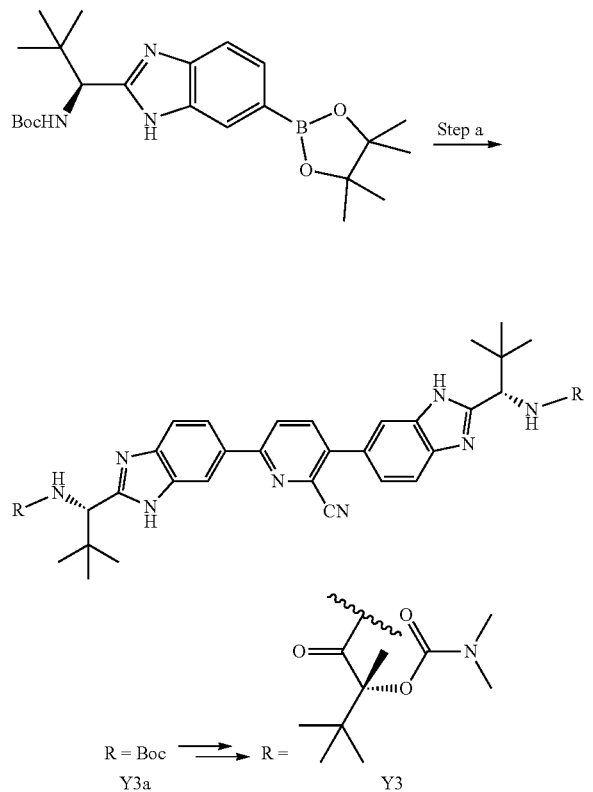

A mixture of (S)-tert-butyl (2,2-dimethyl-1-(6-(4,4,5,5-tetramethyl-1,3,2-dioxaborolan-2-yl)-1H-benzo[d]imidazol-2-yl)propyl)carbamate (0.80 g, 1.86 mmol), 5-bromo-2-chloropyrimidine (0.15 g, 0.775 mmol) and sodium carbonate (0.40 g, 3.8 mmol) in dioxane (8 mL) and water (2 mL) was spurged with N$_2$ for 5 min and then PdCl$_2$(dppf) (0.06 g, 0.082 mmol) was added and the mixture was heated at 90° C. for 2 days. It was then cooled down to RT, diluted with EtOAc, washed with water and brine, dried (MgSO$_4$), concentrated, and purified by flash chromatography (0 to 100% EtOAc/hexanes) to afford pyrimidine Y4a as brown solid (0.35 g). LC/MS (Condition 3): R$_t$=1.87 min, [M+H]$^+$ 683.9.

Carbamate Y4a was elaborated to Example Y4 according to the procedure described in the preparation of Example Y1 and Y2. LC/MS (Condition 3): R$_t$=2.37 min, [M+H]$^+$ 881.53.

A mixture of (S)-tert-butyl (2,2-dimethyl-1-(6-(4,4,5,5-tetramethyl-1,3,2-dioxaborolan-2-yl)-1H-benzo[d]imidazol-2-yl)propyl)carbamate (0.9 g, 2.1 mmol), 3,6-dichloropicolinonitrile (0.15 g, 0.867 mmol) and sodium carbonate (0.4 g, 3.77 mmol) in dioxane (8 mL) and water (2 mL) was spurged with nitrogen for 5 min before the addition of PdCl$_2$(dppf) (0.07 g, 0.096 mmol). The mixture was heated at 90° C. for 3 days and cooled to RT, diluted with EtOAc,

Example Y5

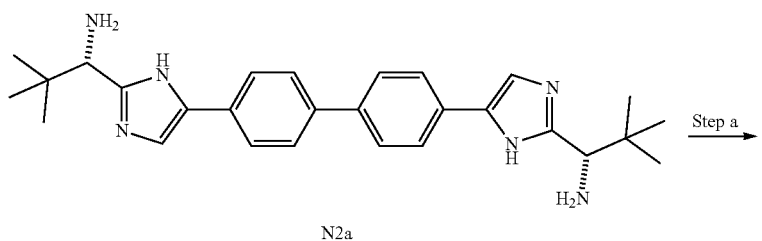

N2a

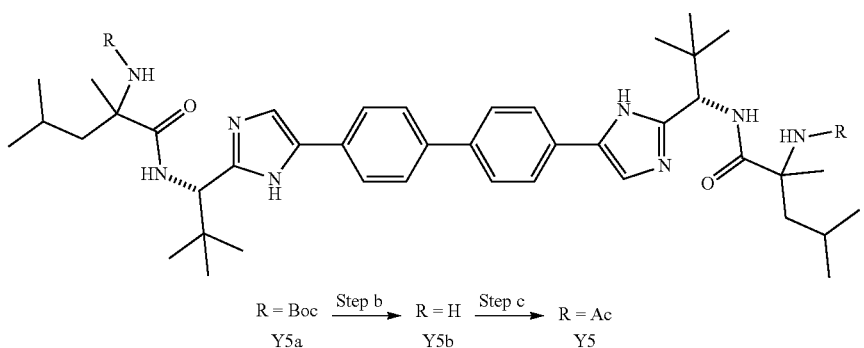

R = Boc  Step b  R = H  Step c  R = Ac
Y5a              Y5b             Y5

To a mixture of the HCl salt of N2a (0.50 g, 0.83 mmol) and 2-((tert-butoxycarbonyl)amino)-2,4-dimethylpentanoic acid (0.448 g, 1.826 mmol) in DCM (10 mL) was added DIPEA (1.16 mL, 6.64 mmol) and TBTU (0.586 g, 1.83 mmol) at 0° C. The reaction mixture was stirred at RT for 2 h, diluted with EtOAc, washed with satd. NaHCO$_3$, brine, dried (MgSO$_4$) and concentrated. The resultant crude material was purified by silica gel chromatography (0-50% EtOAc/hexanes) to afford amide Y5a (0.60 g, 0.66 mmol).

To a solution of amide Y5a (0.60 g, 0.66 mmol) in DCM (3 mL) was added a cold dioxane solution of 4 N HCl (3 mL, 12 mmol). The mixture was stirred at room for 1 h, and removal of volatile components in vacuo afforded amine Y5b/4 HCl (0.56 g). LC/MS: [M+H]$^+$ 711.55.

To a mixture of amine Y5b/4 HCl (30 mg, 0.036 mmol) in DCM (2 mL) was added DIEA (0.10 mL, 0.57 mmol) and acetyl chloride (0.01 mL, 0.14 mmol). The reaction mixture was stirred at RT for 1 h. It was then diluted with MeOH (1 mL) and after the volatile component was removed in vacuo the crude material was purified by prep HPLC (column: XBridge C18; CH$_3$CN/H$_2$O/NH$_4$OAc) to afford the three individual diastereomers of Example Y5. The most active isomer eluted first: $^1$H NMR (400 MHz, MeOH-d$_4$) δ 7.78 (d, J=8.3 Hz, 4H), 7.72 (d, J=8.3 Hz, 4H), 7.38 (s, 2H), 5.03 (s, 2H), 2.04 (s, 6H), 1.77-1.61 (m, 6H), 1.52 (s, 6H), 1.02 (s, 18H), 0.78 (d, J=6.4 Hz, 6H), 0.72 (d, J=6.6 Hz, 6H). LC/MS (Condition 3): R$_t$=1.89 min, 795.7 [M+H]$^+$.

Example Y6 to Y7

Example Y6 and Y7 were prepared from amine Y5b and appropriate acylchloride according to the procedure described in the preparation of Example Y5.

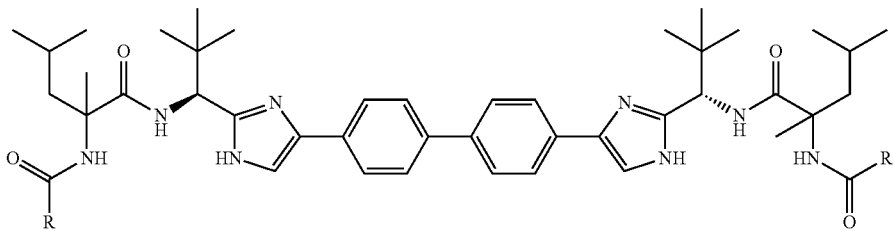

| Example | R | LC/MS Method | $R_t$ (min) | $(M + H)^+$ |
|---|---|---|---|---|
| Y6 | Et (Symmetrical diastereomer, 1st elute) | 3 | 2.33 | 823.9 |
| Y7 | FCH₂ (Symmetrical diastereomer, 1st elute) | 3 | 2.10 | 831.9 |

Example Y8 to Y11

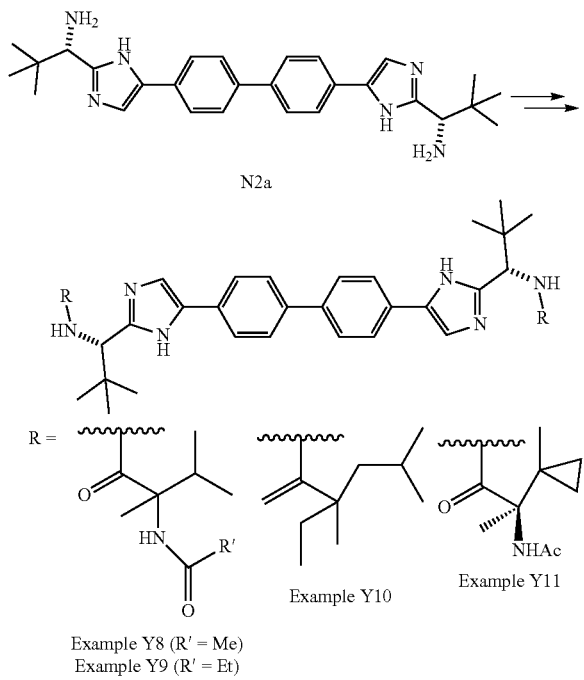

Example Y8 (R' = Me)
Example Y9 (R' = Et)

Example Y8 to Y11 were prepared from the HCl salt of N2a and appropriate precursors according to the procedure described for the synthesis of Example Y5.

Where applicable, the installation of the acetyl moiety was done either with AcCl as described for Example Y5 or with Ac₂O, which is well established in the art.

| Example | LC-MS Method | $R_t$ (min) | $(M + H)^+$ unless noted otherwise |
|---|---|---|---|
| Y8 (Symmetrical diastereomer, 1st elute) | 3 | 1.82 | 767.8 |
| Y9 (Symmetrical diastereomer, 1st elute) | 3 | 1.99 | 795.52 |
| Y10 (Symmetrical diastereomer, 1st elute) | 3 | 2.02 | 830.1 $(M - H)^-$ |
| Y11 (Symmetrical diastereomer, 1st elute) | 3 | 1.92 | 791.7 |

Example Y12

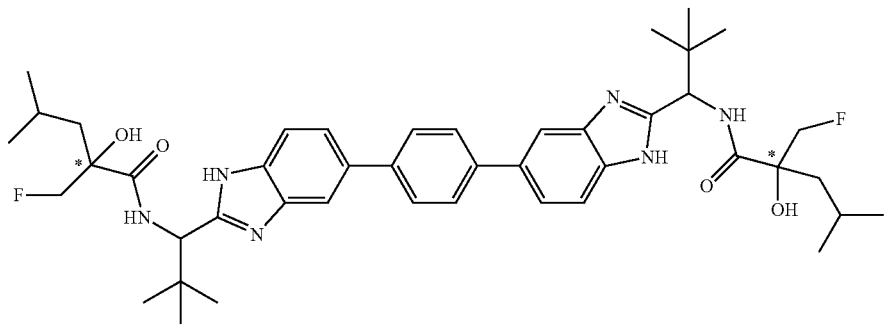 [SMILES: CC(C)CC(O)(CF)C(=O)NC(c1nc2cc(-c3ccc(-c4ccc5[nH]c(C(NC(=O)C(O)(CF)CC(C)C)C(C)(C)C)nc5c4)cc3)ccc2[nH]1)C(C)(C)C]

To a solution of the HCl salt of P3a (0.052 g, 0.083 mmol), acid 9b.1 (0.030 g, 0.183 mmol), and DIEA (0.116 mL, 0.664 mmol) in DMF (1.5 mL) was added HATU (0.066 g, 0.174 mmol). The reaction mixture was stirred at RT for 1 h. The reaction was diluted with MeOH (6.5 mL) and purified by reverse phase preparatory HPLC (Column: SunFire Prep C18 OBD; MeOH/H$_2$O/TFA) to afford the TFA salt of Example Y12 as tan solid (39.6 mg). $^1$H NMR (400 MHz, DMSO-d$_6$) δ 8.20 (app d, J=9.8 Hz, 2H), 8.01 (app br s, 2H), 7.87 (s, 4H), 7.81 (app d, J=8.3 Hz, 2H), 7.73 (app d, J=8.0 Hz, 2H), 6.13 (br s, 2H), 5.22 (app d, J=9.8 Hz, 2H), 4.48 (dd, J=9.0, 96.8 Hz, 2H), 4.36 (dd, J=9.0, 96.8 Hz, 2H), 1.76-1.58 (m, 2H), 1.51 (dd, J=13.8, 7.8 Hz, 2H), 1.35 (dd, J=13.9, 4.9 Hz, 2H), 1.01 (s, 18H), 0.78 (d, J=6.8 Hz, 6H), 0.47 (d, J=6.5 Hz, 6H). LC/MS (Condition 1): R$_t$=3.51 min, [M+H]$^+$ 773.18.

Example Y13

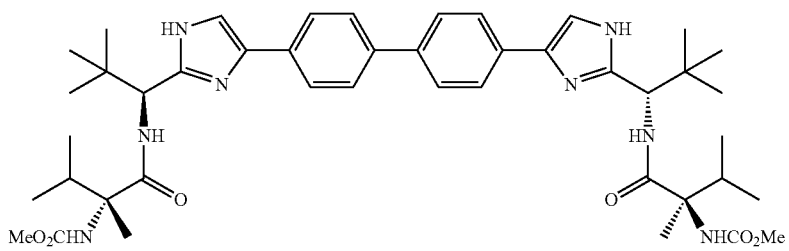

To a solution of the HCl salt of N2a (50 mg, 0.083 mmol) and acid 10 (34.5 mg, 0.183 mmol) in DMF (2 mL) were added DIEA (0.087 mL, 0.498 mmol) and HATU (64.7 mg, 0.170 mmol), and the mixture was stirred at RT for 2 h. The volatile component was removed in vacuo and the residue was purified by reverse phase prep HPLC (CH$_3$CN/H$_2$O/NH$_4$OAc) to afford Example Y13 as white solid (37.2 mg). LC/MS (Condition 1): R$_t$=3.40 min, [M+H]$^+$ 799.55.

Example Y14

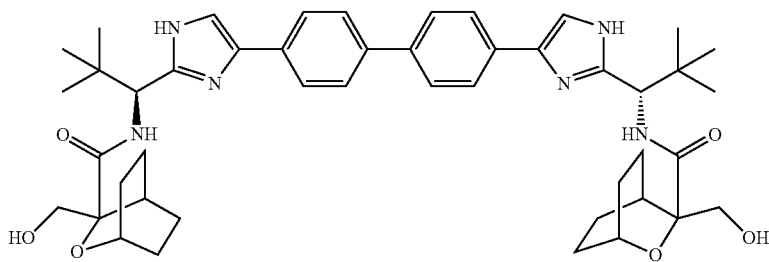 [SMILES: CC(C)(C)[C@H](NC(=O)C1(CO)OC2CCC1CC2)c1nc(-c2ccc(-c3ccc(-c4c[nH]c([C@@H](NC(=O)C5(CO)OC6CCC5CC6)C(C)(C)C)n4)cc3)cc2)c[nH]1]

To a solution of the HCl salt of N2a (50 mg, 0.083 mmol) and acid 11 (34.0 mg, 0.183 mmol) in DMF (2 mL) were added DIEA (0.094 mL, 0.539 mmol) and HATU (65.0 mg, 0.171 mmol), and the mixture was stirred at RT for 2 h. The volatile component was removed in vacuo and the residue was purified by reverse phase prep HPLC (X-Bridge C18; CH$_3$CN/H$_2$O/NH$_4$OAc; done twice at two different concentrations of NH$_4$OAc, 20 mM & 10 mM) to afford the three individual diastermers. The first elute (Example Y14), which was the most active isomer, was obtained as white solid (15.5 mg). $^1$H NMR (400 MHz, DMSO-d$_6$): δ 8.00-7.84 (m, 6H), 7.74-7.38 (m, 6H), 4.93-4.83 (m, 2H), 4.03 (m, 2H), 3.63 (m, 4H), 1.97-1.82 (m, 8H), 1.53-1.35 (m, 6H), 1.25-1.15 (m, 4H), 0.94 (s, 18H). LC/MS (Condition 2): R$_t$=4.04 min, [M+H]$^+$ 793.60.

Example Y15

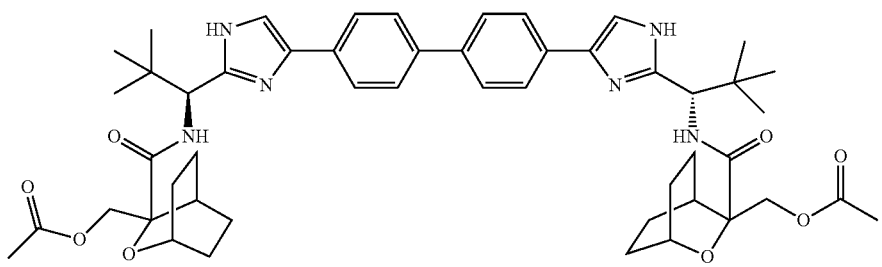 [SMILES: CC(=O)OCC1(C(=O)N[C@H](c2nc(-c3ccc(-c4ccc(-c5c[nH]c([C@@H](NC(=O)C6(COC(C)=O)OC7CCC6CC7)C(C)(C)C)n5)cc4)cc3)c[nH]2)C(C)(C)C)OC2CCC1CC2]

To a DCE (1.5 mL) suspension of Example Y14 (37 mg, 0.047 mmol) in a pressure tube was added acetyl chloride (0.50 mL, 7.0 mmol). The mixture was flushed with nitrogen and heated at 95° C. for 36 h. The volatile component was removed in vacuo and the residue was purified sequentially by two reverse phase prep HPLCs (MeOH/TFA/Water followed by CH$_3$CN/TFA/Water) to afford Example Y15 as white foam (19 mg). $^1$H NMR (400 MHz, MeOD): δ 8.30-8.17 (m, 2H), 8.01 (s, 2H), 7.91 (m, 8H), 5.32-5.25 (m, 2H), 4.65, J=12 Hz, 2H), 4.15 (d, J=12 Hz, 2H), 4.10 (m, 2H), 2.10-1.95 (m, 14H), 1.71-1.53 (m, 8H), 1.34 (m, 2H), 1.15 (s, 18H). LC/MS (Condition 1a): R$_t$=2.51 min, [M+H]$^+$ 877.25.

Example Y16A AND Y16B

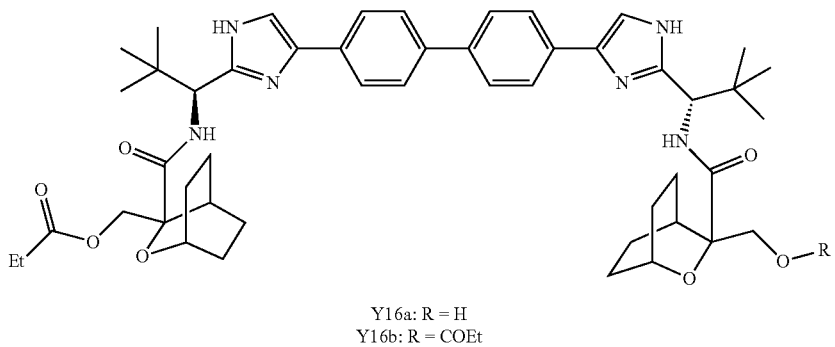

Y16a: R = H
Y16b: R = COEt

To a CH$_2$Cl$_2$ (2.5 mL) suspension of Example Y14 (64.4 mg, 0.081 mmol) in a pressure tube was added propionyl chloride (1.06 mL, 12.2 mmol), and the mixture was flushed with nitrogen, sealed and heated at 95° C. for 24 h. The volatile component was removed in vacuo and the residue was purified by reverse phase prep HPLC (MeOH/TFA/Water) to afford two fractions, both as TFA salts. Example Y16a (first elute, 3.7 mg, white foam): LC/MS (Condition 1a): R$_t$=2.92 min, [M+H]$^+$ 849.51. Example Y16b (second elute, 36.2 mg, white foam): LC/MS (Condition 2): R$_t$=3.12 min, [M+H]$^+$ 905.55.

Example Y17

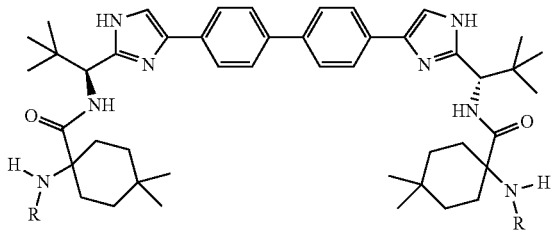

Y17a: R = Boc
Y17b: R = H
Y17: R = Ac

To a suspension of the HCl salt of N2a (102 mg, 0.169 mmol) and acid 12 (94 mg, 0.347 mmol) in DMF (5 mL) was added DIEA (0.237 mL, 1.354 mmol) and HATU (135 mg, 0.356 mmol), and the reaction mixture was stirred at RT for 1.5 h. The reaction mixture was diluted with EtOAc and washed with water and brine. The organic layer was the dried (MgSO$_4$), and concentrated under vacuum. An off-white solid corresponding to Example Y17a (160 mg) was recovered, which was used without further purification. LC/MS Anal. Calcd. for [M+H]$^+$ C$_{56}$H$_{83}$N$_8$O$_6$: 963.64; found 963.75.

HCl (4 M in dioxanes; 0.5 mL, 2.0 mmol) was added to a solution of Example Y17a (160 mg, 0.166 mmol) in DCM (5 mL) and the resulting mixture was stirred at RT for 3 h. Solvent was removed under reduced pressure and the residue was triturated with Et$_2$O. The solid was filtered, washed with Et$_2$O and dried under vacuum. A yellow solid corresponding the HCl salt of Example Y17b (120 mg) was isolated and used without further purification. LC/MS: Anal. Calcd. for [M+H]$^+$ C$_{46}$H$_{67}$N$_8$O$_2$: 763.54; found 763.65.

Acetyl chloride (0.026 mL, 0.358 mmol) was added to a solution of the HCl salt of Example Y17b (65 mg, 0.072 mmol) and DIEA (0.125 mL, 0.715 mmol) in DCM (1.5 mL). The mixture was stirred at RT for 2 h. After addition of NH$_3$ (2 M in MeOH; 0.5 mL, 1.000 mmol), the mixture was stirred at RT for 2 h. Solvent was evaporated under vacuum and residue was taken up in MeOH and purified by preparatory HPLC (Solvent: MeOH/H$_2$O/TFA; Column: Sunfire Prep C18). A solid corresponding to the TFA salt of Example Y17 (36 mg) was recovered as a white solid. $^1$H NMR (500 MHz, DMSO-d$_6$) δ 14.55 (br. s., 3H), 8.18 (br. s., 1H), 8.03-7.76 (m, 12H), 5.08 (br. s., 2H), 1.95-1.88 (m, 8H), 1.86-1.69 (m, 4H), 1.46-1.33 (m, 4H), 1.30-1.12 (m, 6H), 0.96 (s, 18H), 0.91 (s, 6H), 0.84 (s, 6H). LC (Condition 1C): R$_t$=2.21 min; Anal. Calcd. for [M+H]$^+$ C$_{50}$H$_{71}$N$_8$O$_4$: 847.56; found 847.80.

Example Y18

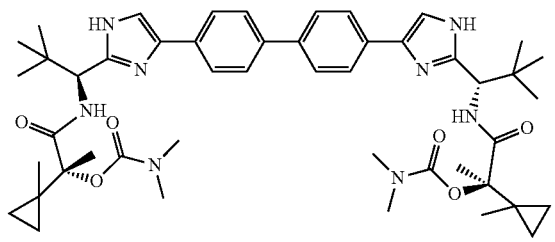 [SMILES: CN(C)C(=O)O[C@@](C)(C(=O)N[C@H](c1nc(-c2ccc(-c3ccc(-c4c[nH]c([C@@H](NC(=O)[C@](C)(OC(=O)N(C)C)C5(C)CC5)C(C)(C)C)n4)cc3)cc2)c[nH]1)C(C)(C)C)C1(C)CC1]

The HCl salt of N2a (1.65 g, 2.74 mmol), acid 13 (1.474 g, 6.85 mmol), HOAT (0.783 g, 5.75 mmol) and DIEA (3.83 mL, 21.91 mmol) were dissolved in DMF (30 mL). The mixture was sonicated until all solid content dissolved, followed by addition of EDC (1.103 g, 5.75 mmol). The reaction mixture was then stirred at RT for 24 h. The reaction mixture was then diluted with EtOAc (250 mL) and washed with sat. aq. NaHCO$_3$ (2×), water (2×) and brine, dried (MgSO$_4$), and concentrated under reduced pressure. The residue was purified by preparatory HPLC (Sunfire Prep MS C18; MeOH/H$_2$O/TFA) to afford the TFA salt of Example Y18 (1.134 g) as white solid. $^1$H NMR (500 MHz, DMSO-d$_6$) δ 8.20 (br. s., 2H), 7.93 (br. s., 8H), 7.34 (br. s., 2H), 5.26 (br. s., 2H), 2.90 (br. s., 6H), 2.78 (br. s., 6H), 1.58 (s, 6H), 1.13 (m, 2H), 0.96 (s, 18H), 0.86 (s, 6H), 0.69 (dt, J=9.8, 4.7 Hz, 2H), 0.27 (dt, J=9.3, 4.7 Hz, 2H), 0.16 (dt, J=9.5, 4.8 Hz, 2H). LC (Condition 4): R$_t$=1.02 min. LC/MS Anal. Calcd. for [M+H]$^+$ C$_{48}$H$_{67}$N$_8$O$_6$: 851.52; found 851.80.

Example Y19

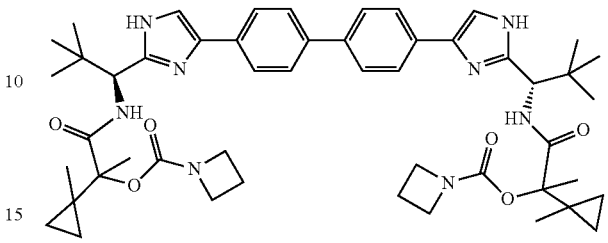

N-methylmorpholine (0.073 mL, 0.664 mmol) was added to a solution of the HCl of N2a (50 mg, 0.083 mmol), acid 14 (37.7 mg, 0.166 mmol) and HOAT (28.2 mg, 0.207 mmol) in DMF (2 mL) and after stirring for 5 min EDC (39.8 mg, 0.207 mmol) was added. The resulting solution was stirred at RT for 16 h. The crude reaction was purified by preparatory HPLC (H$_2$O/CH$_3$CN/NH$_4$OAc) to afford three stereoisomeric products, designated as diastereomers 1-3. The absolute stereochemistry of the symmetrical diastereomers were not determined and that the first elute (which is symmetrical diastereomer) was the most synergistically active of the three. LC/MS (Condition 5): [M+H]$^+$875.51, R$_t$=2.38 min.

Example Y20

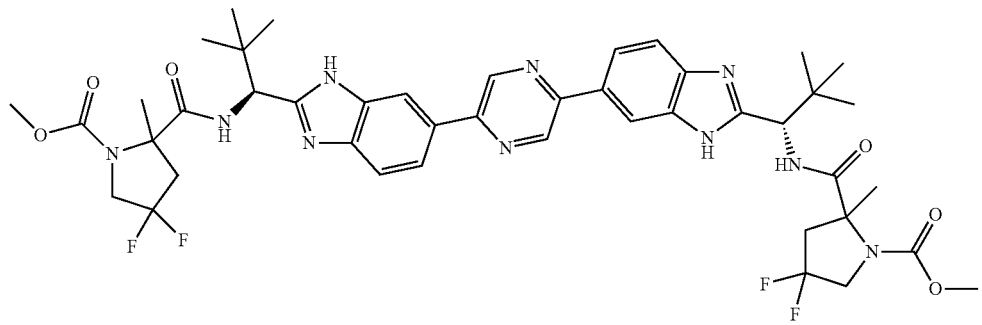

To a slurry of the HCl salt of P1b (100 mg, 0.150 mmol), acid 15 (70.5 mg, 0.316 mmol), and HATU (114 mg, 0.301 mmol) in DMF (1.2 mL) was added DIEA (0.236 mL, 1.354 mmol) and the resulting light yellow solution was stirred at RT for 2 h. The reaction mixture was then purified by preparatory HPLC (CH$_3$CN/H$_2$O/NH$_4$OAc) to afford three stereoisomeric products, and the first elute (which is symmetrical diastereomer) was the most synergistically active of the three. LC/MS (Condition 6): [M+H]$^+$ 893.7, R$_t$=2.03 min.

Example Y21

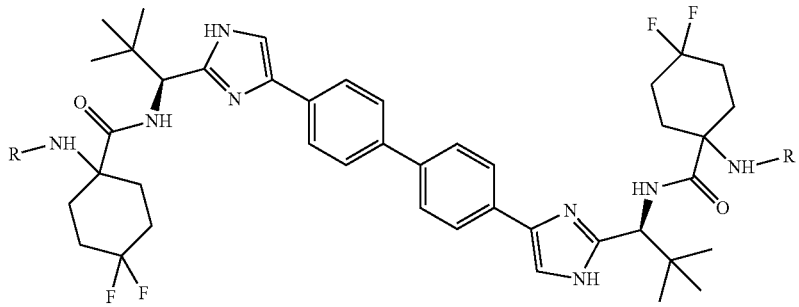

Y21a: R = Boc
Y21b: R = H
Y21: R = AC

This compound was prepared from the HCl salt of N2a and acid 16 by employing the procedures described for the synthesis of Example 8. The resulting product was purified by preparatory HPLC (MeOH/H$_2$O/TFA) affording the TFA salt of Y21a as yellowish solid. LC/MS: [M+H]$^+$979.9.

To a solution of carbamate Y21a/TFA salt (110 mg) in dioxane (1 mL) was added 4 N hydrogen chloride in dioxane (1.14 mL, 4.56 mmol), and the resultant mixture was stirred at RT overnight. The volatile component was removed in vacuo, and the residue was purified by prep-HPLC. The HPLC fraction was neutralized by sat. Na$_2$CO$_3$, and the solvent was concentrated in vacuo, and filtered. The filter cake was washed with water, and dried in vacuo to afford amine Y21b as white solid. LC/MS: [M+H]$^+$ 779.6.

To a solution of Y21b (52 mg, 0.067 mmol), DMAP (4.08 mg, 0.033 mmol) and DIEA (0.093 mL, 0.534 mmol) in DCM (1 mL) was added acetyl chloride (0.024 mL, 0.334 mmol) at RT. The solution was stirred at RT for 15 min followed by the addition of 2 N NH$_3$ in MeOH (1.34 mL, 2.67 mmol) and stirring at RT for 16 h. The reaction mixture was purified by preparatory HPLC (CH$_3$CN/H$_2$O/NH$_4$Ac) to afford Example Y21. $^1$H NMR (500 MHz, DMSO-d$_6$) δ 8.16 (s, 2H), 7.91-7.65 (m, 8H), 7.60-7.43 (m, 4H), 4.90-4.72 (m, 2H), 2.32 (d, J=5.5 Hz, 2H), 2.17-2.04 (m, 2H), 2.04-1.81 (m, 18H), 0.91 (s, 18H); LC/MS (Condition 1d): R$_t$=1.59 min, [M+H]$^+$ 863.8.

Example Y22

(R)-2-hydroxy-2,3,3-trimethylbutanoic acid (110 mg, 0.752 mmol) and HOAT (58 mg, 0.426 mmol) in anhydrous DMF (2.2 mL) is added N-methylmorpholine (210 µL, 1.91 mmol), followed by EDC (85.9 mg, 0.448 mmol). The reaction is flushed with N$_2$, securely capped and stirred at room temp for 18 h. The crude product is purified by reverse phase preparative HPLC conditions (TFA/MeOH/H$_2$O). The fractions containing the pure product are applied to a washed Waters Oasis MCX cartridge (part #186000777), and the cartridge is eluted with additional MeOH (40 mL), followed by 2.0 M NH$_3$/MeOH (20 mL). The solvent is removed to afford compound Y22a as a white solid (62.0 mg). $^1$H NMR (500 MHz, DMSO-d$_6$) δ 12.38-11.93 (m, 2H), 7.93-7.25 (m, 12H), 5.42 (s, 2H), 4.96-4.76 (m, 2H), 1.29 (s, 6H), 0.93 (s, 18H), 0.82 (s, 18H).

To a solution of compound Y22a (22.5 mg, 0.032 mmol) in anhydrous dioxane (2.0 mL) is added acetyl chloride (300 µL, 4.22 mmol). The reaction is flushed briefly with N$_2$, securely capped and heated to 90° C. for 18 h. The reaction is cooled to room temp, 1,2 dichloroethane (2 mL) and additional acetyl chloride (450 µL, 6.33 mmol) are added and the reaction is heated to 90-95° C. for 24 h. The crude product is purified by reverse phase preparative HPLC (TFA/H$_2$O/MeOH) to afford the TFA salt of Example Y22 as a white solid (15.0 mg). LC/MS: [M+H]$^+$755.6, [M−1]$^-$ 753.6. $^1$H NMR (500 MHz, MeOH-d$_4$) δ 8.42 (d, J=9.2 Hz, 1H), 7.98 (s, 1H), 7.94-7.84 (m, 9H), 7.24 (d, J=7.2 Hz, 1H),

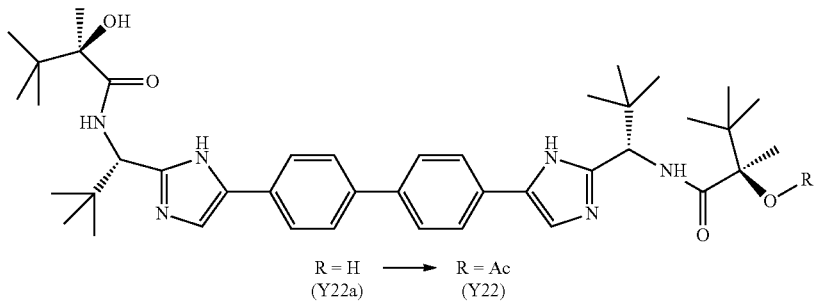

R = H → R = Ac
(Y22a)   (Y22)

To a solution of (1S,1'S)-1,1'-(5,5'-([1,1'-biphenyl]-4,4'-diyl))bis(1H-imidazole-5,2-diyl))bis(2,2-dimethylpropan-1-amine), 4.0 HCl (110 mg, 0.183 mmol) (see WO13106520), 5.25-5.20 (m, 1H), 5.13-5.07 (m, 1H), 2.05 (s, 3H), 1.79 (s, 3H), 1.42 (s, 3H), 1.13 (s, 9H), 1.12 (s, 9H), 1.06 (s, 9H), 0.96 (s, 9H).

Example B1

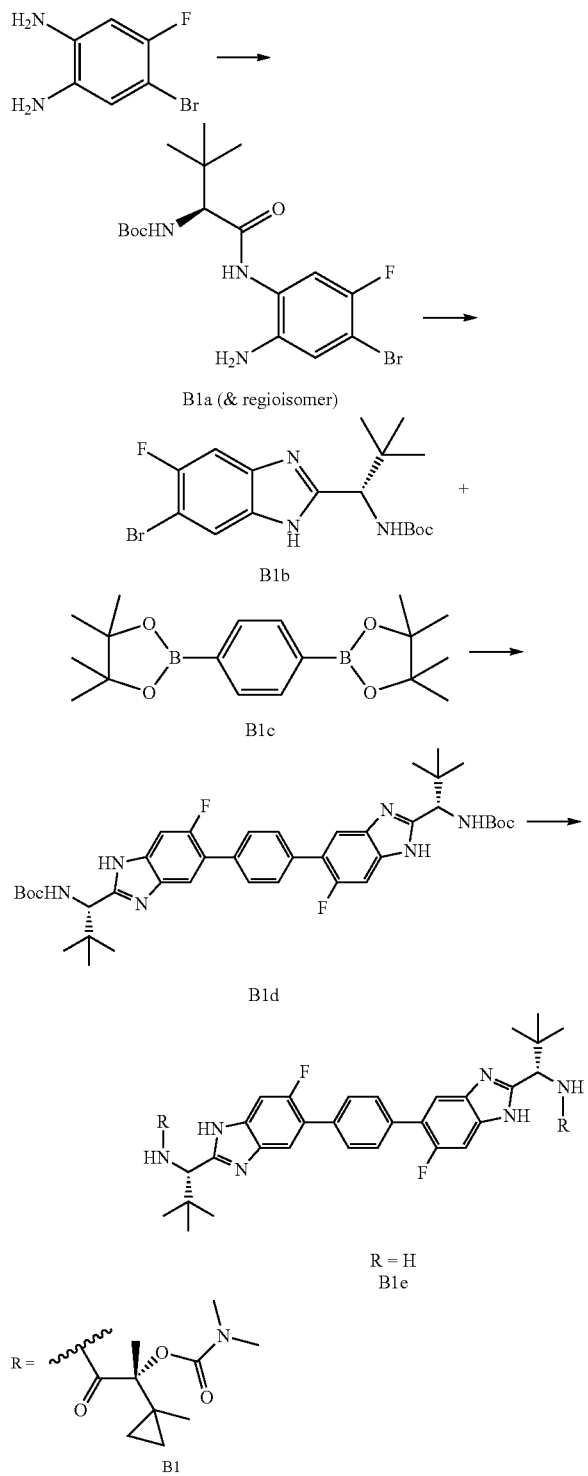

B1a (& regioisomer)

B1b

B1c

B1d

R = H
B1e

B1

To a solution of 4-bromo-5-fluorobenzene-1,2-diamine (4.50 g, 21.95 mmol), (S)-2-((tert-butoxycarbonyl)amino)-3,3-dimethylbutanoic acid (5.08 g, 21.95 mmol), DIPEA (3.83 mL, 21.95 mmol) in CH$_2$Cl$_2$ (200 mL) at 0° C. was added HATU (8.35 g, 21.95 mmol). The reaction mixture was stirred for 18 h at RT. After which, water (500 mL) was added into the reaction mixture and extracted with ethyl acetate (3×100 mL). The organic layer was washed with brine, dried (Na$_2$SO$_4$) and concentrated to afford B1a and/or ite regioisomer (10.0 g) as brown liquid. Crude was taken for next step without further purification. LC/MS: Anal. Calcd. for [M+H]$^+$ m\z C$_{17}$H$_{26}$BrFN$_3$O$_3$: 420.11; found 420.1.

The crude mixture of B1a (20.0 g, 23.91 mmol) was dissolved in AcOH (150 mL) and heated to 65° C. for 18 h. The reaction mixture was concentrated under reduced pressure, added water (100 mL) and extracted with ethyl acetate (3×50 mL). The combined organic layer was dried (Na$_2$SO$_4$) and concentrated. The resultant crude material was purified by ISCO (silica gel-60-120, eluted with 20% EtOAc/hexanes) to afford B1b (1.8 g) as pale yellow solid. $^1$H NMR (400 MHz, MeOH-d$_4$) δ ppm 7.78 (d, J=6.0 Hz, 2H), 7.40 (d, J=8.8 Hz, 2H), 4.67 (m, 1H), 2.01 (s, 2H), 1.39-1.50 (m, 9H), 0.99-1.11 (m, 9H). LC/MS: Anal. Calcd. For [M+H]$^+$ C$_{17}$H$_{24}$BrFN$_3$O$_2$: m/z 402.1; found 402.1.

To a degassed (with N$_2$) stirred solution of boronate B1c (0.701 g, 2.123 mmol), bromide B1b (1.7 g, 4.25 mmol), K$_2$CO$_3$ (1.76 g, 12.7 mmol) in 1,4-dioxane (35 mL) and H$_2$O (11 mL) was added Pd(dppf)Cl$_2$ (0.155 g, 0.212 mmol). The reaction mixture was purged with N$_2$ for 5 min, the vessel sealed and heated with microwave at 100° C. for 15 h. The reaction mixture was allowed to cool to RT, filtered, and the filtrate was concentrated under reduced pressure. The residue was dissolved in EtOAc (50.0 mL), washed with water (50.0 mL) and brine (50.0 mL), dried (Na$_2$SO$_4$) and concentrated under reduced pressure. The crude was purified by preparative HPLC (X-bridge phenyl; CH$_3$CN/H$_2$O/NH$_4$OAc) to afford B1d (0.3 g) as white solid. $^1$H NMR (400 MHz, MeOH-d$_4$) δ 7.68-7.65 (m, 6H), 7.39 (d, J=10.8 Hz, 2H), 5.08 (s, 2H), 1.46 (s, 18H) 1.06 (s, 18H). LC/MS: Anal. Calcd. for [M−H]$^-$ C$_{40}$H$_{49}$F$_2$N$_6$O$_4$: m\z 715.85; found 715.2.

HCl/Dioxane (4M; 10 mL, 30.0 mmol) was added to a solution of B1d (300 mg, 0.418 mmol) in MeOH (10.0 mL) at 0° C. and stirred at RT for 18 h. The reaction mixture was concentrated under reduced pressure and the residue was washed with diethyl ether (10.0 mL) to yield the HCl salt of B1e (0.25 g) as white solid. $^1$H NMR (400 MHz, MeOH-d$_4$) δ 7.79 (d, J=6.8 Hz, 2H), 7.71 (s, 4H), 7.53 (d, J=10.5 Hz, 2H), 4.46 (s, 1H), 1.19 (s, 9H). LC/MS: Anal. Calcd. for [M+H]$^+$ C$_{30}$H$_{35}$F$_2$N$_6$: m/z 517.64; found 517.3.

To a stirred solution of the HCl salt of B1e (70.0 mg, 0.106 mmol), acid 13 (114.0 mg, 0.528 mmol), and HATU (201 mg, 0.528 mmol) in DMF (5.0 mL) was added DIPEA (0.092 mL, 0.528 mmol) at RT under nitrogen atmosphere, and the mixture was heated at 40° C. for 18 h. The reaction mixture was concentrated under reduced pressure to remove DMF. The resultant crude material was diluted with EtOAc (50 mL), washed with aqueous ammonium chloride (25 mL), water (2×25 mL). The organic layer was dried (Na$_2$SO$_4$), and concentrated under reduced pressure. The obtained crude residue was purified by prep. HPLC (X-bridge phenyl; CH$_3$CN, H$_2$O/NH$_4$OAc) to afford Example B1 (18.0 mg) as white solid. LC (Condition 8) R$_t$=2.19 min. $^1$H NMR (400 MHz, MeOH-d$_4$) δ 7.69 (s, 6H), 7.42 (d, J=11.4 Hz, 2H), 7.12 (d, J=9.4 Hz, 1H), 5.11-5.17 (m, 2H), 3.04 (s, 6H), 2.93 (s, 6H), 1.70 (s, 6H), 1.16 (dt, J=10.0, 4.9 Hz, 2H), 1.05 (s, 18H), 0.92 (s, 6H), 0.77 (dt, J=10.0, 5.1 Hz, 2H), 0.28-0.36 (m, 2H), 0.15-0.25 (m, 2H). LC/MS Anal. Calcd. for [M+1]$^+$ C$_{50}$H$_{64}$F$_2$N$_8$O$_6$: m/z 911.09; Found: 912.2.

Example B2

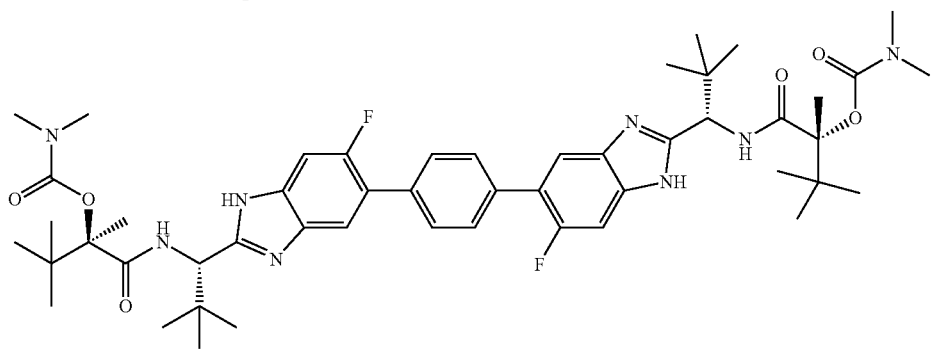 [SMILES: CN(C)C(=O)O[C@@](C)(C(=O)N[C@H](c1nc2cc(-c3ccc(-c4cc5nc([C@@H](NC(=O)[C@](C)(OC(=O)N(C)C)C(C)(C)C)C(C)(C)C)[nH]c5cc4F)cc3)c(F)cc2[nH]1)C(C)(C)C)C(C)(C)C]

To a stirred solution of the HCl salt of B1e (100.0 mg, 0.151 mmol), acid 2 (164.0 mg, 0.755 mmol), EDC (145.0 mg, 0.755 mmol), HOAT (1.258 mL, 0.755 mmol) in DMF (2.0 mL)) was added NMM (0.083 mL, 0.755 mmol). The mixture was flushed with nitrogen and heated at 65° C. for 18 h. The reaction mixture was concentrated under reduced pressure to remove DMF. The resultant crude was diluted with ethyl acetate (50.0 mL), washed with aqueous ammonium chloride (25 mL) and water (2×25 mL). The organic layer was dried ($Na_2SO_4$), and concentrated under reduced pressure. The resultant crude material was purified by prep. HPLC HPLC (X-bridge phenyl; $CH_3CN$, $H_2O/NH_4OAc$) to afford Example B2 (15.0 mg) as off white solid. LC/MS (Condition 8): $R_f$=2.25 min. $^1H$ NMR (400 MHz, MeOH-$d_4$) δ 7.65-7.76 (m, 5H), 7.61 (d, J=6.7 Hz, 1H), 7.45 (d, J=10.9 Hz, 1H), 7.36 (d, J=9.9 Hz, 1H), 7.14 (d, J=9.5 Hz, 2H), 5.14-5.23 (m, 2H) 3.14 (s, 6H), 2.96 (s, 6H), 1.72 (s, 6H), 1.06 (s, 18H), 1.00 (s, 18H). LC/MS: Anal. Calcd. for m/z $[M+H]^+$ $C_{50}H_{69}F_2N_8O_6$: 915.53: Found 916.2.

Example B3

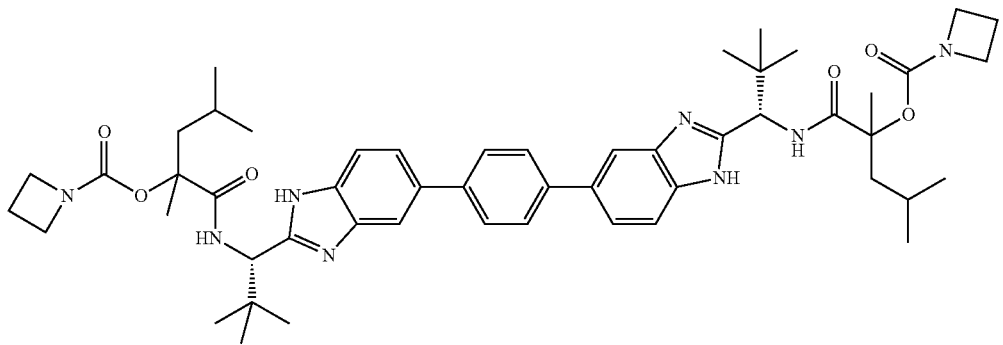 [SMILES: CC(C)CC(C)(OC(=O)N1CCC1)C(=O)N[C@H](c1nc2cc(-c3ccc(-c4ccc5[nH]c([C@@H](NC(=O)C(C)(CC(C)C)OC(=O)N6CCC6)C(C)(C)C)nc5c4)cc3)ccc2[nH]1)C(C)(C)C]

To a solution of the HCl salt of P3a (0.033 g, 0.048 mmol) in DMF (1.0 mL) was added 2-((azetidine-1-carbonyl)oxy)-2,4-dimethylpentanoic acid (single enantiomer of unknown stereochemistry; 0.044 g, 0.192 mmol), DIPEA (0.050 mL, 0.287 mmol) and HATU (0.038 g, 0.101 mmol). The reaction mixture was stirred at RT for 2 h. Reaction mixture was diluted with ethyl acetate, and washed with water, $NaHCO_3$ solution. The organic layer was dried ($Na_2SO_4$) and concentrated under reduced pressure. The crude mass was purified by preparative HPLC (Sunfire C18; $CH_3CN/H_2O/NH_4OAc$) to afford Example B3 (22 mg). LC/MS (Condition 7): $R_f$=2.69 min; Anal. Calcd. for m/z $[M+H]^+$ $C_{52}H_{71}N_8O_6$: 903.6; found 904.2. $^1H$ NMR (400 MHz, MeOH-$d_4$) δ 8.00 (s, 2H), 7.78-7.91 (m, 8H), 5.19 (s, 2H), 4.23 (bs, 4H), 4.00 (bs, 4H), 2.33 (quint, J=7.8 Hz, 4H), 1.85 (d, J=6.0 Hz, 4H), 1.64-1.80 (m, 8H) 1.09-1.22 (m, 18H), 0.77-0.92 (m, 12H).

Example B4

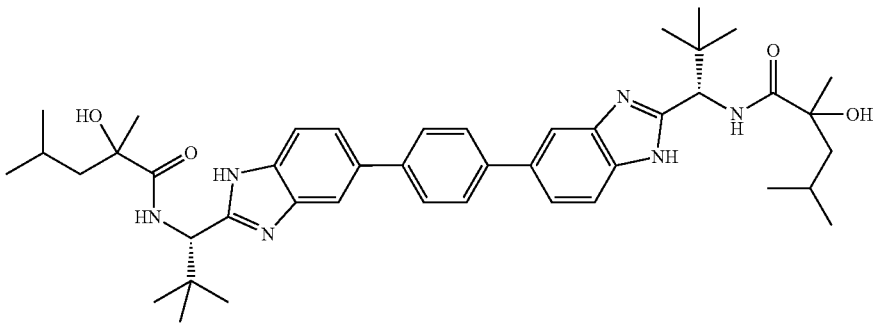 [SMILES: CC(C)CC(C)(O)C(=O)N[C@H](c1nc2cc(-c3ccc(-c4ccc5[nH]c([C@@H](NC(=O)C(C)(O)CC(C)C)C(C)(C)C)nc5c4)cc3)ccc2[nH]1)C(C)(C)C]

To a solution of the HCl salt of P3a (0.04 g, 0.064 mmol) in DMF (4 mL) was added DIPEA (0.067 mL, 0.383 mmol), 2-hydroxy-2,4-dimethylpentanoic acid (single enantiomer of unknown stereochemistry; 0.023 g, 0.160 mmol) and HATU (0.051 g, 0.134 mmol). The reaction mixture was stirred at RT for 2 h, diluted with water, and extracted with ethyl acetate. The organic phase was dried ($Na_2SO_4$) and concentrated. The resultant crude material was purified by preparative HPLC (Sunfire C18; $H_2O/CH_3CN$/TFA) to afford Example B4 (10.74 mg). LC/MS (Condition 8): $R_t$=2.15 min; Anal. Calcd. for m/z $[M+H]^+$ $C_{44}H_{61}N_6O_4$: 737.48; found 737.6. $^1$H NMR (400 MHz, MeOH-$d_4$) δ 8.00 (s, 2H), 7.78-7.91 (m, 8H), 5.19 (s, 2H), 4.23 (bs, 4H), 4.00 (bs, 4H), 2.33 (quint, J=7.8 Hz, 4H), 1.85 (d, J=6.0 Hz, 4H), 1.64-1.80 (m, 8H), 1.09-1.22 (m, 18H), 0.77-0.92 (m, 12H).

Example B5

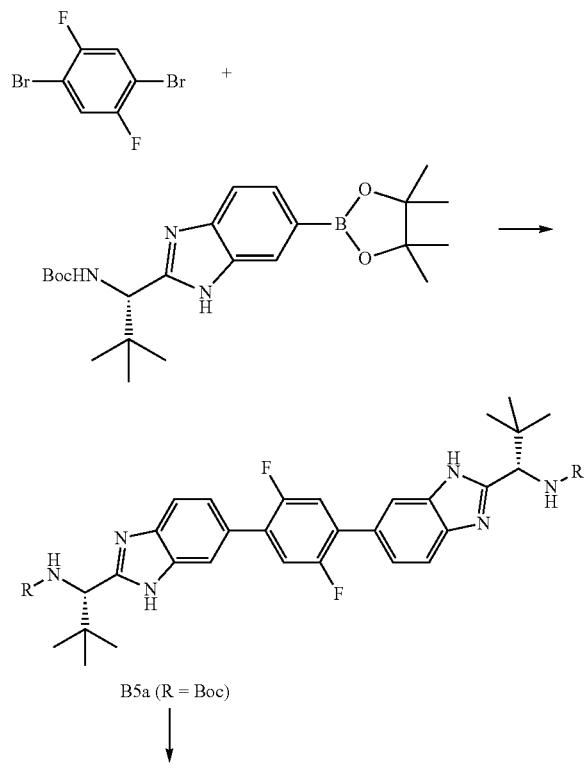

-continued

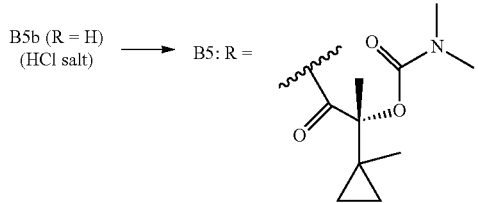

To a 250 mL pressure tube containing a stirred solution of 1,4-dibromo-2,5-difluorobenzene (1.0 g, 3.68 mmol) in dioxane (12 mL), ethanol (4.0 mL), and water (4.0 mL) were added (S)-tert-butyl(2,2-dimethyl-1-(5-(4,4,5,5-tetramethyl-1,3,2-dioxaborolan-2-yl)-1H-benzo[d]imidazol-2-yl) propyl) carbamate (3.32 g, 7.72 mmol) followed by $K_3PO_4$ (1.92 g, 11.0 mmol). The reaction mixture was then purged with nitrogen for 10 min, and then $PdCl_2$(dppf).$CH_2Cl_2$ (0.150 g, 0.184 mmol) was added and the mixture was heated at 90° C. for 16 h. The reaction mixture was cooled to RT, concentrated under reduced pressure to remove volatile component. The obtained crude was diluted with ethyl acetate, filtered on Celite, and the filtrate was washed with $H_2O$ (2×). The organic layer was dried ($Na_2SO_4$) and concentrated. The resultant crude product was first purified by ISCO (silica gel; 50% EtOAc/hexanes) and then submitted to preparative HPLC purification (Xbridge Phenyl C18; $CH_3CN/H_2O/NH_4OAC$) to afford carbamate B5a as yellow solid (0.15 g). LC/MS: Anal. Calcd. for m/z $[M+H]^+$ $C_{40}H_{51}F_2N_6O_4$: 717.4; found 717.4. $^1$H NMR (400 MHz, MeOH-$d_4$) δ 7.98 (s, 2H) 7.65 (dd, J=8.1, 1.0 Hz, 2H), 7.58-7.52 (m, 3H), 1.48-1.43 (m, 20H), 1.03 (s, 18H).

To a stirred solution of carbamate B5a (0.05 g, 0.07 mmol) in MeOH (10.0 mL) was added HCl/MeOH (15.0 mL, 45.0 mmol) at 0° C. under nitrogen atmosphere and stirred for 16 h at RT. The volatile component was removed under reduced pressure. To the obtained crude mass was added diethyl ether (20.0 mL) and stirred for 10 min. Then the diethyl ether was decanted and the same procedure was repeated twice. The obtained solid was dried under nitrogen to afford the HCl salt B5b as pale yellow solid (40 mg). LC/MS: Anal. Calcd. for m/z $[M+H]^+$ $C_{30}H_{35}F_2N_6$: 517.29; found, 517.4. $^1$H NMR (400 MHz, MeOH-$d_4$) δ 8.05 (s, 2H), 7.92 (d, J=8.6 Hz, 2H), 7.79 (d, J=8.7 Hz, 2H), 7.55 (t, J=8.7 Hz, 2H), 4.70 (s, 2H), 1.25-1.21 (m, 18H).

To a stirred solution of the HCl salt of B5b (0.05 g, 0.075 mmol) in DMF (5.0 mL) was added acid 13 (0.0487 g, 0.226 mmol), DIPEA (0.053 mL, 0.302 mmol) and HATU (0.0574 g, 0.151 mmol). The reaction mixture was stirred for 2 h at RT under $N_2$. The reaction mixture was concentrated under reduced pressure. The obtained crude residue was diluted with ethyl acetate (50.0 mL), washed with satd. aq. NH₄Cl (1×25 mL) and water (2×25 mL). The separated organic layer was dried (Na₂SO₄), filtered and concentrated under reduced pressure. The obtained crude reaction mixture was purified by preparative HPLC (Sunfire C18; CH₃CN/H₂O/TFA) to afford Example B5 as pale yellow solid (24.4 mg). LC/MS (Condition 8), $R_t$=2.19 min; Anal. Calcd. for m/z [M+H]⁺ $C_{50}H_{65}O_4F_2N_8O_6$: 911.50; found 912.2. ¹H NMR (400 MHz, MeOH-d₄) δ ¹H 7.99 (s, 2H), 7.90-7.84 (m, 2H), 7.81-7.76 (m, 2H), 7.54 (t, J=8.7 Hz, 2H), 5.10 (s, 2H), 2.80-2.97 (m, 14H), 1.72 (s, 6H), 1.14 (s, 20H), 0.98 (s, 6H), 0.85-0.77 (m, 2H), 0.35 (brs, 4H).

Example B6

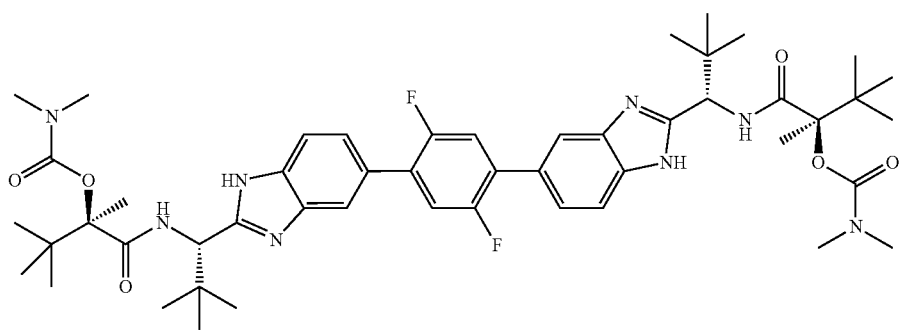 [SMILES: CN(C)C(=O)O[C@@](C)(C(=O)N[C@H](c1nc2cc(-c3cc(F)c(-c4ccc5[nH]c([C@@H](NC(=O)[C@](C)(OC(=O)N(C)C)C(C)(C)C)C(C)(C)C)nc5c4)cc3F)ccc2[nH]1)C(C)(C)C)C(C)(C)C]

To a solution of the HCl salt of B5b (0.06 g, 0.116 mmol) and acid 2 (0.126 g, 0.581 mmol) in DMF (2.0 mL) was added DIPEA (0.122 mL, 0.697 mmol) followed by HATU (0.097 g, 0.256 mmol) at 0° C. and the reaction mixture was stirred at RT for 2 h. Water (50 mL) was added and the reaction mixture was extracted with EtOAc (50 mL×2). The combined organic layer was washed with saturated aq. NH₄Cl, 10% NaHCO₃, water and brine. The organic layer was dried (Na₂SO₄) and concentrated under reduced pressure. The crude residue was purified by reverse phase HPLC (ACN/water/NH₄OAC) to afford Example B6 (8.0 mg) as an off-white solid. LC/MS: Anal. Calcd. for [M+H]⁺ $C_{50}H_{69}F_2N_8O_6$: m/z 915.5; found 916.2. ¹H NMR (400 MHz, MeOH-d₄) δ 7.90 (s, 1H), 7.79-7.73 (m, 2H), 7.61 (s, 1H), 7.56 (bs, 2H), 7.46 (d, J=8.5 Hz, 2H), 5.23 (s, 2H), 4.59-4.57 (m, 1H), 3.37 (s, 3H), 3.12 (s, 6H), 2.97 (s, 6H), 1.72 (s, 6H), 1.31 (s, 1H), 1.07 (s, 18H), 1.00 (s, 18H).

Example B7

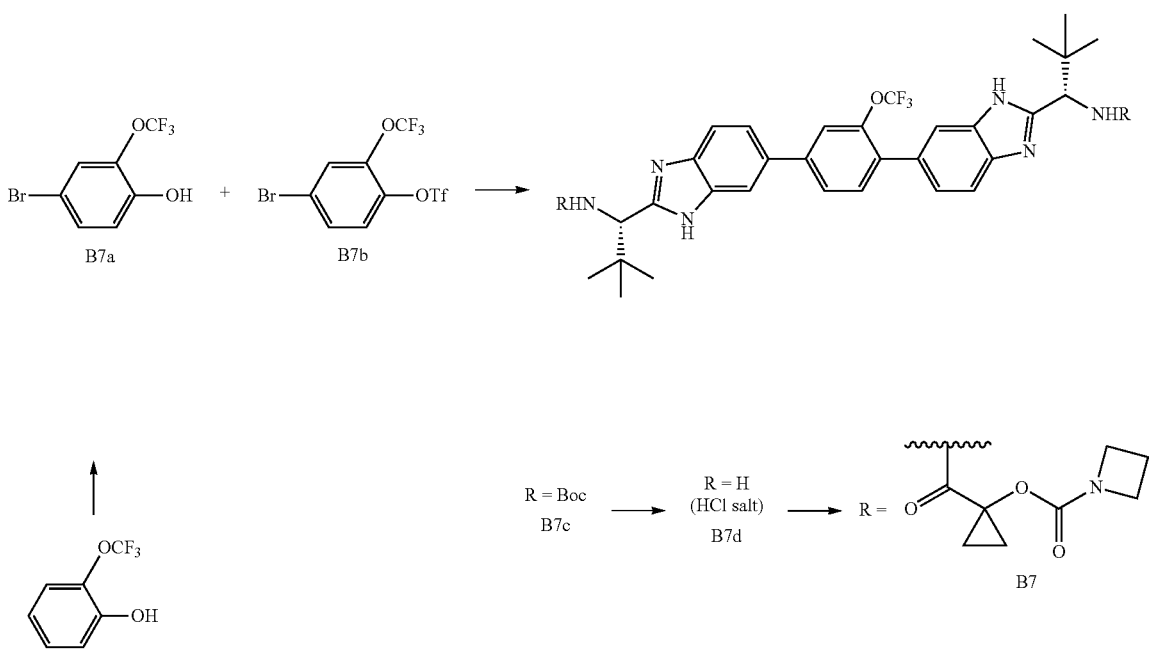

To a solution of 2-(trifluoromethoxy)phenol (5 g, 28.1 mmol) in $CH_2Cl_2$ (50 mL) at −78° C. was added a bromine (1 M in $CH_2Cl_2$, 30.4 mL, 30.4 mmol) drop wise over 20 min. The reaction was allowed to warm to ambient temperature and stirred for 48 h. Saturated $Na_2SO_3$ (100 mL) solution was added and the reaction mixture was stirred vigorously until disappearance of the orange color was observed. The biphasic mixture was diluted with $CH_2Cl_2$ (50 mL), and the organic layer was separated, washed with brine (50 mL), dried over $Na_2SO_4$, and concentrated in vacuum to give phenol B7a (6.2 g) as a pale yellow solid. $^1$H NMR (400 MHz, $CDCl_3$) δ 6.95 (d, J=8.7 Hz, 1H), 7.33 (dd, J=8.7, 2.3 Hz, 1H), 7.38 (d, J=8.8 Hz, 1H).

To a solution of phenol B7a (6.2 g, 24.12 mmol) in $CH_2Cl_2$ (50 mL) at 0° C. was added a pyridine (3.90 mL, 48.2 mmol) and followed by trifluoromethanesulfonic anhydride (6.11 mL, 36.2 mmol) dropwise over 10 min. The reaction mixture was allowed to warm to ambient temperature and stirred for 12 h. Water (50 mL) was added and the reaction mixture stirred for 10 min. The organic layer was separated and washed with water (2×) and brine, dried ($Na_2SO_4$) and concentrated in vacuo to afford triflate B7b (9 g). $^1$H NMR (400 MHz, $CDCl_3$) 7.30 (d, J=8.9 Hz, 1H), 7.53 (dd, J=8.9, 2.3 Hz, 1H), 7.59 (dq, J=2.4, 1.4 Hz, 1H).

$N_2$ was purged for 10 minutes through a stirred solution of (S)-tert-butyl (2,2-dimethyl-1-(6-(4,4,5,5-tetramethyl-1,3,2-dioxaborolan-2-yl)-1H-benzo[d]imidazol-2-yl)propyl) carbamate (4.86 g, 11.31 mmol) and trifltae B7b (2.0 g, 5.14 mmol) and cesium carbonate (6.70 g, 20.56 mmol) in dioxane (20 mL) and $H_2O$ (5 mL). $PdCl_2(dppf).CH_2Cl_2$ (0.210 g, 0.257 mmol) was added and purged with $N_2$ for additional 5 min. The reaction mixture was heated at 90° C. in sealed tube for 12 h. The reaction mixture was filtered and the filtrate was concentrated under reduced pressure. The residue was dissolved in EtOAc, washed with water and brine, dried ($Na_2SO_4$) and concentrated under reduced pressure. The crude was purified by preparative HPLC ($H_2O$/$NH_4OAc/CH_3CN$) to yield compound B7c as pale yellow solid (900 mg). LC/MS: Anal. Calcd. for $[M+H]^+$ $C_{41}H_{52}F_3N_6O_5$: 765.4; found 765.4. $^1$H NMR (400 MHz, MeOH-d$_4$) δ 7.79-7.86 (m, 1H) 7.56-7.79 (m, 7H) 7.39-7.44 (m, 1H) 4.72-4.76 (m, 2H) 1.44 (d, J=0.38 Hz, 19H) 1.02-1.08 (m, 18H).

HCl/MeOH (4M; 30 mL, 30.0 mmol) was added to a solution of carbamate B7c (850 mg, 1.111 mmol) in MeOH (10 mL) at 0° C. and stirred at RT for 12 h. The reaction mixture was concentrated under reduced pressure and the residue was co-evaporated with DCM (3×) to yield the HCl salt of B7d as a pale yellow solid (780 mg). LC/MS: Anal. Calcd. for $[M+H]^+$ $C_{31}H_{36}F_3N_6O$: 565.29; found 565.6. $^1$H NMR (400 MHz, MeOH-d$_4$) δ8.07-8.12 (m, 2H) 7.83-7.99 (m, 4H) 7.68-7.80 (m, 3H) 4.71 (s, 2H) 1.17-1.29 (m, 18H).

To a solution of the HCl salt of B7d (40 mg, 0.063 mmol) and 1-((azetidine-1-carbonyl)oxy)cyclopropanecarboxylic acid (29.0 mg, 0.157 mmol) in DMF (5 mL) at 0° C. was added DIPEA (0.044 mL, 0.251 mmol) followed by HATU (48.9 mg, 0.129 mmol). The reaction mixture was warmed to RT and stirred for 2 h. The reaction mixture was diluted with DCM, washed with saturated $NH_4Cl$ solution, 10% $NaHCO_3$ solution, water and brine. The organic layer was dried ($Na_2SO_4$) and concentrated in vacuo. The crude was purified by preparative HPLC ($NH_4OAc/CH_3CN/H_2O$) to yield B7 (28 mg) as a white solid. LC/MS (Condition 10): $R_t$=2.19 min; LC/MS: Anal. Calcd. for $[M+H]^+$ $C_{47}H_{54}F_3N_8O_7$: 899.41; found 899.8. $^1$H NMR (400 MHz, MeOH-d$_4$) δ7.75-7.81 (m, 2H) 7.59-7.70 (m, 5H) 7.41-7.47 (m, 2H) 5.18 (s, 1H) 4.02-4.57 (m, 8H) 2.32-2.39 (m, 4H) 1.96-2.05 (m, 1H) 1.63 (m, J=14.18, 4.77 Hz, 2H) 1.12-1.30 (m, 7H) 1.06 (d, J=1.63 Hz, 18H).

Example B8

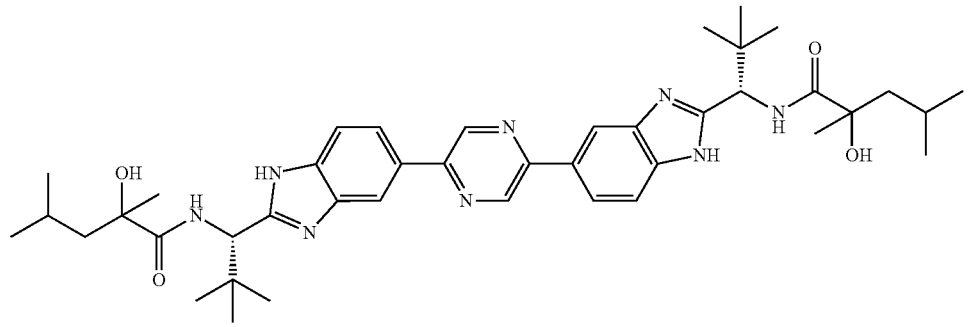 [SMILES: CC(C)CC(C)(O)C(=O)N[C@H](c1nc2cc(-c3cnc(-c4ccc5[nH]c([C@@H](NC(=O)C(C)(O)CC(C)C)C(C)(C)C)nc5c4)cn3)ccc2[nH]1)C(C)(C)C]

To a solution of the HCl salt of P1b (40 mg, 0.072 mmol) and 2-hydroxy-2,4-dimethylpentanoic acid (single enantiomer of unknown stereochemistry; 26.3 mg, 0.180 mmol) in DMF (5 mL) at 0° C. was added DIPEA (0.050 mL, 0.288 mmol) followed by HATU (56.1 mg, 0.148 mmol). The reaction mixture was warmed to RT and stirred for 2 h. It was then diluted with DCM, washed with saturated $NH_4Cl$ solution, 10% $NaHCO_3$ solution, water and brine. The organic layer was dried ($Na_2SO_4$) and concentrated under reduced pressure. The crude was purified by preparative HPLC ($TFA/CH_3CN/H_2O$) to yield the TFA salt of Example B8 as a white solid (15 mg). LC/MS (Condition 10): $R_t$=1.94 min; Anal. Calcd. for $[M+H]^+$ $C_{42}H_{59}N_8O_4$: 739.5; found 739.6. $^1$H NMR (400 MHz, MeOH-d$_4$) □ 9.22 (s, 2H) 8.42 (s, 1H), 8.29 (s, 1H), 8.07 (d, J=8.66 Hz, 2H) 7.80 (s, 1H), 7.66 (s, 1H), 5.20 (s, 2H) 2.20 (s, 6H) 1.95 (m, J=14.34, 5.24 Hz, 2H) 1.78 (m, J=7.03 Hz, 2H) 1.68 (s, 7H) 1.55-1.65 (m, 2H) 1.05 (s, 18H) 0.74 (d, J=6.65 Hz, 6H) 0.68 (d, J=6.65 Hz, 6H).

Example B9

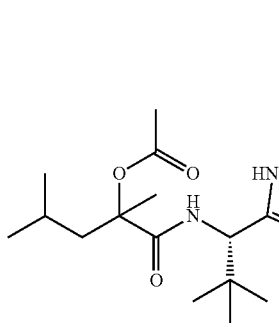

To a solution of the HCl salt of P1b (40 mg, 0.072 mmol) and 2-acetoxy-2,4-dimethylpentanoic acid (single enantiomer of unknown stereochemistry, 33.9 mg, 0.180 mmol) in DMF (5 mL) at 0° C. was added DIPEA (0.050 mL, 0.288 mmol) followed by HATU (56.1 mg, 0.148 mmol). The reaction mixture was warmed to RT and stirred for 2 h. The reaction mixture was diluted with DCM, washed with saturated NH$_4$Cl solution, 10% NaHCO$_3$ solution, water and brine. The organic layer was dried (Na$_2$SO$_4$) and concentrated under reduced pressure. The crude was purified by preparative HPLC (NH$_4$OAc/CH$_3$CN/water) to yield Example B9 as a white solid (12 mg). LC/MS (Condition 10): R$_t$=2.12 min; Anal. Calcd. for [M+H]$^+$ C$_{46}$H$_{63}$N$_8$O$_6$: 823.49; found 823.6. $^1$H NMR (400 MHz, MeOH-d$_4$) δ 9.30 (s, 2H) 8.49 (d, J=0.94 Hz, 2H) 8.27 (dd, J=8.69, 1.60 Hz, 2H) 7.85 (dd, J=8.60, 0.44 Hz, 2H) 5.20 (s, 2H) 1.67-1.77 (m, 4H) 1.45-1.51 (m, 2H) 1.41 (s, 6H) 1.13 (s, 18H) 0.84 (d, J=6.53 Hz, 6H) 0.55 (d, J=6.27 Hz, 6H).

Example B10

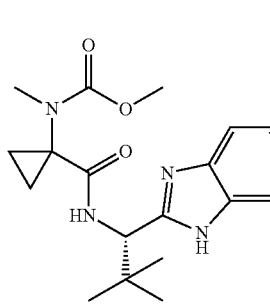

To a solution of the HCl salt of P3a (0.04 g, 0.064 mmol) in DMF (5 mL) was added DIPEA (0.067 mL, 0.383 mmol), 1-((methoxycarbonyl)(methyl)amino) cyclopropanecarboxylic acid (0.028 g, 0.160 mmol) and HATU (0.051 g, 0.134 mmol). Reaction mixture was allowed to stir at RT for 2 h. The reaction mixture was diluted with water and extracted with DCM, dried (Na$_2$SO$_4$) and concentrated. The crude material was purified by preparative HPLC (NH$_4$OAc/CH$_3$CN/H$_2$O) to afford Example B10 (20.29 mg). LC/MS (Condition 9): R$_t$=1.98 min; Anal. Calcd. For [M+H]$^+$ C$_{44}$H$_{55}$N$_8$O$_6$: 791.4; found, 791.6. $^1$H NMR (400 MHz, MeOH-d$_4$) □ 7.76 (s, 7H), 7.61 (d, J=6.8 Hz, 3H), 5.20 (s, 2H), 3.89-3.65 (m, 5H), 3.06 (s, 6H), 1.68-1.45 (m, 4H), 1.26 (br. s., 4H), 1.06 (s, 18H).

Biological Activity

The NS5A synergistic inhibitory effect of test compounds can be determined using various amounts of an NS5A-targeting compound with titration of a second compound of interest. Both the NS5A-targeting compound and the second compound of interest, demonstrate enhanced activity towards HCV strains when tested together verses when tested individually. In one embodiment, compound BMS-790052, as an NS5A-targeting compound, can be held constant at a fixed concentration of 200 nM with subsequent titration of the test compound on a variant of HCV. In one embodiment, the HCV genotype strain can be genotype 1a containing a change at amino acid 30 of the NS5A protein consisting of glutamine to glutamate or from a genotype 1a containing a change at amino acid 93 consisting of tyrosine to asparagine or from a genotype 3a containing a change at amino acid 93 consisting of tyrosine to asparagine. The test compound can be chosen from compounds listed above or from others present in the literature. One skilled in the art can readily test compounds in the HCV replicon cell based assay as has been demonstrated previously in the art and one can readily determine the effective concentration for 50% inhibition (EC$_{50}$) of a particular compound.

For illustration, Compound P-55 (see US 2015-0023913 A1 for its structure) can be titrated in the HCV replicon cell-based assay consisting of the genotype-1a variant with glutamine 30 changed to glutamate in the NS5A protein. Titration of BMS-790052 singly would yield an EC$_{50}$ value ~200 nM while titration of P-55 singly would yield an EC$_{50}$ value >200 nM. The titration of P-55 in the presence of a fixed amount of BMS-790052 at 200 nM afforded an $EC_{50}$ values of ~2 nM for P-55 demonstrating a synergistic inhibitory effect with the combination of >100-fold. Similarly, the titration of BMS-790052 in the presence of a fixed amount of P-55 at 200 nM afforded an $EC_{50}$ values of ~2 nM for BMS-790052, demonstrating a reciprocal synergistic inhibitory effect ~100-fold for the combination (PCT/US2011/043785, filed Jul. 13, 2011, Table 3). Additional compounds can be tested in a similar manner and a ranking of synergist activities determined. The synergistic $EC_{50}$ for the genotype 3a Y H variant in the presence of 200 nM of BMS-790052, with and without 40% human serum, are shown in the table below.

It is understood that the genotype is not limited to the genotype 3a variant but can encompass all genotypic variants of HCV including but not limited to HCV variants of 1a, 1b, 2a, 4a, 5a, 6a as demonstrated in PCT/US2011/043785, filed Jul. 13, 2011. It is also understood that the synergy effect is not limited to BMS-790052 or P-55 combinations but can be derived from other combinations of NS5A targeting compounds that by themselves have reduced or no potency towards HCV variants.

| Example | GT-3aY93H Synergy $EC_{50}$ (+200 nM BMS-790052) | GT-3aY93H Synergy $EC_{50}$ (+200 nM BMS-790052 + 40% HS) |
|---|---|---|
| N1 | 1.30E−06 | 1.13E−04 |
| N2 | 6.35E−06 | 3.08E−04 |
| N3 | 1.06E−06 | 7.14E−05 |
| N4 | 8.36E−06 | 3.80E−04 |
| N5 | 9.96E−06 | 3.67E−04 |
| N6 | 3.51E−06 | 1.86E−04 |
| N7 | 5.84E−06 | 3.52E−04 |
| N8 | 1.42E−05 | 4.57E−04 |
| N9 | 4.34E−06 | 4.61E−04 |
| P1 | 1.11E−05 | 4.48E−04 |
| P2 | 2.02E−06 | 8.98E−05 |
| P3 | 1.74E−06 | 4.29E−05 |
| P4 | 1.45E−06 | 7.94E−05 |
| P4a | 7.36E−05 | 6.05E−03 |
| P5 | 4.88E−06 | 3.18E−04 |
| P6 | 2.82E−06 | 2.35E−04 |
| P7 | 2.65E−06 | 8.85E−05 |
| P8 | 1.30E−06 | 3.36E−05 |
| P9 | 1.43E−05 | 3.50E−04 |
| P10 | 1.47E−05 | 3.68E−04 |
| P11 | 1.43E−05 | 2.57E−04 |
| P12 | 9.60E−06 | 9.69E−04 |
| P13 | 3.01E−06 | 1.87E−04 |
| P14 | 5.16E−06 | 2.73E−04 |
| P15 | 3.23E−06 | 3.87E−04 |
| Y1 | 6.67E−06 | 2.63E−04 |
| Y2 | 2.94E−06 | 2.33E−04 |
| Y3 | 2.94E−06 | 1.36E−04 |
| Y4 | 1.02E−06 | 7.54E−05 |
| Y5 | 1.46E−05 | 2.68E−04 |
| Y6 | 1.77E−05 | 5.19E−04 |
| Y7 | 7.73E−06 | 6.18E−04 |
| Y8 | 8.60E−06 | 3.16E−04 |
| Y9 | 3.15E−05 | 2.19E−04 |
| Y10 | 3.55E−06 | 4.39E−05 |
| Y11 | 4.52E−06 | 6.84E−05 |
| Y12 | 2.57E−06 | 8.18E−05 |
| Y13 | 1.87E−05 | 6.44E−04 |
| Y14 | 6.91E−06 | 1.10E−04 |
| Y15 | 2.34E−05 | 3.93E−04 |
| Y16a | 1.49E−05 | 6.44E−04 |
| Y16b | 2.16E−05 | 4.47E−04 |
| Y17 | 1.34E−05 | 2.50E−04 |
| Y18 | 3.41E−06 | 1.55E−04 |
| Y19a | 2.23E−06 | 8.03E−05 |
| Y20 | 4.67E−06 | 4.10E−04 |
| Y21 | 8.38E−06 | 2.57E−04 |
| Y22 | 1.29E−05 | 6.46E−04 |
| B1 | 7.38E−06 | 3.17E−04 |
| B2 | 4.02E−06 | 2.89E−04 |
| B3 | 9.60E−06 | 3.11E−04 |
| B4 | 7.56E−06 | 3.04E−04 |
| B5 | 1.85E−06 | 8.51E−05 |
| B6 | 1.12E−06 | 4.26E−05 |
| B7 | 2.32E−05 | 6.59E−04 |
| B8 | 2.42E−06 | 8.96E−05 |
| B9 | 3.55E−06 | 1.43E−04 |
| B10 | 1.02E−05 | 3.19E−04 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is BMS-790052, or a pharmaceutically acceptable salt thereof, and wherein the NS5A synergist is a compound selected from:

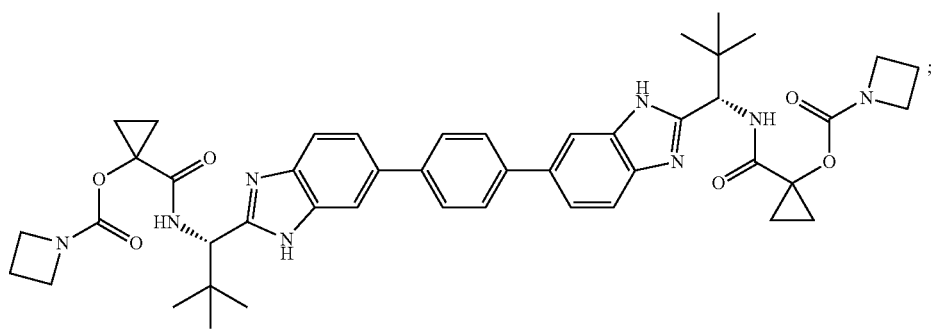

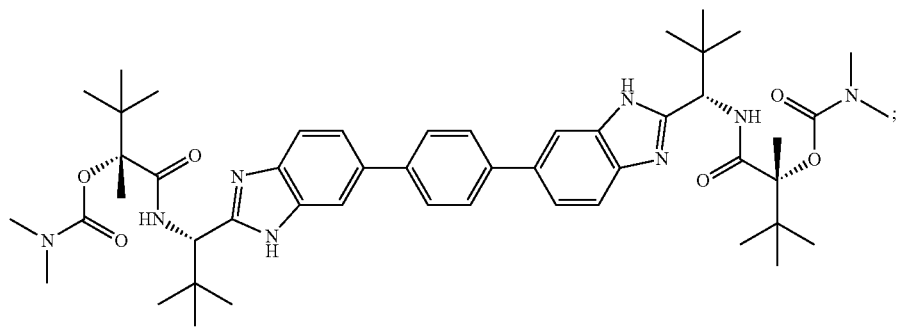
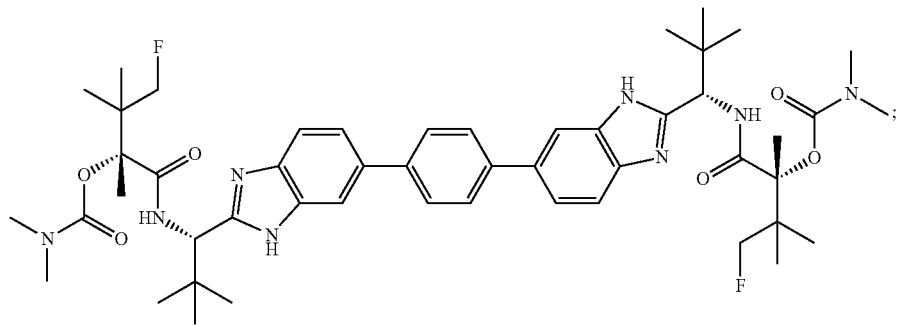
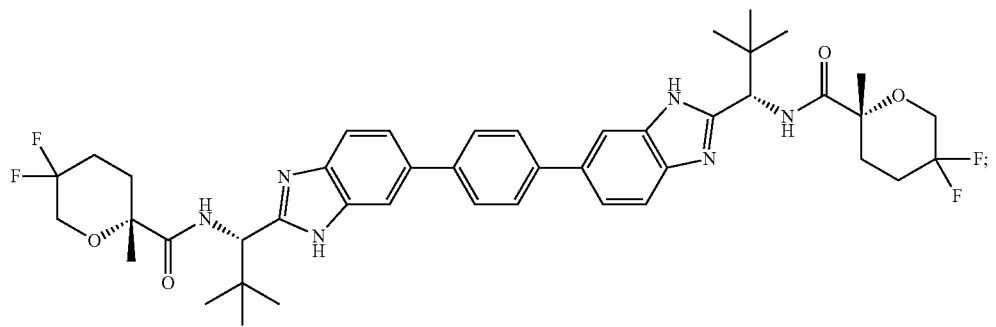
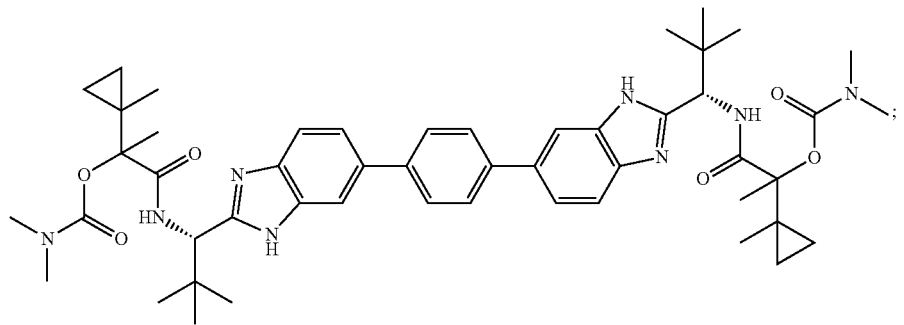
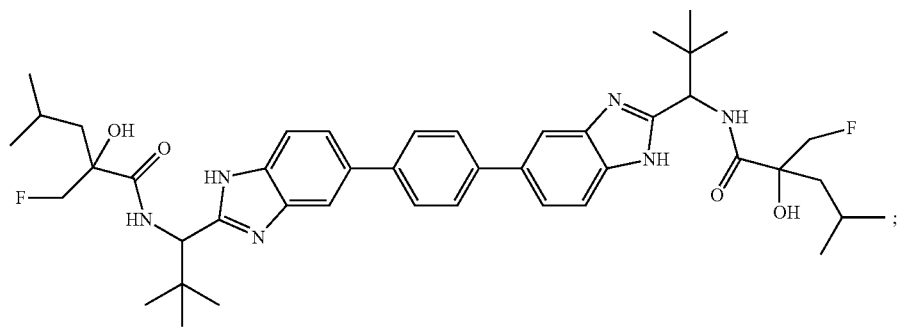

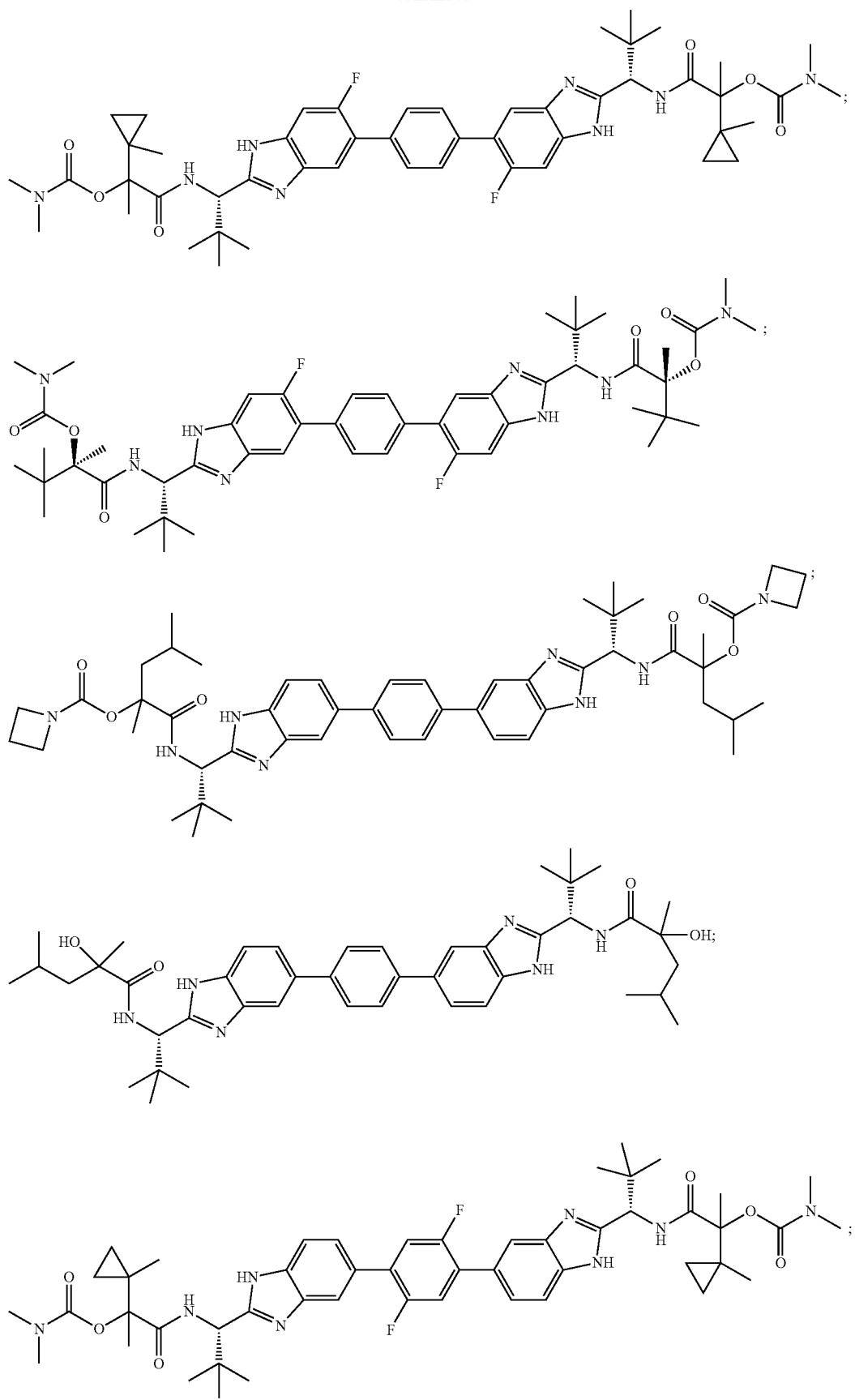

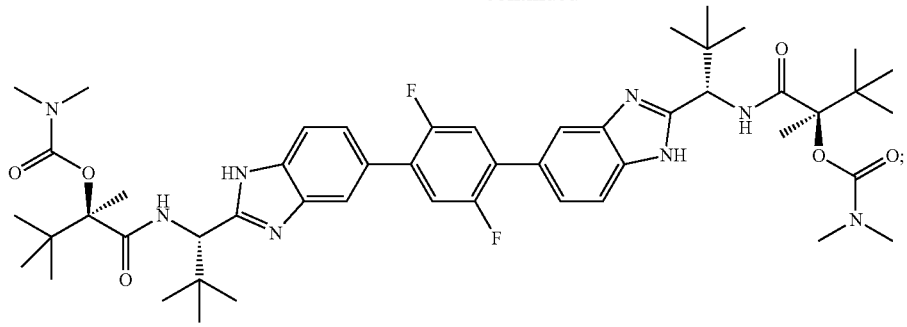

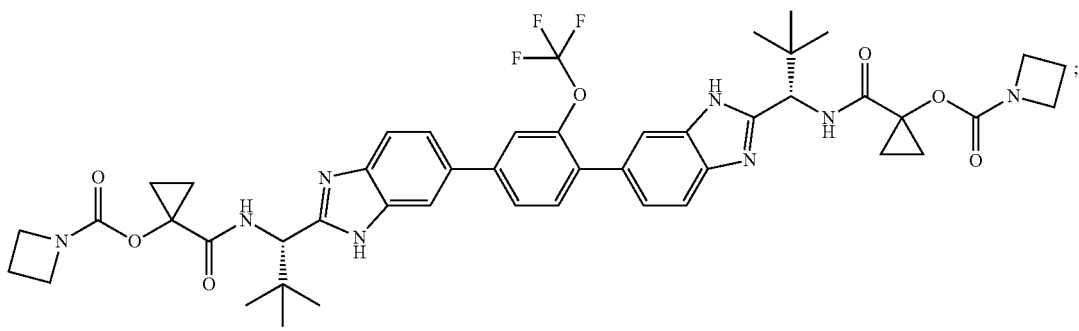

and

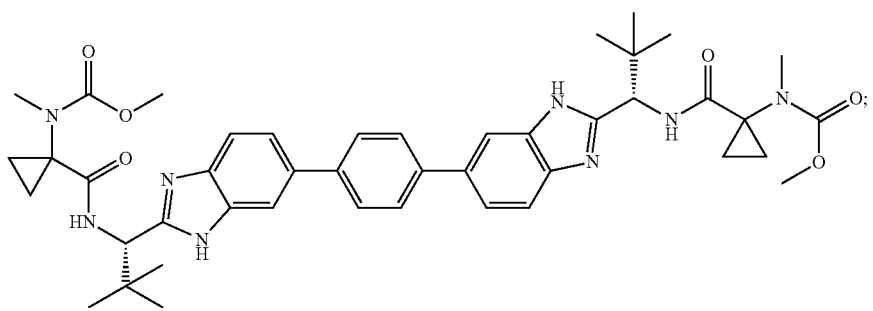 [SMILES: COC(=O)N(C)C1(C(=O)N[C@H](c2nc3ccc(-c4ccc(-c5ccc6nc([C@@H](NC(=O)C7(N(C)C(=O)OC)CC7)C(C)(C)C)[nH]c6c5)cc4)cc3[nH]2)C(C)(C)C)CC1]

or a pharmaceutically acceptable salt thereof.

2. A composition comprising the combination of claim 1 and one or more pharmaceutically acceptable carriers.

3. A method of treating an HCV infection in a patient, comprising administering to the patient a therapeutically effective amount of a combination of claim 1.

4. The method of claim 3 further comprising administering one or two additional compounds having anti-HCV activity prior to, after or simultaneously with the combination.

5. The method of claim 4 wherein at least one of the additional compounds is an interferon or a ribavirin.

6. The method of claim 5 wherein interferon is selected from interferon alpha 2B, pegylated interferon alpha, pegylated interferon lambda, consensus interferon, interferon alpha 2A, and lymphoblastoid interferon tau.

7. The method of claim 4 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

8. A method of treating an HCV infection in a patient, comprising administering to the patient a pharmaceutical composition comprising an NS5A-targeting compound and a pharmaceutical composition comprising an NS5A synergist, which, when administered, provides synergistic anti-HCV activity against variants that contain mutation(s) conferring resistance to the NS5A-targeting compound alone, wherein the NS5A-targeting compound is BMS-790052, or a pharmaceutically acceptable salt thereof, and wherein the NS5A synergist is a compound selected from:

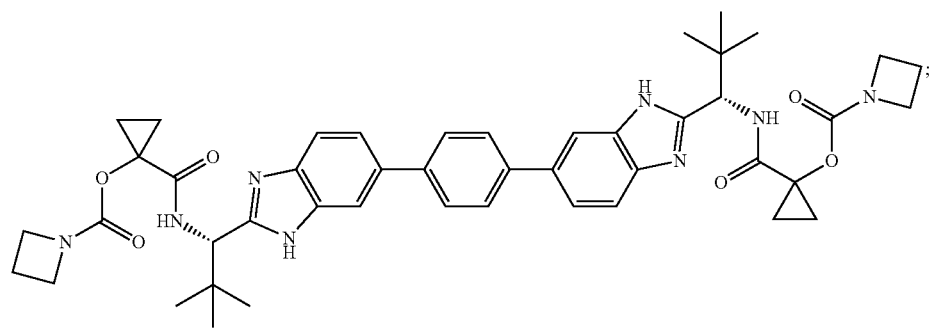
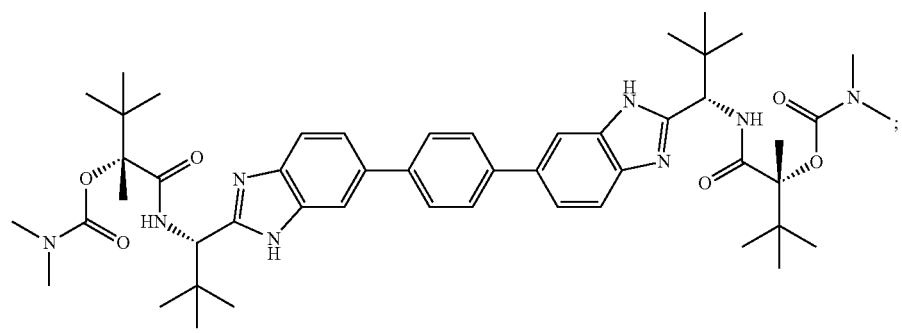
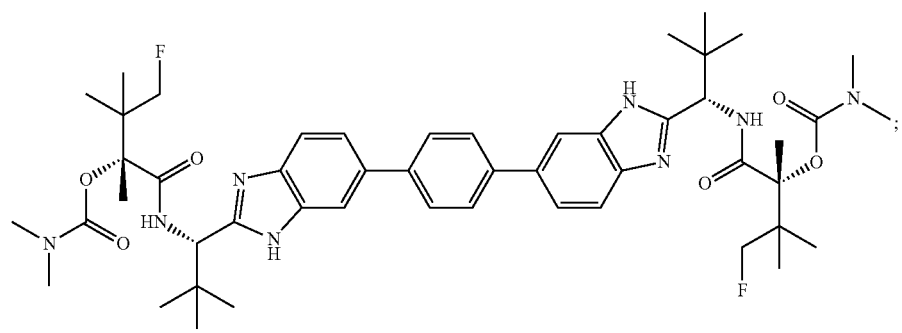
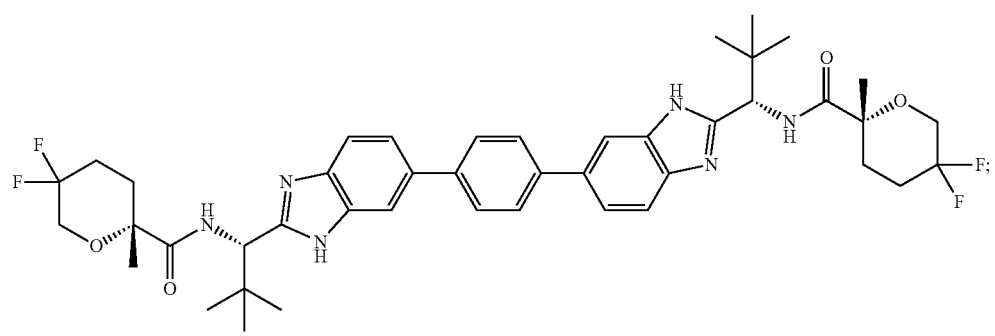
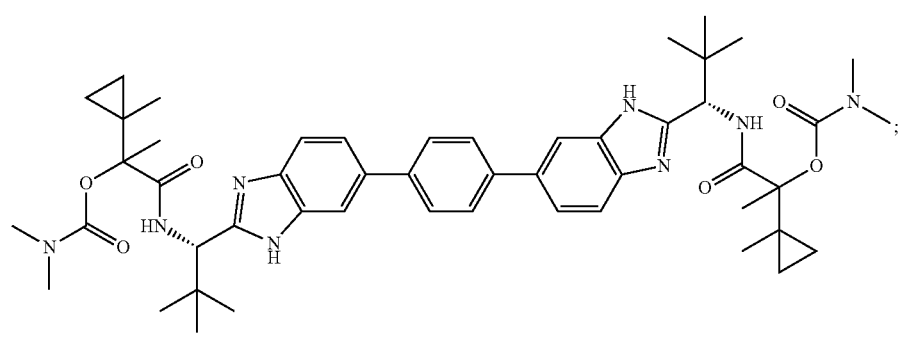

-continued
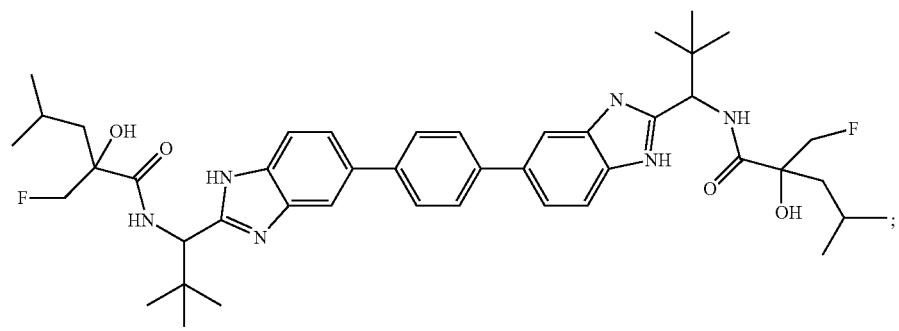
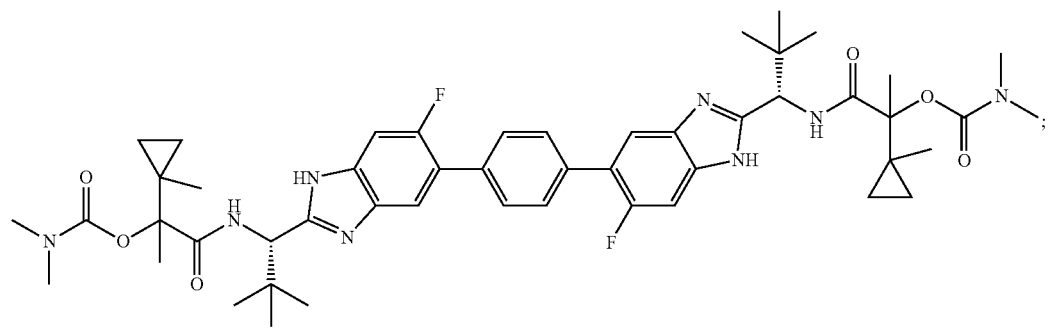
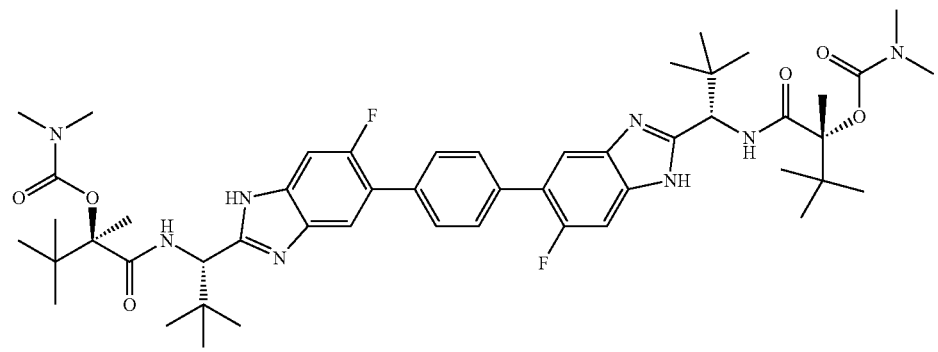
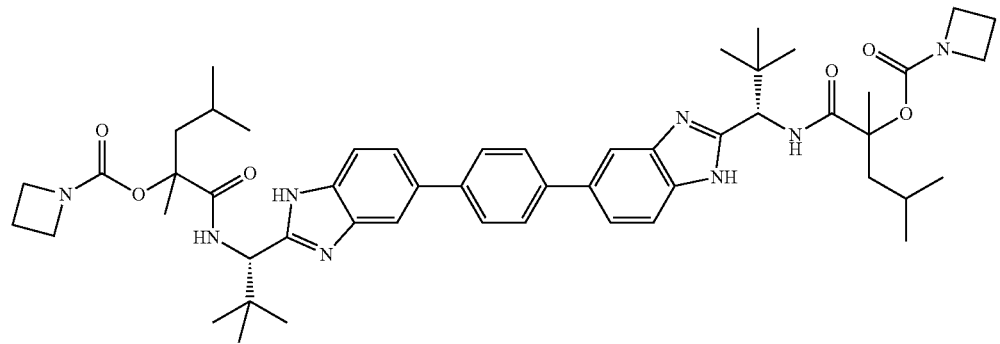
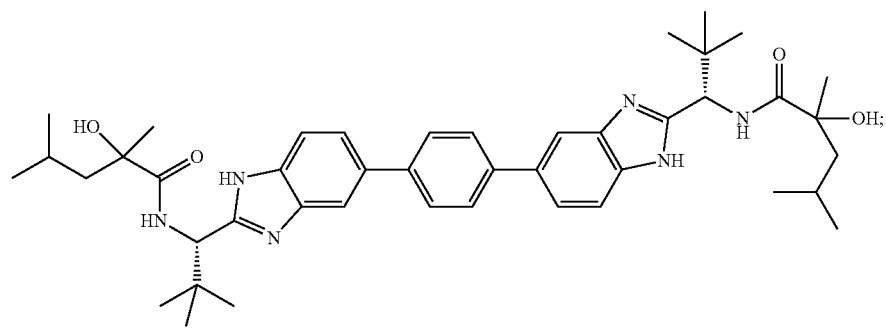

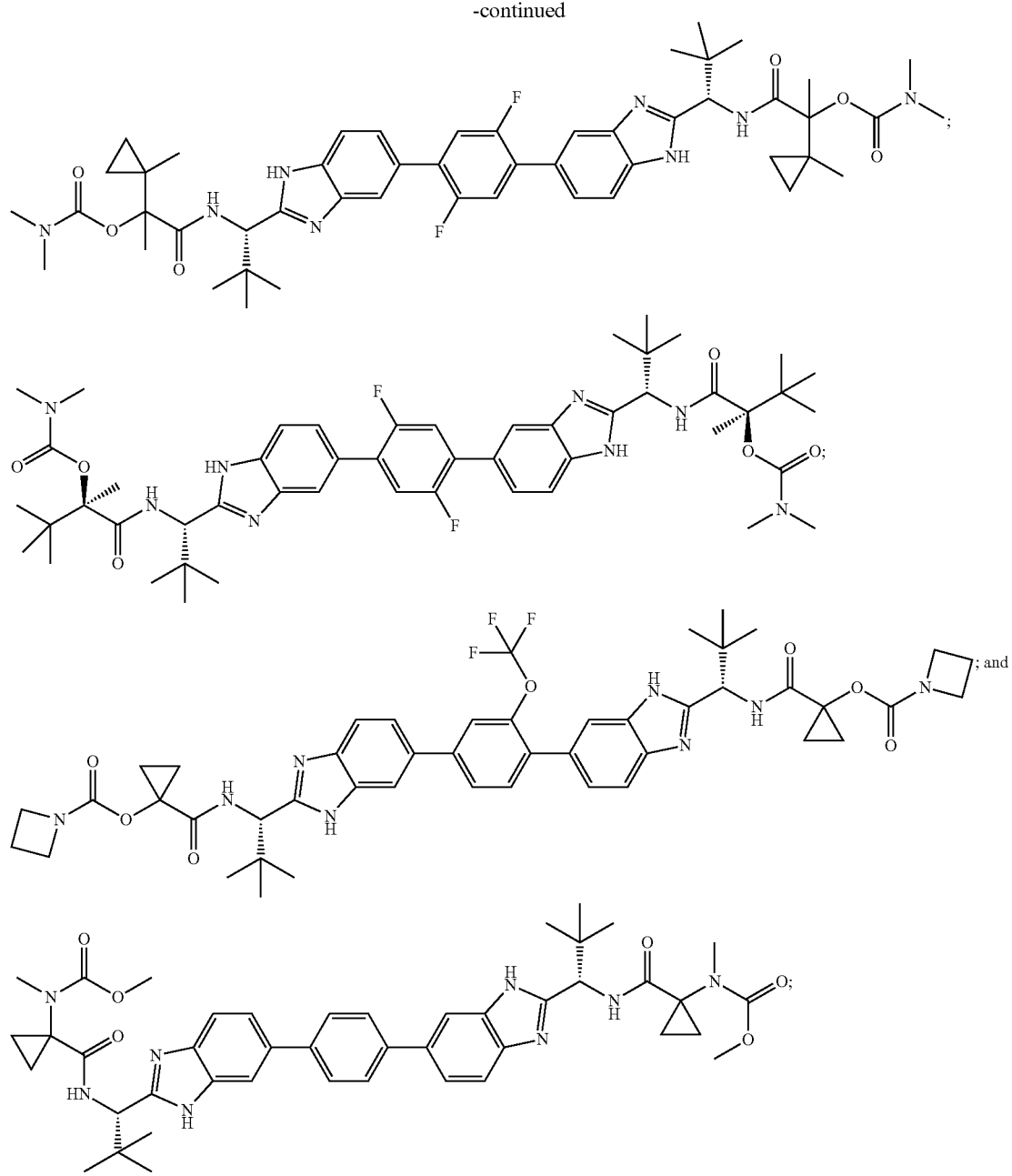
or a pharmaceutically acceptable salt thereof.
9. The method of claim 8, wherein the pharmaceutical composition comprising the NS5A-targeting compound and the pharmaceutical composition comprising the NS5A synergist are administered sequentially.
* * * * *